United States Patent
Schulte et al.

(10) Patent No.: US 11,938,312 B2
(45) Date of Patent: *Mar. 26, 2024

(54) APPARATUS FOR SECURING A THERAPY DELIVERY DEVICE WITHIN A BURR HOLE AND METHOD FOR MAKING SAME

(71) Applicant: Medtronic, Inc., Minneapolis, MN (US)

(72) Inventors: Gregory T. Schulte, Minneapolis, MN (US); Matthew H. Adams, Princeton, MN (US); Shahn S. Sage, Andover, MN (US); Lynn M. Otten, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 338 days.

This patent is subject to a terminal disclaimer.

(21) Appl. No.: 16/148,373

(22) Filed: Oct. 1, 2018

(65) Prior Publication Data

US 2019/0030322 A1    Jan. 31, 2019

Related U.S. Application Data

(63) Continuation of application No. 12/899,679, filed on Oct. 7, 2010, now Pat. No. 10,086,193, which is a
(Continued)

(51) Int. Cl.
*A61N 1/05* (2006.01)
*A61B 17/34* (2006.01)
(Continued)

(52) U.S. Cl.
CPC .... *A61N 1/0539* (2013.01); *A61B 2017/3407* (2013.01); *A61B 2017/347* (2013.01);
(Continued)

(58) Field of Classification Search
None
See application file for complete search history.

(56) References Cited

U.S. PATENT DOCUMENTS

| | | |
|---|---|---|
| 431,187 A | 7/1890 | Foster |
| 438,801 A | 10/1890 | Delehanty |

(Continued)

FOREIGN PATENT DOCUMENTS

| | | |
|---|---|---|
| CA | 2405224 A1 | 10/2001 |
| DE | 3108766 | 9/1982 |

(Continued)

OTHER PUBLICATIONS

"Cross-Hairs Kit", Elekta Instruction for Use Brochure, pp. 2-5.
(Continued)

*Primary Examiner* — Catherine M Voorhees
*Assistant Examiner* — Elizabeth K So
(74) *Attorney, Agent, or Firm* — Harness, Dickey & Pierce, P.L.C.

(57) ABSTRACT

Apparatus for securing a therapy delivery device relative to a burr hole and method for making same. In one embodiment, the apparatus includes a base for seating in or near the burr hole. The apparatus may further include a stabilizer that may be engaged with the therapy delivery device. The stabilizer may include a surface coating or treatment operable to enhance frictional engagement with the therapy delivery device.

7 Claims, 39 Drawing Sheets

Related U.S. Application Data continuation of application No. 11/054,199, filed on Feb. 9, 2005, now abandoned.

(60) Provisional application No. 60/602,749, filed on Aug. 19, 2004, provisional application No. 60/587,356, filed on Jul. 13, 2004, provisional application No. 60/563,787, filed on Apr. 20, 2004, provisional application No. 60/544,456, filed on Feb. 13, 2004.

(51) Int. Cl.
*A61B 90/10* (2016.01)
*A61B 90/11* (2016.01)

(52) U.S. Cl.
CPC . *A61B 2017/3492* (2013.01); *A61B 2090/103* (2016.02); *A61B 90/11* (2016.02)

(56) References Cited

U.S. PATENT DOCUMENTS

| | | |
|---|---|---|
| 873,009 A | 12/1907 | Baxter |
| 1,129,333 A | 2/1915 | Clarke |
| 1,664,210 A | 3/1928 | Hall |
| 2,119,649 A | 6/1938 | Roosen |
| 2,135,160 A | 11/1938 | Beekhuis |
| 2,497,820 A | 2/1950 | Kielland |
| 2,659,371 A | 11/1953 | Schnee |
| 2,686,890 A | 8/1954 | Davis |
| 3,010,347 A | 11/1961 | Kron |
| 3,016,899 A | 1/1962 | Stenvall |
| 3,017,887 A | 1/1962 | Heyer |
| 3,055,370 A | 9/1962 | McKinney et al. |
| 3,055,371 A | 9/1962 | Kulick et al. |
| 3,115,140 A | 12/1963 | Volkman |
| 3,135,263 A | 6/1964 | Connelley, Jr. |
| 3,223,087 A | 12/1965 | Vladyka et al. |
| 3,262,452 A | 7/1966 | Hardy et al. |
| 3,273,559 A | 9/1966 | Evans |
| 3,282,152 A | 11/1966 | Myer |
| 3,402,710 A | 9/1968 | Paleschuck |
| 3,444,861 A | 5/1969 | Schulte |
| 3,457,922 A | 7/1969 | Ray |
| 3,460,537 A | 8/1969 | Zeis |
| 3,508,552 A | 4/1970 | Hainault |
| 3,672,352 A | 6/1972 | Summers |
| 3,760,811 A | 9/1973 | Andrew |
| 3,783,873 A | 1/1974 | Jacobs |
| 3,817,249 A | 6/1974 | Nicholson |
| 3,893,449 A | 7/1975 | Lee et al. |
| 3,981,079 A | 9/1976 | Lenczycki |
| 4,013,080 A | 3/1977 | Froning |
| 4,025,964 A | 5/1977 | Owens |
| 4,026,276 A | 5/1977 | Chubbuck |
| 4,040,427 A | 8/1977 | Winnie |
| 4,131,257 A | 12/1978 | Sterling |
| 4,230,117 A | 10/1980 | Anichkov et al. |
| 4,265,252 A | 5/1981 | Chubbuck et al. |
| 4,312,337 A | 1/1982 | Donohue |
| 4,318,401 A | 3/1982 | Zimmerman |
| 4,328,813 A | 5/1982 | Ray |
| 4,341,220 A | 7/1982 | Perry |
| 4,345,606 A | 8/1982 | Littleford |
| 4,350,159 A | 9/1982 | Gouda |
| 4,355,645 A | 10/1982 | Mitani et al. |
| 4,360,025 A | 11/1982 | Edwards |
| 4,386,602 A | 6/1983 | Sheldon et al. |
| 4,418,894 A | 12/1983 | Mailliet et al. |
| 4,448,195 A | 5/1984 | LeVeen et al. |
| 4,463,758 A | 8/1984 | Patil et al. |
| 4,475,550 A | 10/1984 | Bremer et al. |
| 4,483,344 A | 11/1984 | Atkov et al. |
| 4,571,750 A | 2/1986 | Barry |
| 4,572,198 A | 2/1986 | Codrington |
| 4,579,120 A | 4/1986 | MacGregor |
| 4,592,352 A | 6/1986 | Patil |
| 4,598,708 A | 7/1986 | Beranek |
| 4,608,977 A | 9/1986 | Brown |
| 4,617,925 A | 10/1986 | Laitinen |
| 4,618,978 A | 10/1986 | Cosman |
| 4,629,451 A | 12/1986 | Winters et al. |
| 4,638,798 A | 1/1987 | Shelden et al. |
| 4,638,804 A | 1/1987 | Jewusiak |
| 4,660,563 A | 4/1987 | Lees |
| 4,665,928 A | 5/1987 | Linial et al. |
| 4,699,616 A | 10/1987 | Nowak et al. |
| 4,705,436 A | 11/1987 | Robertson et al. |
| 4,706,665 A | 11/1987 | Gouda |
| 4,733,661 A | 3/1988 | Palestrant |
| 4,755,642 A | 7/1988 | Parks |
| 4,791,934 A | 12/1988 | Brunnett |
| 4,793,355 A | 12/1988 | Crum et al. |
| 4,798,208 A | 1/1989 | Faasse, Jr. |
| 4,805,615 A | 2/1989 | Carol |
| 4,805,634 A | 2/1989 | Ullrich et al. |
| 4,807,620 A | 2/1989 | Strul et al. |
| 4,809,694 A | 3/1989 | Ferrara |
| 4,824,436 A | 4/1989 | Wolinsky |
| 4,826,487 A | 5/1989 | Winter |
| 4,869,247 A | 9/1989 | Howard, III et al. |
| 4,883,053 A | 11/1989 | Simon |
| 4,896,673 A | 1/1990 | Rose et al. |
| 4,902,129 A | 2/1990 | Siegmund et al. |
| 4,922,924 A | 5/1990 | Gambale et al. |
| 4,955,891 A | 9/1990 | Carol |
| 4,956,897 A | 9/1990 | Speedie |
| 4,957,481 A | 9/1990 | Gatenby |
| 4,986,280 A | 1/1991 | Marcus et al. |
| 4,986,281 A | 1/1991 | Preves et al. |
| 4,989,608 A | 2/1991 | Ratner |
| 4,991,579 A | 2/1991 | Allen |
| 4,993,425 A | 2/1991 | Kronberg |
| 4,998,938 A | 3/1991 | Ghajar et al. |
| 5,006,122 A | 4/1991 | Wyatt et al. |
| 5,024,236 A | 6/1991 | Shapiro |
| 5,027,818 A | 7/1991 | Bova et al. |
| 5,030,223 A | 7/1991 | Anderson et al. |
| 5,050,608 A | 9/1991 | Watanabe et al. |
| 5,052,329 A | 10/1991 | Bennett |
| 5,054,497 A | 10/1991 | Kapp et al. |
| 5,057,084 A | 10/1991 | Ensminger et al. |
| 5,057,106 A | 10/1991 | Kasevich et al. |
| 5,065,761 A | 11/1991 | Pell |
| 5,078,140 A | 1/1992 | Kwoh |
| 5,078,142 A | 1/1992 | Siczek et al. |
| 5,080,662 A | 1/1992 | Paul |
| 5,087,256 A | 2/1992 | Taylor et al. |
| 5,099,846 A | 3/1992 | Hardy |
| 5,102,402 A | 4/1992 | Dror et al. |
| 5,116,344 A | 5/1992 | Sundqvist et al. |
| 5,116,345 A | 5/1992 | Jewell et al. |
| 5,120,322 A | 6/1992 | Davis et al. |
| 5,125,888 A | 6/1992 | Howard et al. |
| 5,142,930 A | 9/1992 | Allen et al. |
| 5,143,086 A | 9/1992 | Duret et al. |
| 5,154,179 A | 10/1992 | Ratner |
| 5,154,723 A | 10/1992 | Kubota et al. |
| 5,163,430 A | 11/1992 | Carol |
| 5,166,875 A | 11/1992 | Machida et al. |
| 5,171,217 A | 12/1992 | March et al. |
| 5,174,297 A | 12/1992 | Daikuzono et al. |
| 5,186,174 A | 2/1993 | Schlondorff et al. |
| 5,201,742 A | 4/1993 | Hasson |
| 5,207,223 A | 5/1993 | Adler |
| 5,207,688 A | 5/1993 | Carol |
| 5,211,165 A | 5/1993 | Dumoulin et al. |
| 5,221,264 A | 6/1993 | Wilk et al. |
| 5,222,499 A | 6/1993 | Allen et al. |
| 5,230,338 A | 7/1993 | Allen et al. |
| 5,230,623 A | 7/1993 | Guthrie et al. |
| 5,242,415 A | 9/1993 | Kantrowitz et al. |
| 5,246,448 A | 9/1993 | Chang |
| 5,257,998 A | 11/1993 | Ota et al. |
| 5,263,939 A | 11/1993 | Wortrich |

(56) References Cited

U.S. PATENT DOCUMENTS

| | | |
|---|---|---|
| 5,263,956 A | 11/1993 | Nobles |
| 5,267,970 A | 12/1993 | Chin et al. |
| 5,269,305 A | 12/1993 | Corol |
| 5,279,309 A | 1/1994 | Taylor et al. |
| 5,279,575 A | 1/1994 | Sugarbaker |
| 5,280,427 A | 1/1994 | Magnusson et al. |
| 5,290,266 A | 3/1994 | Rohling et al. |
| 5,291,890 A | 3/1994 | Cline et al. |
| 5,300,080 A | 4/1994 | Clayman et al. |
| 5,305,203 A | 4/1994 | Raab |
| 5,306,272 A | 4/1994 | Cohen et al. |
| 5,309,913 A | 5/1994 | Kormos et al. |
| 5,330,485 A | 7/1994 | Clayman et al. |
| 5,354,283 A | 10/1994 | Bark et al. |
| 5,360,020 A | 11/1994 | Lee, Sr. et al. |
| 5,361,763 A | 11/1994 | Kao et al. |
| 5,366,446 A | 11/1994 | Tal et al. |
| 5,375,588 A | 12/1994 | Yoon |
| 5,375,596 A | 12/1994 | Twiss et al. |
| 5,380,302 A | 1/1995 | Orth |
| 5,383,454 A | 1/1995 | Bucholz |
| 5,387,220 A | 2/1995 | Pisharodi |
| 5,394,457 A | 2/1995 | Leibinger et al. |
| 5,405,330 A | 4/1995 | Zunitch et al. |
| 5,423,832 A | 6/1995 | Gildenberg |
| 5,423,848 A | 6/1995 | Washizuka et al. |
| 5,445,166 A | 8/1995 | Taylor |
| 5,452,720 A | 9/1995 | Smith et al. |
| 5,462,555 A | 10/1995 | Bolanos et al. |
| 5,464,446 A | 11/1995 | Dreessen et al. |
| 5,470,307 A | 11/1995 | Lindall |
| 5,474,564 A | 12/1995 | Clayman et al. |
| 5,483,961 A | 1/1996 | Kelly et al. |
| 5,494,034 A | 2/1996 | Schlondorff et al. |
| 5,494,655 A | 2/1996 | Rocklage et al. |
| 5,515,160 A | 5/1996 | Schulz et al. |
| 5,517,990 A | 5/1996 | Kalfas et al. |
| 5,528,652 A | 6/1996 | Smith et al. |
| 5,541,377 A | 7/1996 | Stuhlmacher |
| 5,572,905 A | 11/1996 | Cook, Jr. |
| 5,572,999 A | 11/1996 | Funda et al. |
| 5,575,798 A | 11/1996 | Koutrouvelis |
| 5,608,382 A | 3/1997 | Webb et al. |
| 5,618,288 A | 4/1997 | Calvo et al. |
| 5,622,170 A | 4/1997 | Schulz |
| 5,638,819 A | 6/1997 | Manwaring et al. |
| 5,639,276 A | 6/1997 | Weinstock et al. |
| 5,643,286 A | 7/1997 | Warner et al. |
| 5,647,361 A | 7/1997 | Damadian |
| 5,649,936 A | 7/1997 | Real |
| 5,658,272 A | 8/1997 | Hasson |
| 5,662,600 A | 9/1997 | Watson et al. |
| 5,667,514 A | 9/1997 | Heller |
| 5,695,501 A | 12/1997 | Carol et al. |
| 5,713,858 A | 2/1998 | Heruth et al. |
| 5,755,697 A | 5/1998 | Jones et al. |
| 5,776,064 A | 7/1998 | Kalfas et al. |
| 5,776,143 A | 7/1998 | Adams et al. |
| 5,776,144 A | 7/1998 | Leysieffer et al. |
| 5,788,713 A | 8/1998 | Dubach et al. |
| 5,807,033 A | 9/1998 | Benway |
| 5,809,694 A | 9/1998 | Postans et al. |
| 5,810,712 A | 9/1998 | Dunn |
| 5,817,106 A | 10/1998 | Real |
| 5,817,116 A | 10/1998 | Takahashi et al. |
| 5,823,975 A | 10/1998 | Stark et al. |
| 5,833,627 A | 11/1998 | Shmulewitz et al. |
| 5,843,150 A | 12/1998 | Dreessen et al. |
| 5,851,183 A | 12/1998 | Bucholz |
| 5,865,817 A | 2/1999 | Moenning et al. |
| 5,865,842 A | 2/1999 | Knuth et al. |
| 5,871,445 A | 2/1999 | Bucholz |
| 5,871,487 A | 2/1999 | Warner et al. |
| 5,873,822 A | 2/1999 | Ferre et al. |
| 5,891,034 A | 4/1999 | Bucholz |
| 5,891,157 A | 4/1999 | Day et al. |
| 5,916,200 A | 6/1999 | Eppley et al. |
| 5,927,277 A | 7/1999 | Baudino et al. |
| 5,950,629 A | 9/1999 | Taylor et al. |
| 5,954,687 A | 9/1999 | Baudino |
| 5,957,933 A | 9/1999 | Yanof et al. |
| 5,957,934 A | 9/1999 | Rapoport et al. |
| 5,964,705 A | 10/1999 | Truwit et al. |
| 5,980,535 A | 11/1999 | Barnett et al. |
| 5,984,930 A | 11/1999 | Maciunas et al. |
| 5,993,463 A | 11/1999 | Truwit |
| 5,997,471 A | 12/1999 | Gumb et al. |
| 6,004,304 A | 12/1999 | Suzuki et al. |
| 6,006,126 A | 12/1999 | Cosman |
| 6,018,094 A | 1/2000 | Fox |
| 6,021,343 A | 2/2000 | Foley et al. |
| 6,024,729 A | 2/2000 | Dehdashtian et al. |
| 6,030,223 A | 2/2000 | Sugimori |
| 6,039,725 A | 3/2000 | Moenning et al. |
| 6,042,540 A | 3/2000 | Johnston et al. |
| 6,044,304 A | 3/2000 | Baudino |
| 6,058,323 A | 5/2000 | Lemelson |
| 6,071,288 A | 6/2000 | Carol et al. |
| 6,076,008 A | 6/2000 | Bucholz |
| 6,079,681 A | 6/2000 | Stern et al. |
| 6,110,182 A | 8/2000 | Mowlai-Ashtiani |
| 6,117,143 A | 9/2000 | Hynes et al. |
| 6,120,465 A | 9/2000 | Guthrie et al. |
| 6,134,477 A | 10/2000 | Knuteson |
| 6,135,946 A | 10/2000 | Konen et al. |
| 6,179,826 B1 | 1/2001 | Aebischer et al. |
| 6,195,577 B1 | 2/2001 | Truwit et al. |
| 6,206,890 B1 | 3/2001 | Truwit |
| 6,210,417 B1 | 4/2001 | Baudino et al. |
| 6,231,526 B1 | 5/2001 | Taylor et al. |
| 6,236,875 B1 | 5/2001 | Bucholz et al. |
| 6,238,402 B1 | 5/2001 | Sullivan, III et al. |
| 6,254,532 B1 | 7/2001 | Paolitto et al. |
| 6,257,407 B1 | 7/2001 | Truwit et al. |
| 6,261,300 B1 | 7/2001 | Carol et al. |
| 6,267,769 B1 | 7/2001 | Truwit |
| 6,267,770 B1 | 7/2001 | Truwit |
| 6,273,896 B1 | 8/2001 | Franck et al. |
| 6,282,437 B1 | 8/2001 | Franck et al. |
| 6,290,644 B1 | 9/2001 | Green, II et al. |
| 6,298,262 B1 | 10/2001 | Franck et al. |
| 6,315,770 B1 | 11/2001 | de la Torre et al. |
| 6,321,104 B1 | 11/2001 | Gielen et al. |
| 6,324,433 B1 | 11/2001 | Errico |
| 6,327,491 B1 | 12/2001 | Franklin et al. |
| 6,356,792 B1 | 3/2002 | Errico et al. |
| 6,368,329 B1 | 4/2002 | Truwit |
| 6,400,992 B1 | 6/2002 | Borgersen et al. |
| 6,457,963 B1 | 10/2002 | Tawara et al. |
| 6,482,182 B1 * | 11/2002 | Carroll ............... A61N 1/0539 607/139 |
| 6,488,620 B1 | 12/2002 | Segermark et al. |
| 6,491,699 B1 | 12/2002 | Henderson et al. |
| 6,529,765 B1 | 3/2003 | Franck et al. |
| 6,537,232 B1 | 3/2003 | Kucharczyk et al. |
| 6,546,277 B1 | 4/2003 | Franck et al. |
| 6,546,279 B1 | 4/2003 | Bova et al. |
| 6,547,795 B2 | 4/2003 | Schneiderman |
| 6,554,802 B1 | 4/2003 | Pearson et al. |
| 6,556,857 B1 | 4/2003 | Estes et al. |
| 6,609,020 B2 | 8/2003 | Gill et al. |
| 6,610,100 B2 | 8/2003 | Phelps et al. |
| 6,623,490 B1 | 9/2003 | Crane et al. |
| 6,632,184 B1 | 10/2003 | Truwit |
| 6,655,014 B1 | 12/2003 | Babini |
| 6,662,035 B2 | 12/2003 | Sochor |
| 6,676,669 B2 | 1/2004 | Charles et al. |
| 6,682,538 B2 | 1/2004 | Qiu et al. |
| 6,706,050 B1 | 3/2004 | Giannadakis |
| 6,726,678 B1 | 4/2004 | Nelson et al. |
| 6,746,471 B2 | 6/2004 | Mortier et al. |
| 6,752,812 B1 | 6/2004 | Truwit |
| 6,765,122 B1 | 7/2004 | Stout |
| 6,773,443 B2 | 8/2004 | Truwit et al. |

(56) References Cited

U.S. PATENT DOCUMENTS

| | | |
|---|---|---|
| 6,782,288 B2 | 8/2004 | Truwit et al. |
| 6,802,323 B1 | 10/2004 | Truwit et al. |
| 6,817,995 B1 | 11/2004 | Halpern |
| 6,902,569 B2 | 6/2005 | Parmer et al. |
| 6,913,478 B2 | 7/2005 | Lamirey et al. |
| 6,944,895 B2 | 9/2005 | Truwit |
| 6,960,216 B2 | 11/2005 | Kolb et al. |
| 7,004,948 B1 | 2/2006 | Pianca et al. |
| 7,094,234 B1 | 8/2006 | Lennox |
| 7,175,642 B2 | 2/2007 | Briggs et al. |
| 7,204,840 B2 | 4/2007 | Skakoon et al. |
| 7,235,084 B2 | 6/2007 | Skakoon et al. |
| 7,285,287 B2 | 10/2007 | Williams et al. |
| 7,329,262 B2 | 2/2008 | Gill |
| 7,366,561 B2 | 4/2008 | Mills et al. |
| 7,454,251 B2 | 11/2008 | Rezai et al. |
| 7,479,146 B2 | 1/2009 | Malinowski |
| 7,497,863 B2 | 3/2009 | Solar et al. |
| 7,532,661 B2 | 5/2009 | Batra et al. |
| 7,559,935 B2 | 7/2009 | Solar et al. |
| 7,580,756 B2 | 8/2009 | Schulte et al. |
| 7,604,644 B2 | 10/2009 | Schulte et al. |
| 7,636,596 B2 | 12/2009 | Solar |
| 7,637,915 B2 | 12/2009 | Parmer et al. |
| 7,658,879 B2 | 2/2010 | Solar |
| 7,660,621 B2 | 2/2010 | Skakoon et al. |
| 7,699,854 B2 | 4/2010 | Mazzocchi et al. |
| 7,704,260 B2 | 4/2010 | Skakoon et al. |
| 7,744,606 B2 | 6/2010 | Miller et al. |
| 7,803,163 B2 | 9/2010 | Skakoon |
| 7,815,651 B2 | 10/2010 | Skakoon et al. |
| 7,828,809 B2 | 11/2010 | Skakoon et al. |
| 7,833,231 B2 | 11/2010 | Skakoon et al. |
| 7,857,820 B2 | 12/2010 | Skakoon et al. |
| 7,867,242 B2 | 1/2011 | Solar et al. |
| 7,896,889 B2 | 3/2011 | Mazzocchi et al. |
| 7,981,120 B2 | 7/2011 | Mazzocchi et al. |
| 8,116,850 B2 | 2/2012 | Solar |
| 8,192,445 B2 | 6/2012 | Parmer et al. |
| 8,845,656 B2 | 9/2014 | Skakoon et al. |
| 8,911,452 B2 | 12/2014 | Skakoon et al. |
| 10,058,681 B2 | 8/2018 | Skakoon et al. |
| 10,086,193 B2 * | 10/2018 | Schulte ............... A61N 1/0539 |
| 10,974,029 B2 | 4/2021 | Skakoon et al. |
| 2001/0003156 A1 | 6/2001 | Gill |
| 2001/0014771 A1 | 8/2001 | Truwit et al. |
| 2001/0027271 A1 | 10/2001 | Franck et al. |
| 2001/0037524 A1 | 11/2001 | Truwit |
| 2002/0010479 A1 | 1/2002 | Skakoon et al. |
| 2002/0019641 A1 | 2/2002 | Truwit |
| 2002/0022847 A1 | 2/2002 | Ray et al. |
| 2002/0052610 A1 | 5/2002 | Skakoon et al. |
| 2002/0077646 A1 | 6/2002 | Truwit et al. |
| 2002/0156372 A1 | 10/2002 | Skakoon et al. |
| 2003/0028199 A1 | 2/2003 | Ghahremani et al. |
| 2003/0079287 A1 | 5/2003 | Truwit |
| 2003/0187351 A1 | 10/2003 | Franck et al. |
| 2003/0199831 A1 | 10/2003 | Morris et al. |
| 2003/0208122 A1 | 11/2003 | Melkent et al. |
| 2004/0026161 A1 | 2/2004 | Takatsuka et al. |
| 2004/0028676 A1 | 2/2004 | Klein et al. |
| 2004/0034367 A1 | 2/2004 | Malinowski |
| 2004/0059260 A1 | 3/2004 | Truwit |
| 2004/0089223 A1 | 5/2004 | Meyer-Fredholm |
| 2004/0105890 A1 | 6/2004 | Klein et al. |
| 2004/0173221 A1 | 9/2004 | Singhal et al. |
| 2004/0176750 A1 | 9/2004 | Nelson et al. |
| 2004/0243146 A1 | 12/2004 | Chesbrough et al. |
| 2004/0243147 A1 | 12/2004 | Lipow |
| 2004/0255991 A1 | 12/2004 | Truwit et al. |
| 2004/0260323 A1 | 12/2004 | Truwit et al. |
| 2004/0267284 A1 | 12/2004 | Parmer et al. |
| 2005/0004602 A1 | 1/2005 | Hart et al. |
| 2005/0015128 A1 * | 1/2005 | Rezai ............... A61N 1/0539 |
| | | 600/378 |
| 2005/0054985 A1 | 3/2005 | Mogg |
| 2005/0065535 A1 | 3/2005 | Morris et al. |
| 2005/0125007 A1 | 6/2005 | Gill |
| 2005/0143799 A1 | 6/2005 | Black et al. |
| 2005/0143800 A1 * | 6/2005 | Lando ............... A61N 1/0539 |
| | | 607/116 |
| 2005/0154297 A1 | 7/2005 | Gill |
| 2005/0182420 A1 | 8/2005 | Schulte et al. |
| 2005/0182421 A1 | 8/2005 | Schulte et al. |
| 2005/0182422 A1 | 8/2005 | Schulte et al. |
| 2005/0182423 A1 | 8/2005 | Schulte et al. |
| 2005/0182424 A1 | 8/2005 | Schulte et al. |
| 2005/0182425 A1 | 8/2005 | Schulte et al. |
| 2005/0182464 A1 | 8/2005 | Schulte et al. |
| 2005/0192594 A1 | 9/2005 | Skakoon et al. |
| 2006/0122627 A1 | 6/2006 | Miller et al. |
| 2006/0192319 A1 | 8/2006 | Solar |
| 2006/0195119 A1 | 8/2006 | Mazzocchi et al. |
| 2007/0250077 A1 | 10/2007 | Skakoon et al. |
| 2007/0250078 A1 | 10/2007 | Stuart |
| 2007/0299427 A1 | 12/2007 | Yeung et al. |
| 2008/0004632 A1 | 1/2008 | Sutherland et al. |
| 2008/0046091 A1 | 2/2008 | Weiss et al. |
| 2008/0058837 A1 | 3/2008 | Steinberg |
| 2008/0082108 A1 | 4/2008 | Skakoon et al. |
| 2010/0179563 A1 | 7/2010 | Skakoon et al. |
| 2011/0022058 A1 | 1/2011 | Skakoon et al. |
| 2011/0022059 A1 | 1/2011 | Skakoon et al. |
| 2011/0034981 A1 | 2/2011 | Schulte et al. |
| 2013/0197472 A1 | 8/2013 | Skakoon et al. |
| 2015/0100064 A1 | 4/2015 | Skakoon et al. |

FOREIGN PATENT DOCUMENTS

| | | |
|---|---|---|
| DE | 3937052 | 5/1990 |
| DE | 19726141 | 1/1999 |
| DE | 29612100 | 8/1999 |
| DE | 19808220 | 9/1999 |
| DE | 19820808 | 9/1999 |
| DE | 19826078 | 11/1999 |
| EP | 0386936 | 5/1990 |
| EP | 0427358 | 5/1991 |
| EP | 0724865 | 5/1991 |
| EP | 0609085 A1 | 8/1994 |
| EP | 0822844 A1 | 2/1998 |
| EP | 0832611 | 4/1998 |
| EP | 0904741 | 3/1999 |
| EP | 1016432 A2 | 7/2000 |
| EP | 1048318 A2 | 11/2000 |
| EP | 1048320 A2 | 11/2000 |
| EP | 1272120 A2 | 1/2003 |
| EP | 1549241 A2 | 7/2005 |
| EP | 1575440 A1 | 9/2005 |
| EP | 1720597 | 11/2006 |
| EP | 1722848 A1 | 11/2006 |
| EP | 1841378 A2 | 10/2007 |
| EP | 1853191 A2 | 11/2007 |
| EP | 1853192 A2 | 11/2007 |
| GB | 2237993 | 5/1991 |
| GB | 2329473 | 4/1998 |
| GB | 2330080 A | 4/1999 |
| GB | 2342583 A | 4/2000 |
| GB | 2346573 | 8/2000 |
| GB | 2355665 A | 5/2001 |
| GB | 2357700 A | 7/2001 |
| WO | 8809151 | 12/1988 |
| WO | 9721380 | 12/1988 |
| WO | 9522297 | 8/1995 |
| WO | 9610368 | 4/1996 |
| WO | 9633766 | 10/1996 |
| WO | 9703609 | 2/1997 |
| WO | 9742870 A1 | 11/1997 |
| WO | 9808554 A1 | 3/1998 |
| WO | 9817191 | 4/1998 |
| WO | 9825535 | 6/1998 |
| WO | 9851229 | 11/1998 |
| WO | 9955408 A1 | 11/1999 |
| WO | 0001316 | 1/2000 |
| WO | 0018306 | 1/2000 |

(56) References Cited

FOREIGN PATENT DOCUMENTS

| | | | |
|---|---|---|---|
| WO | 0013743 | A1 | 3/2000 |
| WO | 0020048 | A1 | 4/2000 |
| WO | 0124709 | | 4/2001 |
| WO | 0149197 | A1 | 7/2001 |
| WO | 0176498 | | 7/2001 |
| WO | 2001076676 | | 3/2002 |
| WO | 2001013714 | | 8/2002 |
| WO | 03068304 | A1 | 8/2003 |
| WO | 2001076498 | A9 | 10/2003 |
| WO | 03090820 | A1 | 11/2003 |
| WO | 2004026161 | A2 | 4/2004 |
| WO | 2004058086 | A1 | 7/2004 |
| WO | 2005079903 | A2 | 9/2005 |
| WO | 2005079912 | A1 | 9/2005 |
| WO | 2006062892 | A2 | 6/2006 |
| WO | 2006062806 | | 12/2007 |
| WO | 2006062824 | | 4/2009 |

OTHER PUBLICATIONS

"CRW™—Tyco Healthcare Radionics", Tyco Product Brochure, pp. 1-7.
"Fathom Remote Introducer", Image-Guided Neurologics, Inc., CNS Hynes Convention Center, 2p., (Oct. 30-Nov. 4, 1999).
"Inomed Competence in Neurophysologic Monitoring", http://www.inomed.com/english/index.htm, (observed Mar. 23, 2004), 2 pgs.
"Leksell Stereotactic System", Elekta Product Brochure, pp. 1-6.
"MicroTargeting® Precision Guidance Using Microelectrode Recording", (Aug. 15, 2003), 5 pgs.
"Possible Existence of Common Internalization Mechanisms among Arginine-rich Peptides", Suzuki, T. et al., Journal of Biological Chemistry, vol. 277, No. 4 (2002) pp. 2437-2443.
"STIMLOC™ by ign," datasheet, NAVIGUS, Image Guided Neurologics, Inc. 2004 (2 pages).
"The ISG Viewing Wand: an application to atlanto-axial cervical surgery using the Le Fort I maxilary osteotomy", British Journal of Oral and Maxillofacial Surgery, 33, (1995) pp. 370-374.
Allison, S., et al., "Microchannel Plate Intensifier Response in Traverse Magnetic Field", Electronic Letters, 26, (Jun. 7, 1990), 770-771.
Beld, Marcel, et al. "Quantitative Antibody Responses to Structural (Core) and Nonstructural (NS3, NS4, and NS5) Hepatitis C Virus Proteins Among Seroconverting Injecting Drug Users: Impact of Epitope Variation and Relationship to Detection of HCV RNA in Blood." (1999) Hepatology vol. 29, No. 4. pp. 1288-1298.
Drake, J.M., et al. "ISG Viewing Wand System", Neurosurgery, 34 (6), (Jun. 1994), 1094-1097.
Dyer, P.V., et al., "The ISG Viewing Wand: an Application to Atlanto-Axial Cervical Surgery Using the Le for I Maxillary Osteotomy", British Journal of Oral and Maxillofacial Surgery, 33, (1995), 370-374.
European Office Action dated Jan. 22, 2010 for European Application No. 05 852 969.4.
Franck Joel, et al., "microTargetingÒ Platform System incorporating StarFix™ guidance", microTargeting, pp. 1-44.
Franck, Joel, et al., "microTargeting® Platform incorporating StarFix™ guidance", microTargeting, 3 pgs.
Gehring, W. J., "Homeodomain Proteins", Annu. Rev. Biochem., vol. 63 (1997) pp. 487-526.
Gillies, G., et al., "Magnetic Manipulation Instrumentation for Medical Physics Research", Review of Scientific Instruments, 65 (3), Review Article, (Mar. 1994), 533-562.
Grady, M., "Nonlinear Magnetic Stereotaxis: Three-Dimensional, in vivo Remote Magnetic Manipulation of a Small Object in Canine Brain", Medical Physics, 17 (3), (May/Jun. 1990), pp. 405-415.
Grady, M., et al., "Initial Experimental Results of a New Stereotaxic Hyperthermia System", American College of Surgeons: 1998 Clinical Congress: Surgical Forum, 39, (1998), 507-509.

Grady, M., et al., "Magnetic Stereotaxis System for Neurosurgical Procedures", Proc. 37th International Instrumentation Symp., Sand Diego, CA (May 1991), 665-675.
Grady, M., et al., "Magnetic Stereotaxis: A Technique to Deliver Stereotactic Hyperthermia", Neurosurgery, 27 (6), Technical Note, (Dec. 1990), pp. 1010-1016.
Grady, M., et al., "Preliminary Experimental Investigation of in vivo Magnetic Manipulation: Results and Potential Application in Hyperthermia", medical Physics, 16 (2), (Mar./Apr. 1989), pp. 263-272.
Guardian™ Cranial Burr Hole Cover System—Clinician's Manual. ANS A St. Jude Medical Companybrochure. Apr. 2009. pp. 1-15.
Hata, N., et al., "Needle Insertion Manipulator for CT- and MR-Guided Stereotactic Neurosurgery", Interventional MR: Techniques and Clinical Experience, St. Louis: London: Mosby; Martin Dunitz, F. Jolesz and I. Young, eds., (1998), 99-106.
Hirschberg, H., et al., "Image-Guided Neurosurgery—MR compatible stereotactic equipment", http:www.medinnova.no/English/P51466ster.html. (Mar. 29, 2001), 1p.
Hirschberg, Henry, et al., "Image-guided neurosurgery", stereotactic equipment for MR imaging, http://www.medinnova.no/English/P51466ster.html, (Observed Mar. 8, 2002), 1 page.
Howard, M., et al., "Magnetic Movement of a Brain Thermocepter", Neurosurgery, 24 (3), (1989), 444-448.
Howard, M., et al., "Magnetic Neurosurgery", Stereotactic and Functional Neurosurgery, 66, (1996), 102-107.
Howard, M., et al., "Magnetic Neurosurgery: Image-Guided, Remote-Controlled Movement of Neurosurgical Implants", Ch. 26 in: Clinical Neurosurgery: Proceedings of the Congress of Neurological Surgeons, San Francisco, CA, (1995), 382-391.
Howard, M., et al., "Review of Magnetic Neurosurgery Research", J. Image Guided Surgery, 1, (Nov. 1995), 295-299.
International Preliminary Examination Report for PCT/US01/11178 completed Jul. 18, 2002, claiming benefit of U.S. Appl. No. 60/195,663, filed Apr. 7, 2000.
International Preliminary Examination Report dated Nov. 25, 2002 for PCT/US01/25904 filed Aug. 17, 2001 claiming benefit of U.S. Appl. No. 60/225,952, filed Aug. 17, 2000.
International Preliminary Report on Patentability and Written Opinion dated Aug. 14, 2006 for PCT/US2005/003970 which claims benefit of U.S. Appl. Nos. 60/544,456; 60/563,787; 60/587,356; U.S. Appl. No. 60/602,749; as does U.S. Appl. No. 12/899,679, filed Oct. 7, 2010.
International Preliminary Report on Patentability and Written Opinion dated Feb. 10, 2009 for PCT/US2005/004141 which claims benefit of U.S. Appl. Nos. 60/544,456; 60/563,787; 60/587,356; 60/602,749; as does U.S. Appl. No. 11/054,199, filed Feb. 9, 2005 and U.S. Appl. No. 12/899,679, filed Oct. 7, 2010.
International Preliminary Report on Patentability for PCT/US2005/043913 dated Mar. 17, 2009, claiming benefit of U.S. Appl. No. 11/005,907, filed Dec. 6, 2004.
International Search Report and Written Opinion for PCT/US05/43651 dated May 8, 2008.
International Search Report and Written Opinion dated Jun. 21, 2005 for PCT/US2005/004141 which claims benefit of U.S. Appl. Nos. 60/544,456; 60/563,787; 60/587,356; 60/602,749; as does U.S. Appl. No. 11/054,199, filed Feb. 9, 2005 and U.S. Appl. No. 12/899,679, filed Oct. 7, 2010.
International Search Report and Written Opinion dated Jun. 3, 2005 for PCT/US2005/003970 which claims benefit of U.S. Appl. Nos. 60/544,456; 60/563,787; 60/587,356; 60/602,749; as does U.S. Appl. No. 11/054,199, filed Feb. 9, 2005 and U.S. Appl. No. 12/899,679, filed Oct. 7, 2010.
International Search Report and Written Opinion dated May 8, 2008 for PCT/US05/43651 claiming benefit of U.S. Appl. No. 11/262,298, filed Oct. 28, 2005 and U.S. Appl. No. 11/005,607, filed Dec. 4, 2004.
International Search Report and Written Opinion dated Nov. 5, 2007 for PCT/US05/43532 claiming benefit of U.S. Appl. No. 11/005,605, filed Dec. 4, 2004.
International Search Report for PCT/US01/11178 dated Feb. 13, 2002, claiming benefit of U.S. Appl. No. 60/195,663, filed Apr. 7, 2004.
International Search Report for PCT/US05/43913 dated Oct. 3, 2008, claiming benefit of U.S. Appl. No. 11/005,907, filed Dec. 6, 2004.

(56) References Cited

OTHER PUBLICATIONS

International Search Report dated Dec. 19, 2001 for PCT/US01/25904 claiming benefit of U.S. Appl. No. 60/225,952, filed Aug. 17, 2000.
International Search Report dated May 28, 2004 for PCT/US03/40610 claiming benefit of U.S. Appl. No. 10/325,615, filed Dec. 20, 2002.
International Search Report dated May 3, 2004 for PCT/US03/28966 claiming benefit of U.S. Appl. No. 60/411,309, filed Sep. 17, 2002.
International Search Report dated Oct. 24, 2001 for PCT/US01/40458 claiming benefit of U.S. Appl. No. 60/195,663, filed Apr. 7, 2000.
Invitation to Pay Additional Fees dated Jan. 15, 2004 for PCT/US03/028966 filed Sep. 17, 2002 claiming benefit of U.S. Appl. No. 60/411,309, filed Sep. 17, 2002.
Lawson, M., et al., "Near Real-Time Bi-planar Fluoroscopic Tracking System for the Video Tumor Fighter", SPIE, 1445, (1991), 265-275.
Leggett, W.B., et al. "Surgical Technology—The Viewing Wand: A New System for Three-Dimensional Computed Tomography-Correlated Intraoperative Localization", Current Surgery, (Dec. 1991), 674-678.
Malison, R. T., et al., "Computer-Assisted Coregistration of Multislice SPECT and MR Brain Images by Fixed External Fiducials", Journal of Computer Assisted Tomography, 17 (6) (1993) pp. 952-960.
Mannervik, M., "Target genes of homeodomain proteins", BioEssays vol. 21.4 (Apr. 1999) pp. 267-270.
McHugh, Thomas M., et al. "The Sensitive Detection and Quantitation of Antibody to HCV by Using a Microsphere-Based Immunoassay and Flow Cytometry." (1997) Cytometry 29:106-112.
McNeil., R., et al., "Characteristics of an Improved Magnetic-Implant Guidance System", IEEE Transactions on Biomedical Engineering, 42 (8), (Aug. 1995), 802-808.
McNeil., R., et al., "Functional Design Features and Initial Performance Characteristics of a Magnetic-Implant Guidance System for Stereotactic Neurosurgery", IEEE Transactions on Biomedical Engineering, 42 (8), (1995), 793-801.
Meeker, D., et al., "Optimal Realization of Arbitrary Forces in a Magnetic Stereotaxis System," IEEE Transactions on Magnetics, 32 (2), (Mar. 1996), 320-328.
Molloy, J., et al., "Experimental Determination of the Force Required for Insertion of a Thermoseed into Deep Brain Tissues", Annals of Biomedical Engineering, 18, (1990), 299-313.
Molly, J., et al., "Thermodynamics of Movable Inductively Heated Seeds for the Treatment of Brain Tumors", Medical Physics; 18 (4), (1991), 794-803.
Notice of Allowance dated Jul. 9, 2010 for U.S. Appl. No. 11/768,077, filed Jun. 25, 2007.
Notice of Allowance dated Jul. 6, 2010 for U.S. Appl. No. 11/768,554, filed Jun. 26, 2007.
Office Action dated Apr. 12, 2011 for U.S. Appl. No. 11/054,649, filed Feb. 9, 2005.
Office Action dated Apr. 29, 2008 for U.S. Appl. No. 11/054,649, filed Feb. 9, 2005.
Office Action dated Apr. 7, 2008 for U.S. Appl. No. 11/054,583, filed Feb. 9, 2005.
Office Action dated Aug. 22, 2016 for U.S. Appl. No. 12/730,724, filed Mar. 24, 2010.
Office Action dated Aug. 25, 2009 for U.S. Appl. No. 11/054,649, filed Feb. 9, 2005.
Office Action dated Aug. 30, 2010 for U.S. Appl. No. 11/054,199, filed Feb. 9, 2005.
Office Action dated Dec. 23, 2009 for U.S. Appl. No. 11/768,077, filed Jun. 25, 2007.
Office Action dated Dec. 9, 2008 for U.S. Appl. No. 11/054,649, filed Feb. 9, 2005.
Office Action dated Feb. 18, 2010 for U.S. Appl. No. 11/054,199, filed Feb. 9, 2005.
Office Action dated Feb. 9, 2016 for U.S. Appl. No. 12/730,724, filed Mar. 24, 2010.
Office Action dated Feb. 9, 2017 for U.S. Appl. No. 12/899,679, filed Oct. 7, 2010.
Office Action dated Jul. 19, 2012 for U.S. Appl. No. 12/899,677, filed Oct. 7, 2010.
Office Action dated Jul. 2, 2013 for U.S. Appl. No. 12/899,674, filed Oct. 7, 2010.
Office Action dated Jul. 23, 2008 for U.S. Appl. No. 11/054,073, filed Feb. 9, 2005.
Office Action dated Jul. 29, 2016 for U.S. Appl. No. 12/899,679, filed Oct. 7, 2010.
Office Action dated Mar. 9, 2016 for U.S. Appl. No. 13/828,136 filed Mar. 14, 2013.
Office Action dated Nov. 10, 2010 for U.S. Appl. No. 11/054,649, filed Feb. 9, 2005.
Office Action dated Nov. 23, 2009 for U.S. Appl. No. 11/768,554, filed Jun. 26, 2007.
Office Action dated Nov. 6, 2013 for U.S. Appl. No. 12/730,724, filed Mar. 24, 2010.
Oliver, L., "Cup-And-Ball Chemopallidectomy Apparatus", (1958), p. 401.
Patikoglou, G. et al., "Eukaryotic Transcription Factor-DNA Complexes", Annual Review of Biophysics and Biomolecular Structure vol. 26 (1997) pp. 289-325.
Quate, E., et al., "Goniometric Motion Controller for the Superconducting Coil in a Magnetic Stereotaxis System", IEEE Transactions on Biomedical Engineering, 38 (9), (Sep. 1991), 899-905.
Ramos, P., et al., "Electro-Optic Imaging Chain for a Biplanar Fluoroscope for Neurosurgery: Magnetic Field Sensitivity and Contrast Measurements", Optical Engineering 32, (7), (1993), 1644-1656.
Ramos, P., et al., "Low-Dose, Magnetic Field-Immune, Bi-Planar Fluoroscopy for Neurosurgery", Proc. SPIE, 1443 (Medical Imaging V: Image Physics), (1991), 160-170.
Ramos, P., et al., "Microchannel Plate Image Intensifier Electron Dynamics in Magnetic Field", Electronics Letters, 27 (18), (Aug. 29, 1991), pp. 1636-1638.
Ritter, R., et al., "Magnetic Stereotaxis: Computer-Assisted, Image-Guided Remote Movement of Implants in the Brain", Ch. 26 in: Computer-Integrated Technology and Clinical Applications, MIT Press, Cambridge, MA., Taylor, R., et al., eds., (1996), 363-369.
Ritter, R., et al., "Magnetic Sterotaxis: An Application of Magnetic Control Technology to the Needs of Clinical Medicine", Proc. of the MAG'95 Industrial Conf. and Exhibition, Technomic Pub. Co., Lancaster, PA., Allaire, P., ed., (1995), 186-193.
Ritter, R., et al., "Stereotaxie Magnetique: Deplacement D'Implants dans le Cerveau, Assistes par Ordinateur et Guides par Imagerie", Innovation et Technologie en Biologie et Medecine, 13, (1992), 437-449.
Sandeman, D.S., et al., "Advances in image-directed neurosurgery: Preliminary experience with the ISG Viewing Wand compared with the Leksell G frame", British Journal of Neurosurgery, 8 (199), pp. 529-544.
Stein, S. et al., "Checklist: Vertebrate homeobox genes", Mechanisms of Development, vol. 55, No. 1 (Mar. 1996) pp. 91-108.
Supplementary European Search Report dated Oct. 26, 2009 for EP05852969 filed Dec. 6, 2005 claiming benefit of U.S. Appl. No. 11/005,907, filed Dec. 5, 2004.
Szikora, I., et al., "Endovascular Treatment of Experimental Aneurysms with Liquid Polymers: The Protective Potential of Stents", Neurosurgery, 38, (Feb. 1996), 339-347.
Vollmer, J. et al., "Homeobox Genes in the Developing Mouse Brain", Journal of Neurochemistry, vol. 71, No. 1 (Jul. 1998) pp. 1-19.
Wolberger, C., "Homeodomain Interactions", Current Opinion in Structural Biology vol. 6, No. 1 (Feb. 1996) pp. 62-68.
Yeh, H.S., et al., "Implantation of intracerebral depth electrodes for monitoring seizures using the Pelorus stereotactic system guided by magnetic resonance imaging", J. Neurosurg., 78 (1993), pp. 138-141.

(56) References Cited

OTHER PUBLICATIONS

Zinreich, S.J., et al., "Frameless Sterotaxic Integration of CT Imaging Data: Accuracy and Initial Applications", Radiology, 188 (3), (1993), pp. 735-742.
Office Action dated Apr. 14, 2010 for U.S. Appl. No. 11/054,649, filed Feb. 9, 2005.

* cited by examiner

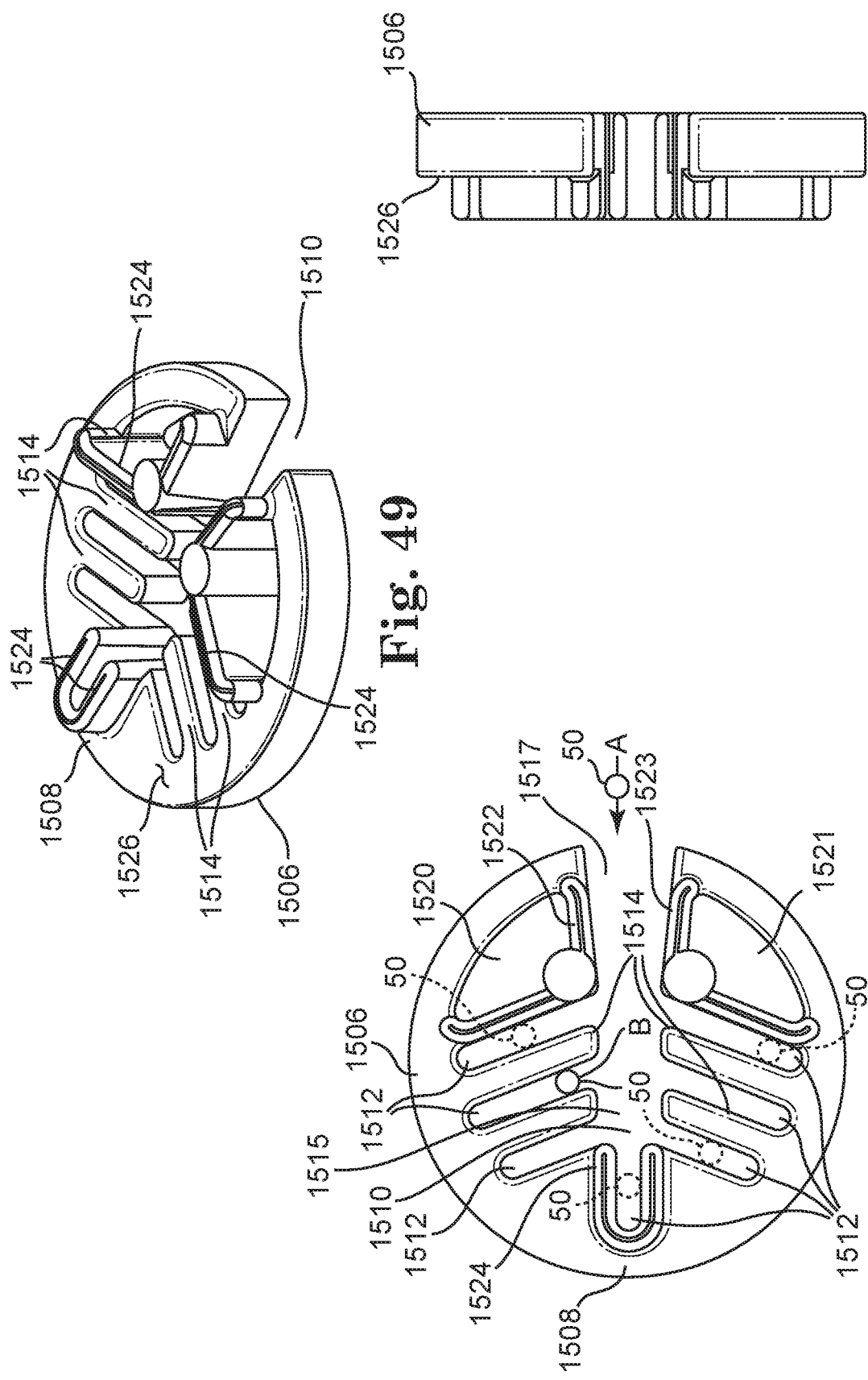

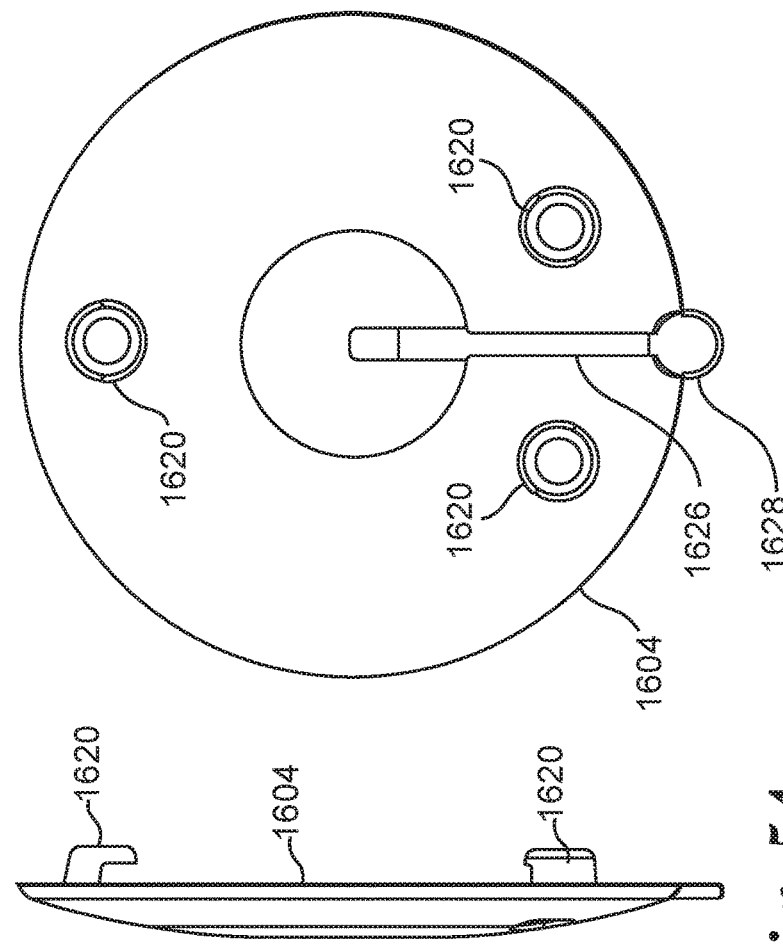
Fig. 55
Fig. 54
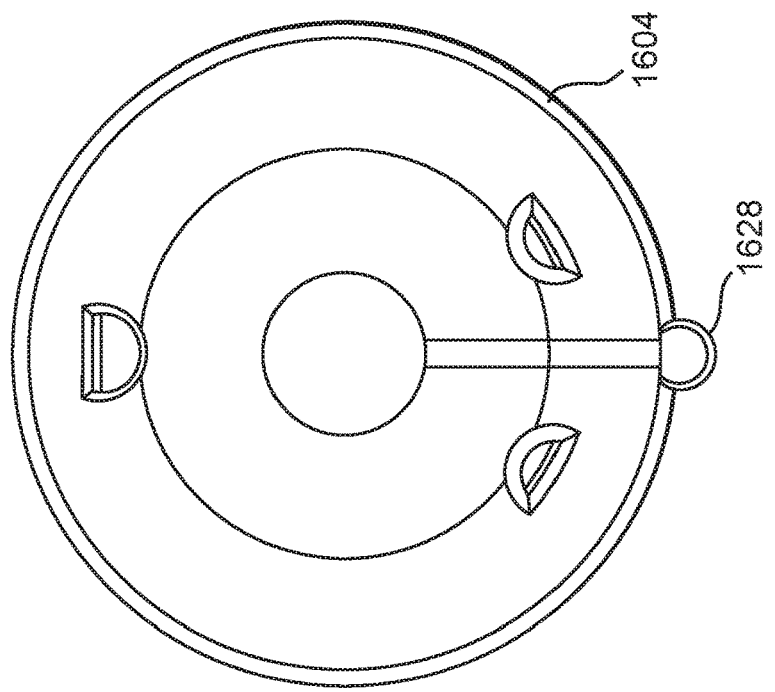
Fig. 53

APPARATUS FOR SECURING A THERAPY DELIVERY DEVICE WITHIN A BURR HOLE AND METHOD FOR MAKING SAME

CROSS-REFERENCE TO RELATED APPLICATIONS

This application is a continuation of U.S. patent application Ser. No. 12/899,679 filed on Oct. 7, 2010, now which is a continuation of U.S. patent application Ser. No. 11/054,199, filed on Feb. 9, 2005, now abandoned, which claims the benefit of (1) United States Provisional Application No. 60/544,456, filed Feb. 13, 2004; (2) United States Provisional Application No. 60/563,787, filed Apr. 20, 2004; (3) United States Provisional Application No. 60/587,356, filed Jul. 13, 2004; and (4) United States Provisional Application No. 60/602,749, filed Aug. 19, 2004. The entire disclosures of each of the above applications are incorporated herein by reference.

FIELD

The present invention relates generally to apparatus for securing therapy delivery devices such as intracerebroventricular catheters, parenchymal catheters, or electrical stimulation leads within or near a burr hole, and to methods for making the same.

BACKGROUND

Medical procedures involving access to the brain through a burr hole in the skull are under increasing use. Such procedures may include electrical stimulation of the brain for purposes such as relief of chronic pain and treatment of movement disorders, and the use of parenchymal or intracerebroventricular catheters for infusing pharmaceutical agents. A typical electrical brain stimulation system includes a pulse generator operatively connected to the brain by a lead having at its distal end an electrode designed to be implanted within the brain, and having at its proximal end a connector assembly designed to connect to the pulse generator. Use of a parenchymal catheter generally involves the insertion of a catheter within the brain to dispense pharmaceutical agents at a specific desired location.

One aspect of the above-listed procedures, and of any other such procedures that involve instrument access to the brain through a burr hole, is the precision with which any such inserted devices, e.g., catheters and leads, are placed. Once a satisfactory burr hole is established at a particular site, to avoid unintended injury to the brain, physicians typically use stereotactic procedures to position the inserted devices. One stereotactic instrument which may be used, for example, to position a lead electrode is disclosed in U.S. Pat. No. 4,350,159 to Gouda. As can be appreciated, once an inserted device is properly positioned, it is important that the device not be moved. Even one millimeter of travel of the positioned device may cause unsatisfactory results or, in some cases, potential injury to the brain. Accordingly, reliable methods and apparatus for fixing the positioned device at the burr hole are beneficial.

Previous systems for securing a positioned device within a burr hole have had drawbacks. For instance, U.S. Pat. No. 4,328,813 to Ray discloses a socket and cap arrangement in which the cap is positioned so as to trap a positioned electrical stimulation lead between the socket and cap. That arrangement involved securing the lead off-center from the burr hole in a manner such that, during installation of the anchoring cap, a stereotactic instrument could not be used to support the lead. Often the lead was manually supported in place while the anchoring cap was being installed. The lead was thus potentially susceptible to inadvertent movement by the physician during cap installation. Further, the interaction of the cap and socket could pull on the lead and potentially result in movement or dislodgement of the same.

SUMMARY OF THE INVENTION

The present invention provides methods and apparatus that overcome drawbacks associated with existing burr hole securing apparatus and techniques. For example, in one embodiment, an apparatus for anchoring a therapy delivery device relative to a burr hole is provided. The apparatus may include a base operable to seat in or near the burr hole, wherein the base includes a peripheral portion at least partially surrounding a central opening. A stabilizer positionable within the central opening may also be included. The stabilizer may include inner surfaces for engaging the therapy delivery device with an interference fit, wherein at least a portion of the inner surfaces of the stabilizer comprise a friction-enhancing coating.

In another embodiment, a method for making a burr hole retention apparatus operable to secure a therapy delivery device relative to a burr hole is provided. The method includes applying a friction-enhancing coating to a stabilizer portion of the retention apparatus.

In yet another embodiment, an implantable therapy delivery system is provided. The system includes a therapy delivery device for implantation through a burr hole, and a therapy source coupled to the therapy delivery device. The system may further include an apparatus for anchoring the therapy delivery device relative to the burr hole. The apparatus may include a base operable to seat in or near the burr hole, wherein the base includes a peripheral portion at least partially surrounding a central opening. A stabilizer positionable within the central opening may also be included, wherein the stabilizer includes inner surfaces for engaging the therapy delivery device with an interference fit. At least a portion of the inner surfaces of the stabilizer include a friction-enhancing coating.

The above summary is not intended to describe each embodiment or every implementation of the present invention. Rather, a more complete understanding of the invention will become apparent and appreciated by reference to the following Detailed Description of Exemplary Embodiments and claims in view of the accompanying figures of the drawing.

BRIEF DESCRIPTION OF THE VIEWS OF THE DRAWING

The present invention will be further described with reference to the figures of the drawing, wherein:

FIGS. 8A-8C are side elevation views of the individual components of the retention apparatus of FIGS. 6 and 7, wherein FIG. 8A illustrates a cover; FIG. 8B illustrates a body; and FIG. 8C illustrates a base or base member;

FIGS. 25A-25B illustrate a burr hole retention apparatus in accordance with yet another embodiment of the invention, wherein: FIG. 25A is an exploded bottom perspective view of the apparatus; and FIG. 25B is an exploded top perspective view;

FIGS. 26A-26B illustrate an exemplary base member for use with the apparatus of FIGS. 25A-25B, wherein: FIG. 26A is a top perspective view thereof; and FIG. 26B is a top plan view thereof;

FIGS. 28A-28D illustrate an exemplary method of using a burr hole retention apparatus of the present invention, e.g., the apparatus of FIGS. 25A and 25B, wherein: FIG. 28A diagrammatically illustrates stereotactic apparatus locating a catheter within a burr hole; FIG. 28B illustrates placement of the retention apparatus within the burr hole; FIG. 28C illustrates positioning of an exemplary stabilizer relative to the retention apparatus; and FIG. 28D illustrates routing of the catheter from the retention apparatus;

FIGS. 32A-32B illustrate the stabilizer of FIG. 31 with the arm shown in a first position, wherein: FIG. 32A is a plan view thereof; and FIG. 32B is a perspective view thereof;

FIG. 47 illustrates a top plan view of a stabilizer in accordance with yet another embodiment of the invention;

FIG. 48 is a side elevation view of the stabilizer of FIG. 47;

FIG. 49 is an upper perspective view of the stabilizer of FIG. 47;

FIG. 53 illustrates a top plan view of a cap member in accordance with another embodiment of the invention;

FIG. 54 is a side elevation view of the cap member of FIG. 53;

FIG. 55 is a bottom plan view of the cap member of FIG. 53; and

DETAILED DESCRIPTION OF THE DRAWINGS

Figure 1:
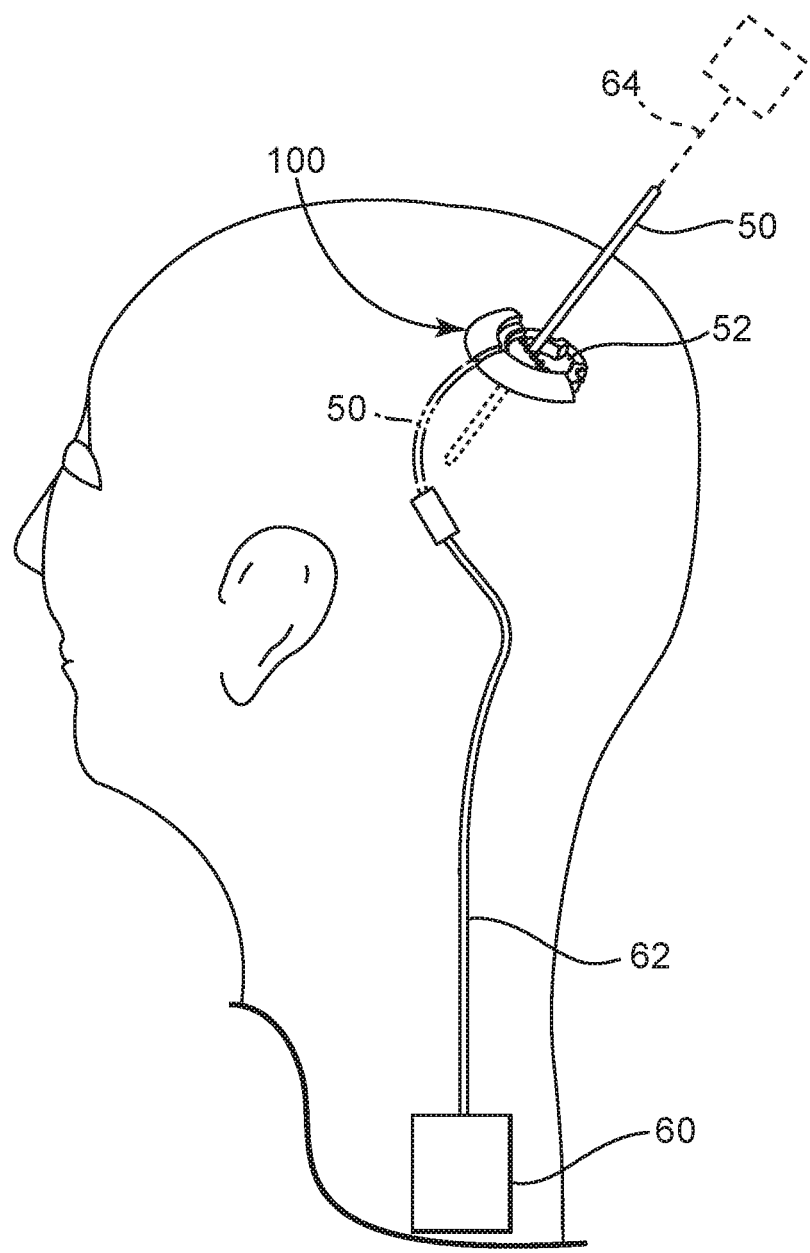
FIG. 1 is a diagrammatic view of a therapy delivery system in accordance with one embodiment of the invention, the system having an infusion pump, a therapy delivery device (e.g., catheter), and an exemplary burr hole retention apparatus.

In the following detailed description of illustrative embodiments of the invention, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the present invention. Unless stated otherwise herein, the figures of the drawing are rendered primarily for clarity and thus may not be drawn to scale.

Generally speaking, the present invention is directed to apparatus, methods, and systems for implanting and anchoring a therapy delivery device relative to a burr hole formed in a human or other mammal.

As used herein, the terms "therapy delivery device," "positioned therapy delivery device," and "positioned device" refer to any elongated medical device having at least proximal and distal ends that: 1) extends through a burr hole; and 2) is to be anchored relative to a known location within or near the burr hole, so that the location of the distal end (the end located within the brain that delivers therapy) of the device may be substantially fixed.

The therapy delivery device itself may be most any medical device capable of delivering therapy to a treatment region. Some exemplary therapy delivery devices include electrical stimulation leads and drug infusion catheters. Regardless of the therapy delivery device used, the distal end of the device will typically be situated within the brain or brain ventricles, where it may be maintained in a stationary position by the retention apparatus.

One benefit of various embodiments of retention apparatus of the present invention is that they may allow implanting a therapy delivery device into a burr hole prior to installing the retention apparatus. As a result, the physician may have unimpeded access to the entire burr hole during device implantation. Moreover, retention apparatus of the present invention are configured to permit side-loading of the device so that the retention apparatus may be installed in the burr hole while the therapy delivery device is held in place with positioning equipment, e.g., with stereotactic apparatus. By using stereotactic apparatus to hold the delivery device during installation of the retention apparatus, inadvertent movement of the delivery device may be minimized.

Embodiments of the retention apparatus described and illustrated herein may also provide multiple, e.g., two or more, interference fits for the therapy delivery device (relative to the retention apparatus) to provide frictional restraint of the device in two or more separate directions. This dual frictional engagement may effectively hold or fix the therapy delivery device in its desired location.

Many of the retention apparatus described herein, see, e.g., apparatus 100, 200, and 300 described below, further have minimal components and, as such, may be manipulated with one hand, a convenience not afforded by many prior art apparatus. Minimizing components may also provide other benefits, e.g., reduced surgical inventory counts.

Still yet another benefit of various embodiments of retention apparatus described herein is that they may be relatively shallow, e.g., have a low profile, and thus not protrude excessively above a cranial surface once in place. This reduced depth may be attributable to various factors including, for example, deep channeled or slotted flanges that permit exiting of the therapy delivery device close to (or in contact with) the cranial surface, and the retention apparatus' ability to function with small diameter devices.

As used herein, the term "snap-fit" refers to a self-locking interconnection between two or more parts (e.g., male and female components) wherein one or both of the parts flex sufficiently during attachment to allow the first part (e.g., male component) to move or slip past a portion of the second part (e.g., female component) until the two parts interlock with one another in a manner that generally prevents their inadvertent separation.

The term "interference fit," as used herein, refers to the interconnection of a male component with a female component wherein the male component has an effective undeflected interfacing dimension, e.g., an outer diameter, that is larger than the undeflected receiving dimension, e.g., inner diameter, of the female component. One or both of the male and female components may deflect or deform sufficiently to permit assembly of the components. For example, a female component in accordance with embodiments of the present invention may have a major dimension about 2% to about 50% less than an undeflected outer dimension of a mating male component (e.g., the catheter 50). However, most any relative size of male and female components is contemplated as long as the components may be coupled with interference and without inducing failure or collapse of the components.

As used herein, the term "fixed" refers to one component being generally immobilized relative to another component during normally anticipated activity. For example, a catheter that is described as fixed relative to a retention apparatus indicates that the catheter may remain generally immobilized relative to the retention apparatus during normal subsequent patient activity.

FIG. 1 illustrates an exemplary therapy delivery system incorporating a retention apparatus 100 in accordance with one embodiment of the present invention. For purposes of explanation, the exemplary therapy delivery device is described and illustrated herein in the context of a brain infusion catheter 50. The catheter 50 may enter the cranium through a burr hole 52 formed at a predetermined location. A stylet 64 may be inserted through the catheter 50 to assist with its placement within the brain. The retention apparatus 100 may be located in the burr hole 52 to assist in securing the catheter 50 in the desired location.

Once the catheter 50 is secured relative to the retention apparatus 100, its proximal end may be placed against the surface of the skull and connected to a therapy source, e.g., an implanted infusion pump 60, via a second catheter, e.g., an infusion pump catheter 62.

While the exact size and construction of the catheter 50 may certainly vary without departing from the scope of the invention, it may, in one embodiment, be constructed of polyurethane having a durometer of about 80 Shore A. It may further have an outer undeflected diameter of about 0.9 millimeters (mm) to about 1.1 mm, e.g., about 1 mm. Other exemplary materials may include silicone, or co-extrusions such as silicone/nylon or silicone/polyurethane.

Retention apparatus in accordance with the present invention may be placed directly within a burr hole or, alternatively, within a pre-positioned burr hole ring. The decision to utilize a separate burr hole ring may depend on a patient's individual circumstances as well as on other factors such as the size or shape of the burr hole, what devices may be located through the burr hole, etc.

For brevity, the apparatus illustrated and described herein do not utilize a separate burr hole ring. That is, the retention apparatus shown herein may include an integral burr hole ring rather than utilize a separate component. However, configurations utilizing a separate burr hole ring are certainly possible without departing from the scope of the invention. Examples of burr hole rings are described, for example, in U.S. Pat. No. 5,927,277 to Baudino et al. and U.S. Pat. No. 5,954,687 to Baudino.

The components of the exemplary retention apparatus described herein (e.g., bases, stabilizers, and caps) may be made from most any biocompatible material including plastics, metals, etc. For example, materials selected from the group consisting of nylon, polyurethane, polycarbonate, polyamide, and polyetheretherketone (PEEK) (including combinations thereof) may be used.

Moreover, as further described below, some portions of the exemplary retention apparatus described and illustrated herein may include materials, e.g., surface coatings, that increase frictional resistance (coefficient of friction) between a coated surface and the therapy delivery device, e.g., catheter 50. The actual materials and/or coatings, if used, may be selected based upon particular therapy delivery regimens and/or other specific patient requirements.

FIGS. 2-5 illustrate a retention apparatus 100 in accordance with one exemplary embodiment of the present invention. The apparatus 100 may be a two-piece construction having a base or base member 102 and a cap or cap member 104 (see, e.g., FIG. 2). The base 102 may be generally ring-shaped and at least partially surround a central portion of the base, the central portion defining a central opening 128 extending through the base.

The base 102 may include a lower engagement portion 106 that is generally annular- or ring-shaped. The engagement portion 106, as further described below, may seat against an inner surface of the burr hole when the base 102 is implanted. A passageway or opening 108 may extend through the engagement portion 106 such that the base forms a generally C-shaped component in plan view.

Openings 109 may be formed or otherwise included on the base 102, e.g., on the lower engagement portion 106. The openings 109 may define tool interface surfaces operable to receive forceps, or other suitable devices, for squeezing the engagement portion 106 to a diameter slightly smaller than the nominal diameter of the burr hole. By squeezing or compressing the engagement portion 106, the base 102 may be placed within the burr hole, whereby, upon release of the squeezing force, the engagement portion may expand and secure the base within the burr hole. To assist with retention of the base 102 relative to the inner surfaces of the burr hole, an outer surface 112 of the engagement portion 106 may include surface variations (e.g., protrusions, threaded grooves, or serrations) as shown in other embodiments described below.

While illustrated herein as utilizing frictional interlocking with the burr hole, other embodiments of the retention apparatus 100 (or any of the other embodiments described herein below) may also be secured relative to the skull with mechanical fasteners such as screws or the like.

The base 102 may also include a peripheral portion defined by an upper flange portion 110 that extends above a cranial surface when the retention apparatus 100 is implanted. The upper flange portion 110 may be formed over only a portion, e.g., about 180 degrees, of the lower engagement portion 106. The upper flange portion 110 may have a larger diameter than the lower engagement portion 106 so that, when the base 102 is placed in the burr hole, the upper flange portion 110 may seat against the cranial surface and thus prevent over-insertion of the base.

Preferably, the retention apparatus 100, as well as all other embodiments of retention apparatus described elsewhere herein, has a low profile. As used herein, the term "low profile" indicates a retention apparatus, e.g., base 102, that protrudes only minimally above the outer cranial surface. For example, in some embodiments, a maximum height of the peripheral/flange portion (e.g., the height that the bases described herein may extend above the cranial surface when the base is correctly positioned within the burr hole) is about 4 mm (about 0.16 inches) or less; preferably, about 3.3 mm (about 0.13 in) or less; more preferably about 3 mm (about 0.12 in) or less; and most preferably about 2.5 mm (about 0.10 in) or less. For example, the base 102 could, in one embodiment, extend about 2 mm (about 0.08 in) from the cranial surface when installed. As a result, the flange portion 110 may, in some embodiments, have a thickness (a distance from its lower surface to its uppermost surface) of about four times (about 400%) or less, preferably about three times or less, an undeflected outer dimension of the catheter 50.

Various features of exemplary retention apparatus described herein may contribute to the resulting low profile. For instance, the apparatus 100, like other retention apparatus described herein, may recess a portion, see, e.g., a stabilizer or stabilizer portion 116, within the burr hole, i.e., may locate the stabilizer portion at a location below the surface of the skull. Thus, sufficient room may exist to route the catheter within the overall burr hole envelope. Further, for example, a channel or slot may be provided in the retention apparatus (see, e.g., channel 132 formed in an upper surface of the flange portion 110 in FIG. 2). The channel 132 may permit the catheter 50 to exit the retention apparatus 100 within the envelope defined by the flange portion.

Figure 2:
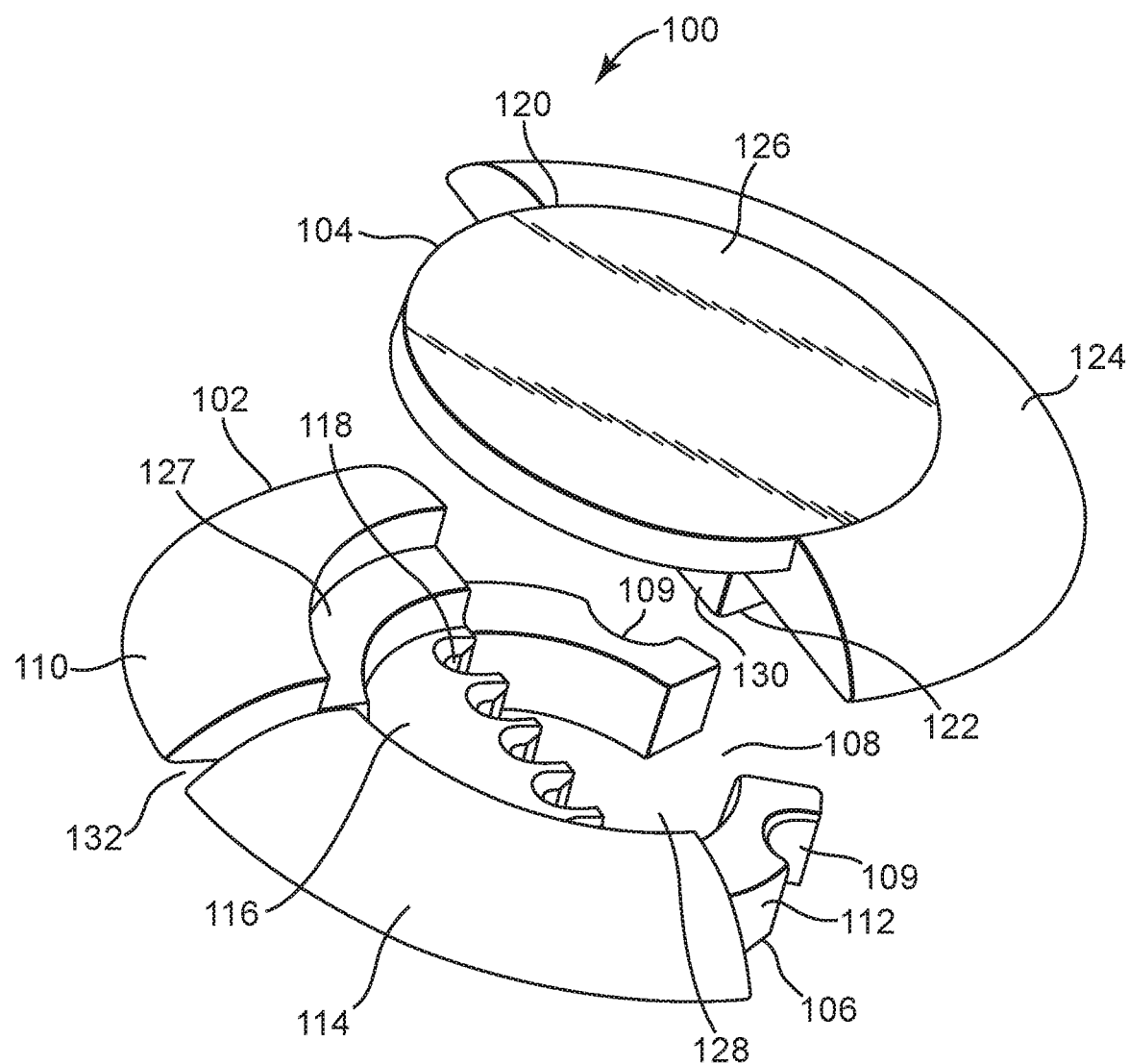
FIG. 2 is an exploded perspective view of a burr hole retention apparatus in accordance with one embodiment of the invention.
Figure 3:
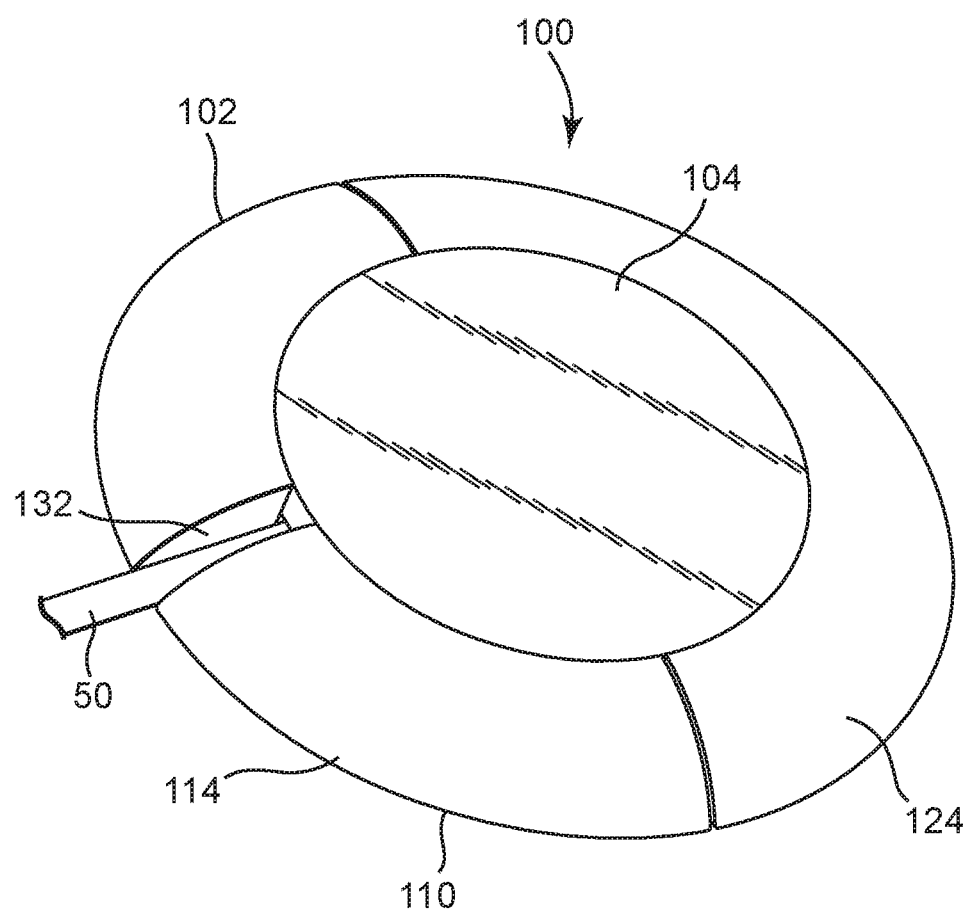
FIG. 3 is a perspective view of the apparatus of FIG. 2 as assembled.

The base 102, e.g., upper flange portion 110, may transition to its outermost edge via a smooth transitional surface, such as a curved surface 114, as shown in FIGS. 2-3. The curved surface 114, which may be defined by a relatively large radius, in combination with the low profile design of the flange portion 110, may reduce or eliminate bulging and excessive stress to the patient's skin when it subsequently covers the retention apparatus 100.

The stabilizer portion 116 of the retention apparatus 100 may have a sidewall with at least one, and preferably more, securing features such as open-sided notches or apertures 118. Each notch 118 may be sized to frictionally receive and secure the catheter 50 (e.g., receive the catheter with an interference fit) so that the catheter may be secured at any one of several discrete locations along the sidewall. Preferably, the notches 118 are open-sided, e.g., C-shaped, such that the catheter(s) 50 may be side-loaded into the notches rather than threaded therethrough. By providing numerous notches 118, the exact location of the catheter 50 within the burr hole may be varied to accommodate the desired catheter location.

In an exemplary embodiment, the notches 118 may have a minimum diameter of about 0.96 mm to receive a catheter 50 (see FIG. 4) having, for example, an undeflected outer diameter of about 1 mm. As described above, the catheter 50 may be made from a relatively flexible material (e.g., polyurethane having a durometer of about 80 Shore A) so that it may deform sufficiently to engage the apertures 118 with the desired interference fit.

The stabilizer portion 116 may, as illustrated in FIGS. 2-5, be integrally formed with the base 102. In other embodiments, as further described below, the stabilizer 116 may be a separate component that attaches to the base 102 prior to, or during, implantation.

The cap member 104 (FIG. 2) may engage the base 102 once the catheter 50 is in place as further described below. When the cap member 104 is so attached to the base 102, the retention apparatus 100 may form a generally disk- or button-shaped device having the generally continuous transitional surface 114 (except for the channel 132) as shown in FIG. 3.

The cap member 104 may include, in one embodiment, a lid portion 120 and a tab portion 122. The lid portion 120 may further include: an outer flange portion 124 that has a size and shape complimentary to the surface 114 of the flange portion 110 of the base 102 (see FIG. 2); and an inner cover portion 126. The inner cover portion 126 may be configured to be received within a recess 127 of the base 102.

Figure 4:
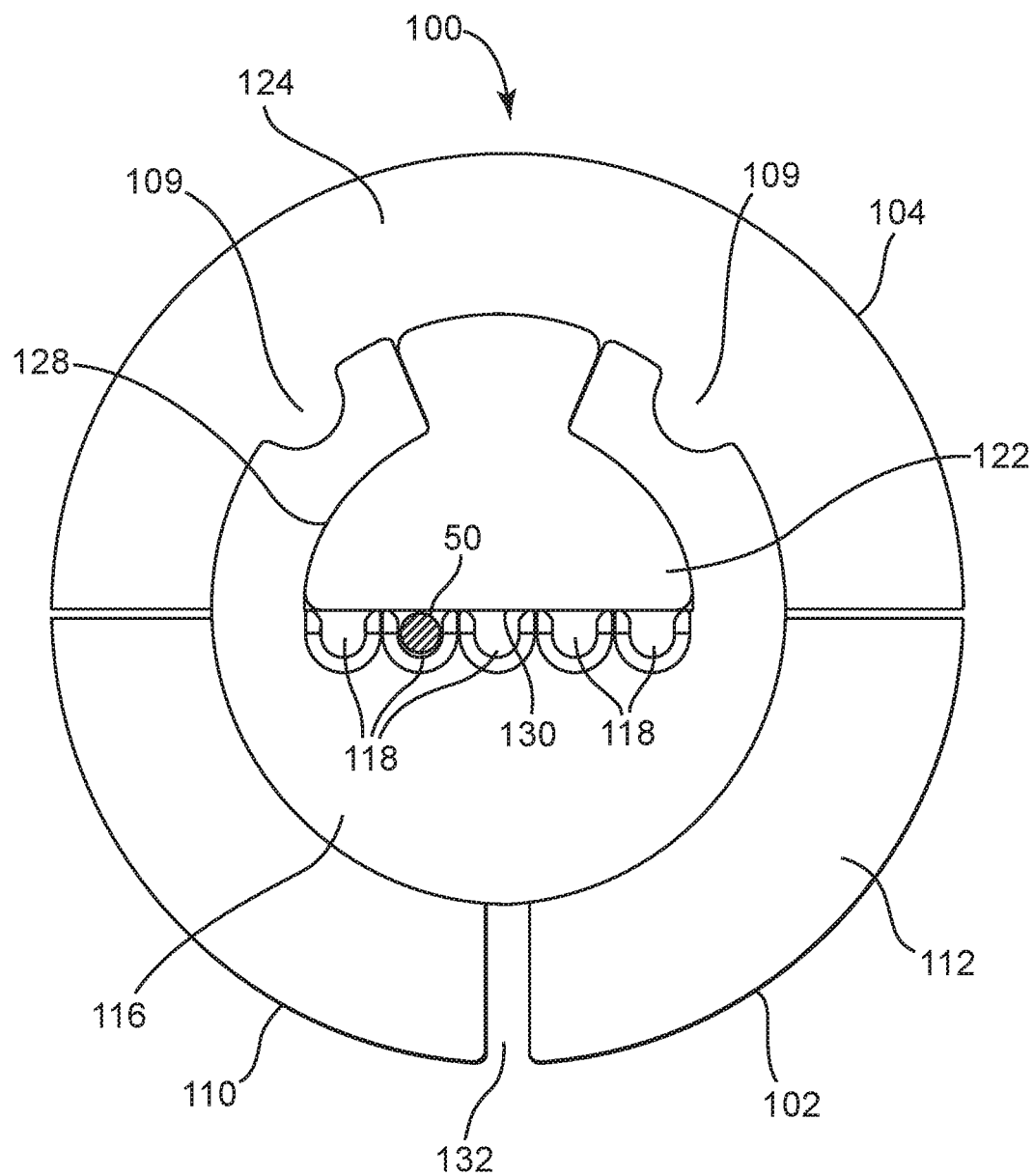
FIG. 4 is a bottom plan view of the assembled apparatus of FIG. 2.

The tab portion 122 may be configured to engage the central opening 128 in the base 102 as best illustrated in FIG. 4. Preferably, the tab portion 122 (or the lid portion 120) engages the base 102 with a snap fit so that some degree of positive coupling is achieved between the components. When assembled, a surface 130 of the tab portion 122 may fit against the sidewall and the open-sided notches 118 of the stabilizer portion 116 to positively retain or trap the catheter 50 within one of the notches 118.

The stabilizer portion 116 may be located at an elevation below the recess 127 (see FIG. 2) such that a space exists between the top of the stabilizer portion 116 and the bottom of the inner cover portion 126 when the cap member 104 is attached to the base 102.

Figure 5:
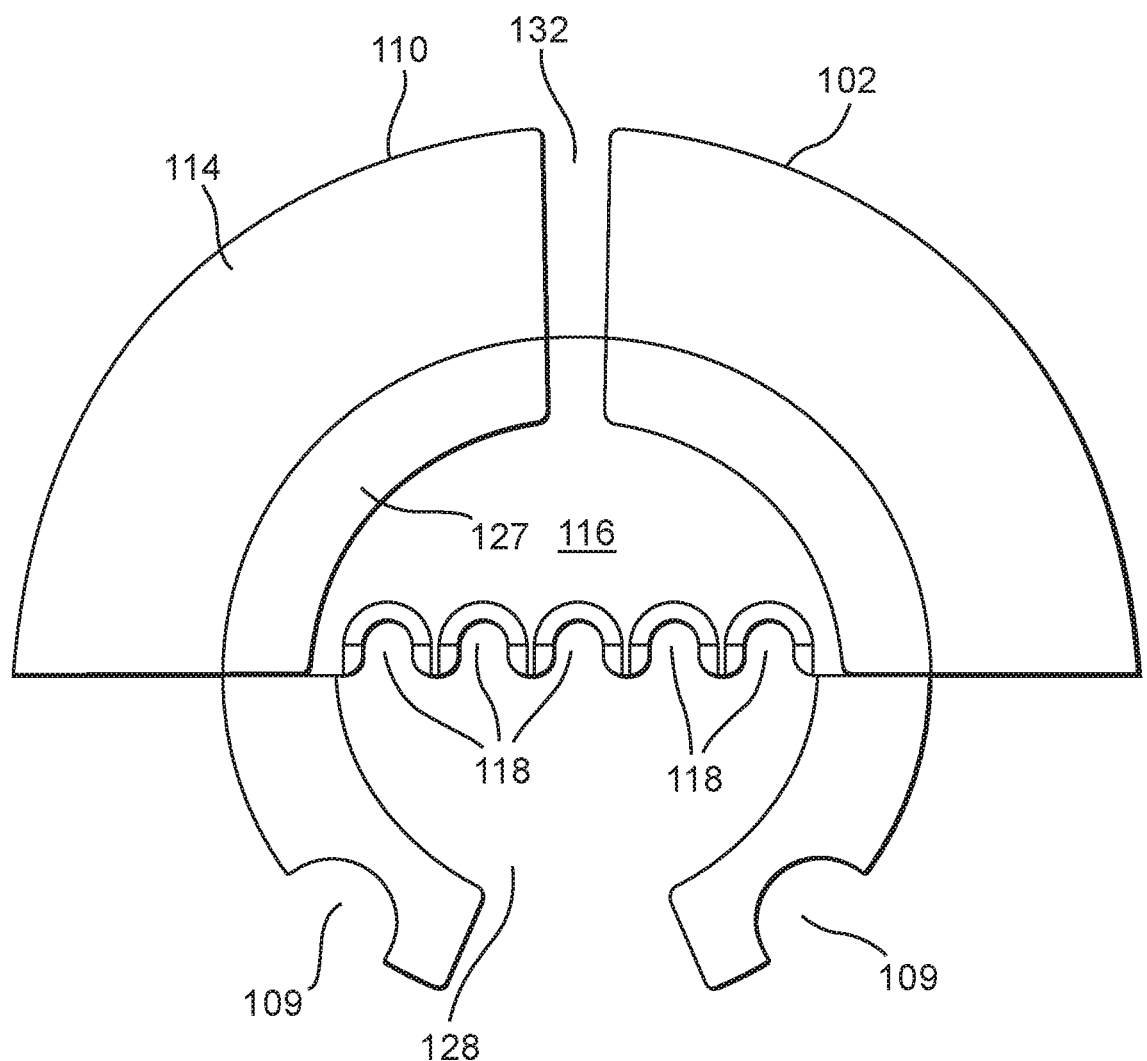
FIG. 5 is a top plan view of a base member of the retention apparatus of FIG. 2.

The channel 132 may be formed in an upper surface of the flange portion 110. The channel may extend outwardly from an inner edge of the flange portion, e.g., from the recess 127/central opening 128, through an outer edge as shown in FIG. 2. In one embodiment, the channel 132 may extend downwardly through a depth of the flange portion 110 (see, e.g., FIG. 5). That is, the channel 132 may form a slot extending from an upper surface through a lower surface of the flange portion 110 as shown in FIGS. 4 and 5 generally above the engagement portion 106. In other embodiments, the channel 132 may be more shallow, e.g., it may form only a recess in the upper surface of the flange portion.

The channel 132 is preferably sized to receive the catheter 50 with an interference fit, e.g., a fit similar to that described with respect to the catheter 50 and the notch 118. Once the catheter 50 is located in the channel 132, the cap member 104 may be attached to the base 102 as described below.

While illustrated with only a single channel 132, other embodiments of the base 102 may incorporate additional channels as desired. Moreover, other embodiments may utilize channels of different configurations such as a circuitous or other non-linear channel as described below with respect to other embodiments.

To implant a therapy delivery device (e.g., catheter 50) into the brain with the retention apparatus 100 described above, the following exemplary procedure may be utilized. After locating the desired cranial entry location, a burr hole may be created in the skull of the patient (see FIG. 1). Stereotactic apparatus equipment may then be utilized to position the catheter 50 at the desired location within the brain. A stylet (e.g., stylet 64 in FIG. 1) may be placed in the catheter 50 prior to insertion to give the catheter 50 rigidity during the implantation process.

Once the catheter 50 is positioned, the base 102 may be side-loaded over the catheter (e.g., the base may be placed over the catheter by guiding the latter through the passageway 108) until the catheter is positioned in the central opening 128. The base 102 is then slid longitudinally along the catheter 50 towards the burr hole.

The base 102 may then be inserted into the burr hole by compressing the lower engagement portion 106 with forceps inserted into the openings 109. The base 102 may be oriented to ensure that the channel 132 extends in the desired direction, e.g., towards the infusion pump catheter 62 (see FIG. 1). The base 102 may be inserted into the burr hole until the lower surface of the upper flange portion 110 contacts the cranial surface.

Prior to or after base insertion, the catheter 50 may be slid into the desired notch 118 where it may seat with an interference fit. Upon verification that the catheter 50 is in the desired location, the catheter 50 may be removed from the stereotactic apparatus and the stylet (if used) may be withdrawn from the catheter.

With the stylet removed, the catheter 50 may be routed and placed into the channel 132 of the base 102, where it may seat with an interference fit. The cap member 104 may then be coupled to the base 102, whereby the surface 130 (see FIG. 4) is located adjacent an open side of the notches 118 to generally trap the catheter 50 within the desired notch. As stated above, the interference fits between the catheter 50 and both the notch 118 and the channel 132 serve to fix the catheter in the desired position.

Figure 6:
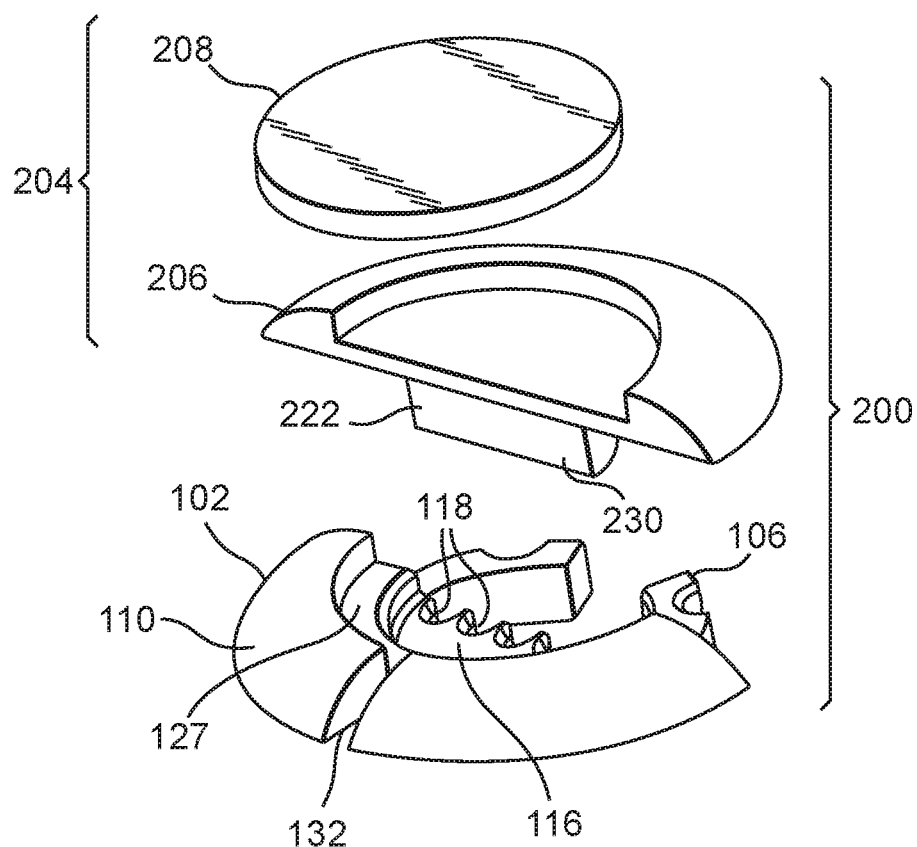
FIG. 6 is an exploded perspective view of a burr hole retention apparatus in accordance with another embodiment of the invention.

FIGS. 6-7 and 8A-8C illustrate a retention apparatus 200 in accordance with another embodiment of the invention. The apparatus 200 is similar in many respects to the apparatus 100 described above. For example, it may include the base 102 described above having, e.g., the lower engagement portion 106, upper flange portion 110, stabilizer portion 116, recess 127, and channel 132. It may further include a cap assembly 204 similar in many respects to the cap member 104. For example, it may include a tab portion 222 and surface 230 substantially similar or identical to the tab portion 122 and surface 130, respectively. However, unlike the cap member 104, the cap assembly 204 may be a two-piece construction. That is, it may include a body 206 and a separate optional cover 208 as shown in FIG. 6.

Figure 7:
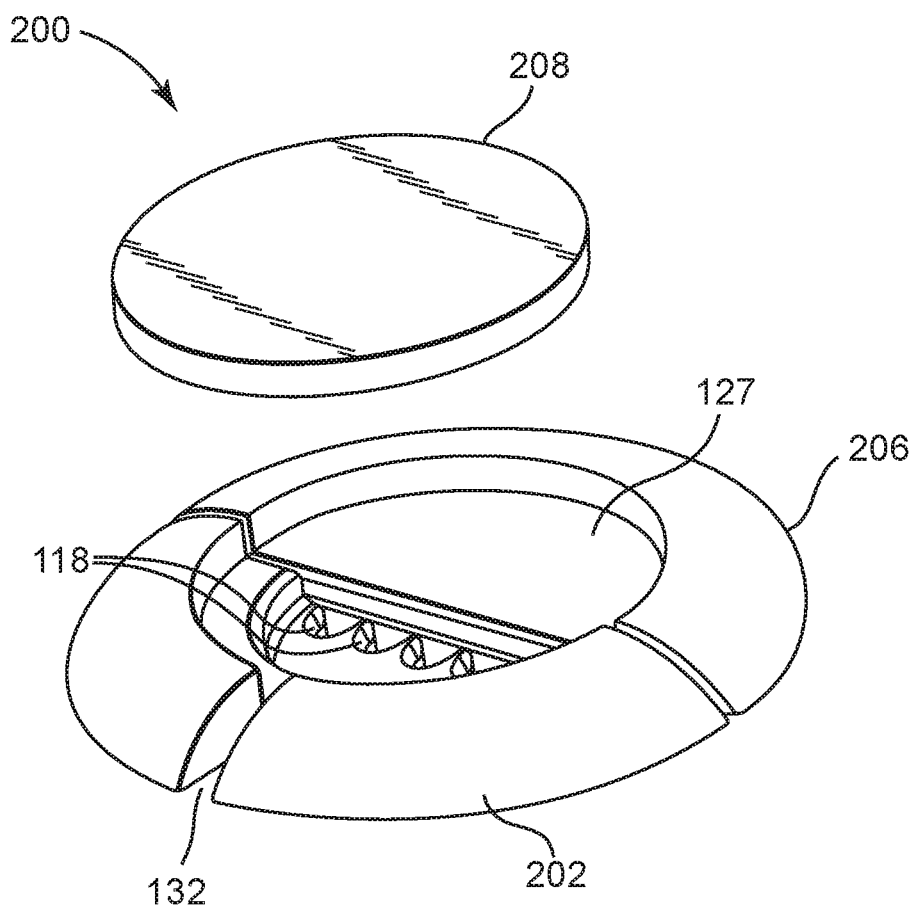
FIG. 7 is a perspective view of apparatus of FIG. 6 as it may be partially assembled.
Figure 8A:
Figure 8B:
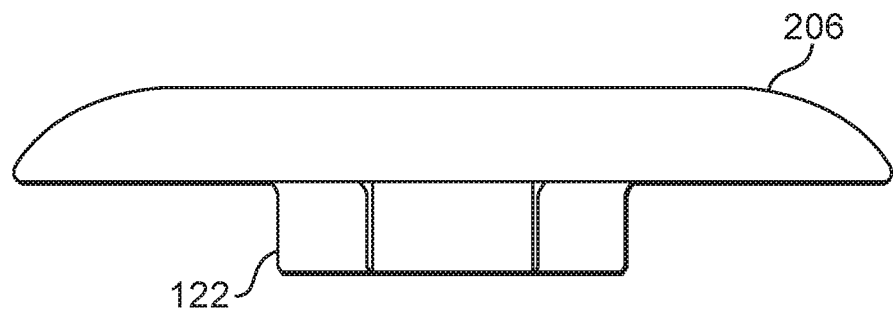
Figure 8C:
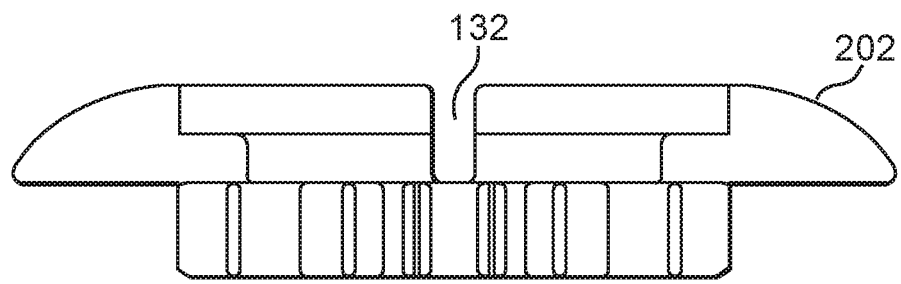

In use, the base 102, as described above, may be located in a burr hole and the catheter 50 secured in one of the notches 118. After the catheter 50 is positioned within a notch 118, the body 206 may be snap-fit into the base 102 as shown in FIG. 7 so that the surface 230 of the tab portion 222 (see FIG. 6) may trap the catheter in place and prevent unintended lateral movement of the catheter out of the notch 118. The catheter 50 may then be placed into the channel 132 in the base 102 as already described above. To complete the assembly, the cover 208 may be snap-fit into the recess 127 (see FIG. 7) to assist in securing the catheter 50 in place. FIGS. 8A-8C illustrate side elevation views of the cover 208, the body 206, and the base 202, respectively.

Figure 9:
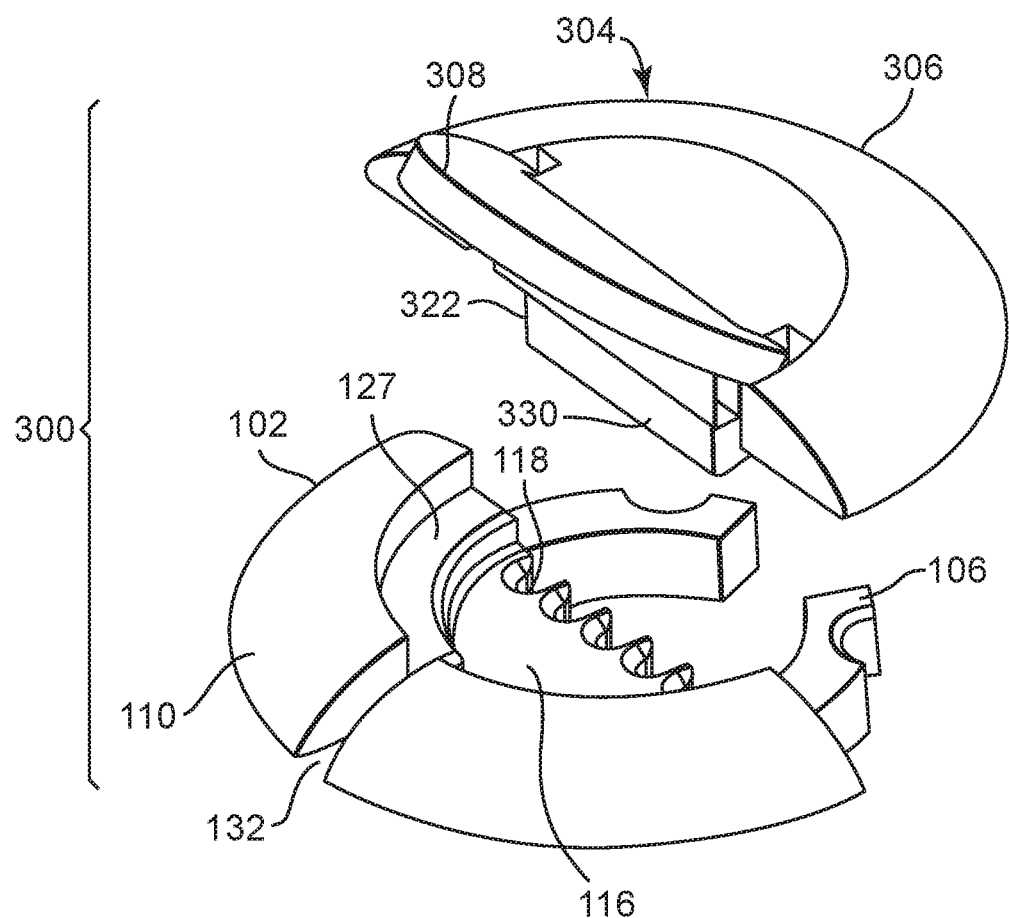
FIG. 9 is an exploded perspective view of a burr hole retention apparatus in accordance with yet another embodiment of the invention.

FIGS. 9-12 illustrate a retention apparatus 300 in accordance with yet another embodiment of the invention. The apparatus 300 is similar in many respects to the apparatus 100 and 200 already described above. For example, it may include the base 102 described above having, e.g., the lower engagement portion 106, upper flange portion 110, stabilizer portion 116, recess 127, and channel 132. It may further include a cap assembly 304 similar in many respects to the cap member 104. For example, it may include a tab portion 322 and surface 330 substantially similar or identical to the tab portion 122 and surface 130, respectively. However, unlike the cap member 104, the cap assembly 304 may include a cover 308 pivotally connected to a body 306 of the cap assembly as shown in FIG. 9.

Figure 10:
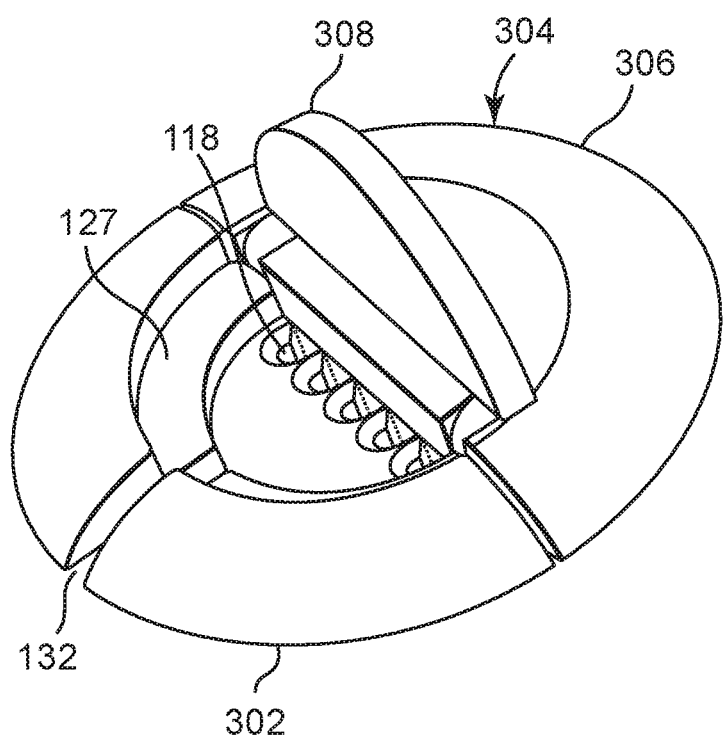
FIG. 10 is a perspective view of the apparatus of FIG. 9 with a cover shown partially open.

In use, the base 102, as described above, may be located in a burr hole and the catheter 50 secured in one of the notches 118. After the catheter 50 is positioned within the notch 118, the body 306 of the cap assembly 304 may be snap-fit into the base 102 as shown in FIG. 10 so that that the surface 330 of the tab portion 322 (see FIG. 9) may prevent unintended lateral movement of the catheter from the notch. After stylet removal, the catheter 50 may be routed through the channel 132 in the base 102. The hinged cover 308 may then be pivoted to the closed position (FIG. 11) and snap-fit into the recess 127 (FIGS. 9 and 10) to assist in securing the catheter in place.

Figure 11:
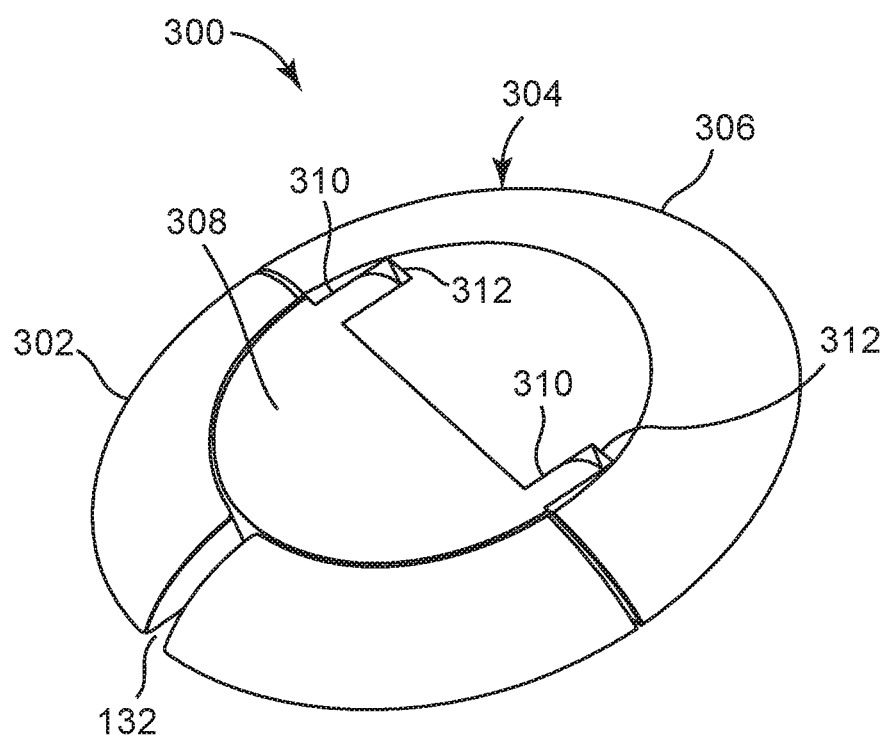
FIG. 11 is a perspective view of the assembled apparatus of FIGS. 9 and 10 with the cover shown closed.

FIG. 11 further illustrates an exemplary configuration for forming the hinge connection between the cover 308 and the body 306 of the cap assembly 304. As illustrated in this view, the cover 308 may include one or more tabs 310 that are each received within a corresponding slot 312 of the body 306 (in place of a slot, the tabs could also be received against outer faces of the body 306). The tabs 310 may include small protrusions (not shown) formed coincident with the hinge line. The protrusions may engage receiving dimples (also not shown) in a sidewall of the slot 312 with a snap fit. As a result, the cover 308 may be pre-assembled with the body 306 in a manner that permits the cover portion to pivot relative thereto.

Figure 12:
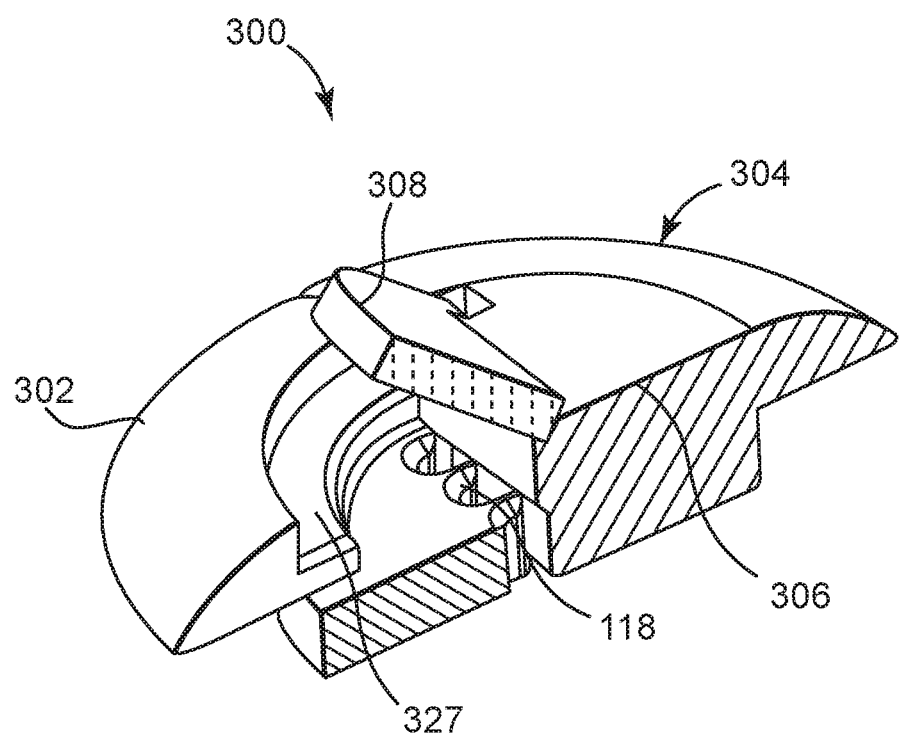
FIG. 12 is a perspective section view of the assembled apparatus of FIGS. 9-11 with the cover shown partially open.

The dimensions of the cover 308 may be selected such that, when the cover is closed as shown in FIG. 11, the base 102 receives it with a snap-fit. FIG. 12 illustrates a perspective, section view of the retention apparatus 300 with the cover 308 shown in a partially open position.

FIGS. 13-19 illustrate a retention apparatus 400 in accordance with still yet another embodiment of the invention. Like some of the preceding embodiments (see, e.g., the apparatus 100), the apparatus 400 may offer the benefit, at the time of use, of a two-piece construction.

Figure 13:
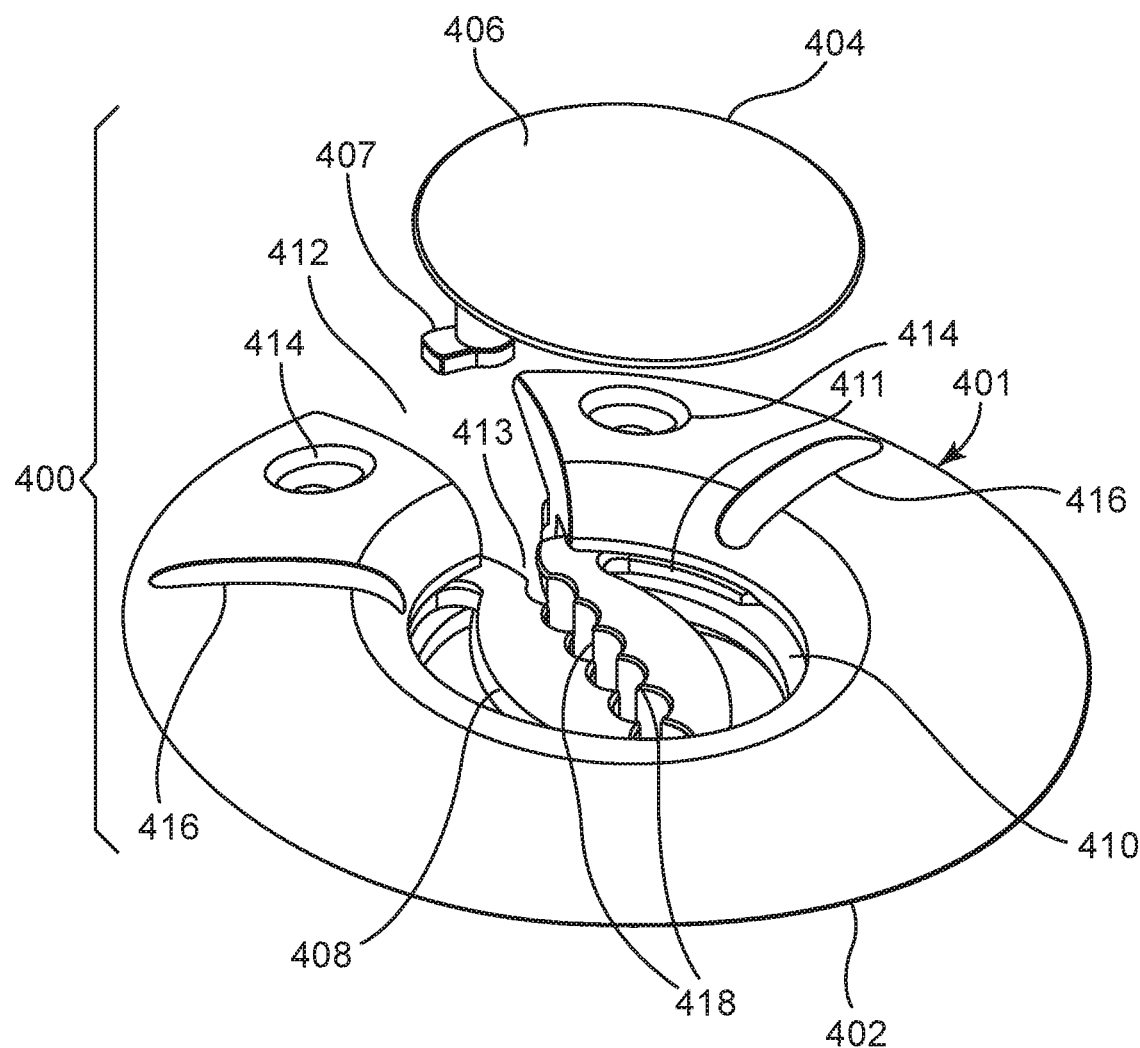
FIG. 13 is a partial exploded perspective view of a burr hole retention apparatus in accordance with still yet another embodiment of the invention.

The apparatus 400 may include a base assembly 401 and an optional cap member 404. The base assembly 401 may include both a base 402 and a stabilizer 408 that may be secured relative the base. In one embodiment, the stabilizer 408 may be positionable within an internal groove 410 formed within a central opening of the base 402 as shown in FIG. 13. The base 402 may further include a flange portion operable to seat against the cranial surface.

The base 402 may form a generally annular, C-shaped ring having a passageway 412 extending outwardly from the central opening through the base. The passageway 412 may be provided to allow compression of the base 402 so that it may be inserted into a burr hole as already described herein. As with the other embodiments described above, the base 402 may include openings 414 defining tool interface surfaces operable to receive forceps or similar tools to allow compression or squeezing of the base during insertion.

The cap member 404 may include a cover portion 406 and one or more protrusions, e.g., tab portions 407. When the cap member 404 is attached to the base 402, the tab portion(s) 407 may interlock with an opening in the base, e.g., with the internal groove 410, thereby securing the cap member as illustrated in FIG. 14.

Figure 14:
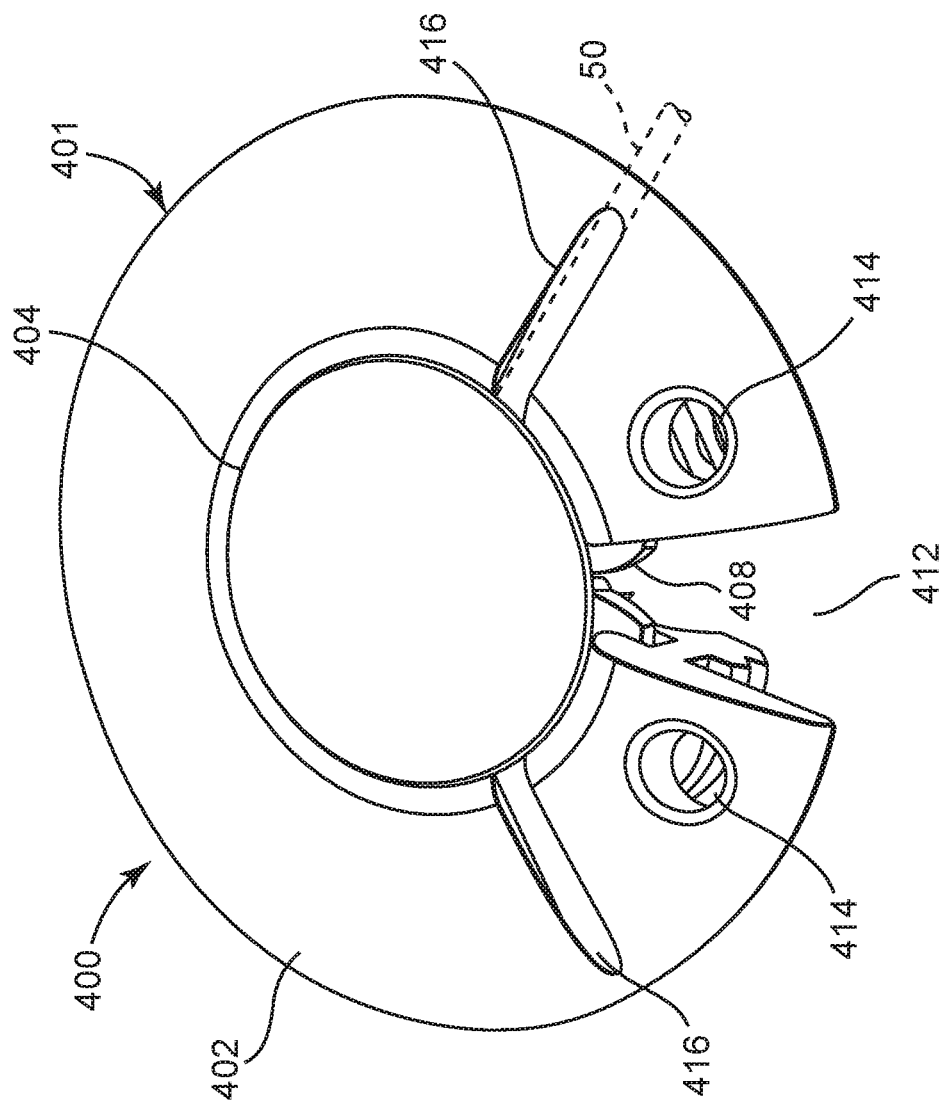
FIG. 14 is perspective view of the apparatus of FIG. 13 as assembled.
Figure 17:
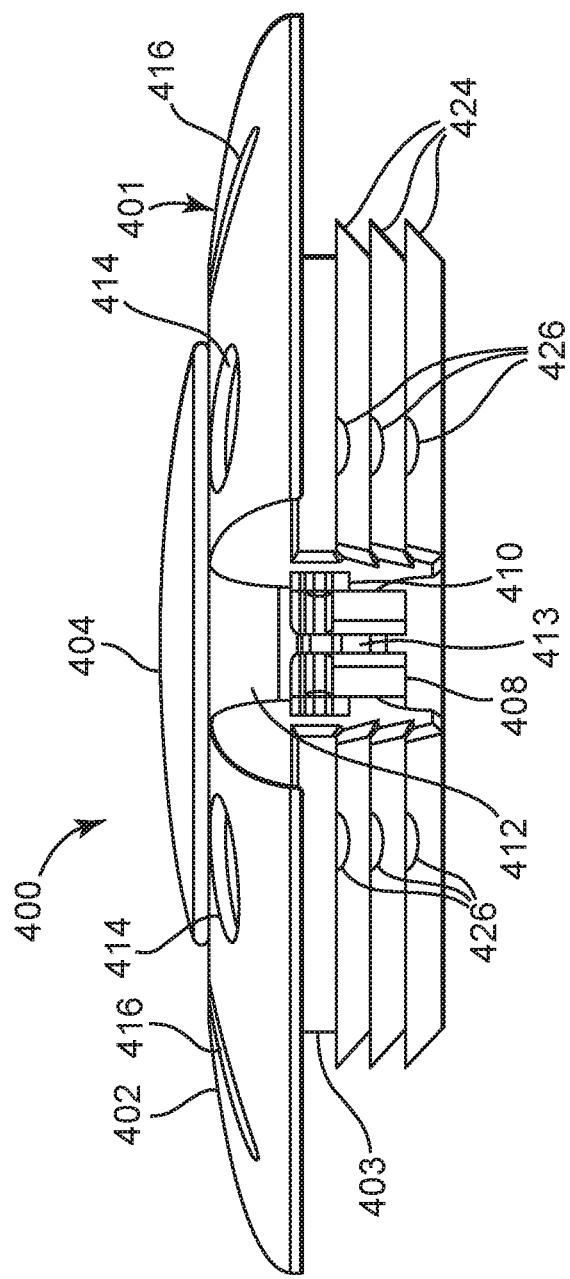
FIG. 17 is a side elevation view of the apparatus of FIG. 13 as assembled.

To permit the catheter 50 to exit the retention apparatus 400, the flange portion of the base 402 may include an upper surface having one or more channels 416 formed therein that are each operable to receive the catheter with an interference fit as represented in FIG. 14. The channel 416 may extend from an inner edge of the flange portion, e.g., from the central opening, outwardly to a point at or near the outer edge (e.g., the channel may terminate short of the outer edge if the curved upper surface of the flange portion tapers to a degree such that the channel breaks out before reaching the outer edge as shown in FIG. 17. Alternatively, the channel may extend to (e.g., through) the outer edge as shown in other embodiments described herein below). The interference fit may be similar to that already described herein, see, e.g., the channel 132/catheter 50 of apparatus 100. While the channel(s) 416 may be shallow as shown in the figures, other embodiments could utilize a deeper channel such as a slot extending completely through the upper flange portion (downwardly through a lower surface of the flange portion). Other embodiments may utilize a non-linear channel as described elsewhere herein with respect to other embodiments.

Figure 15:
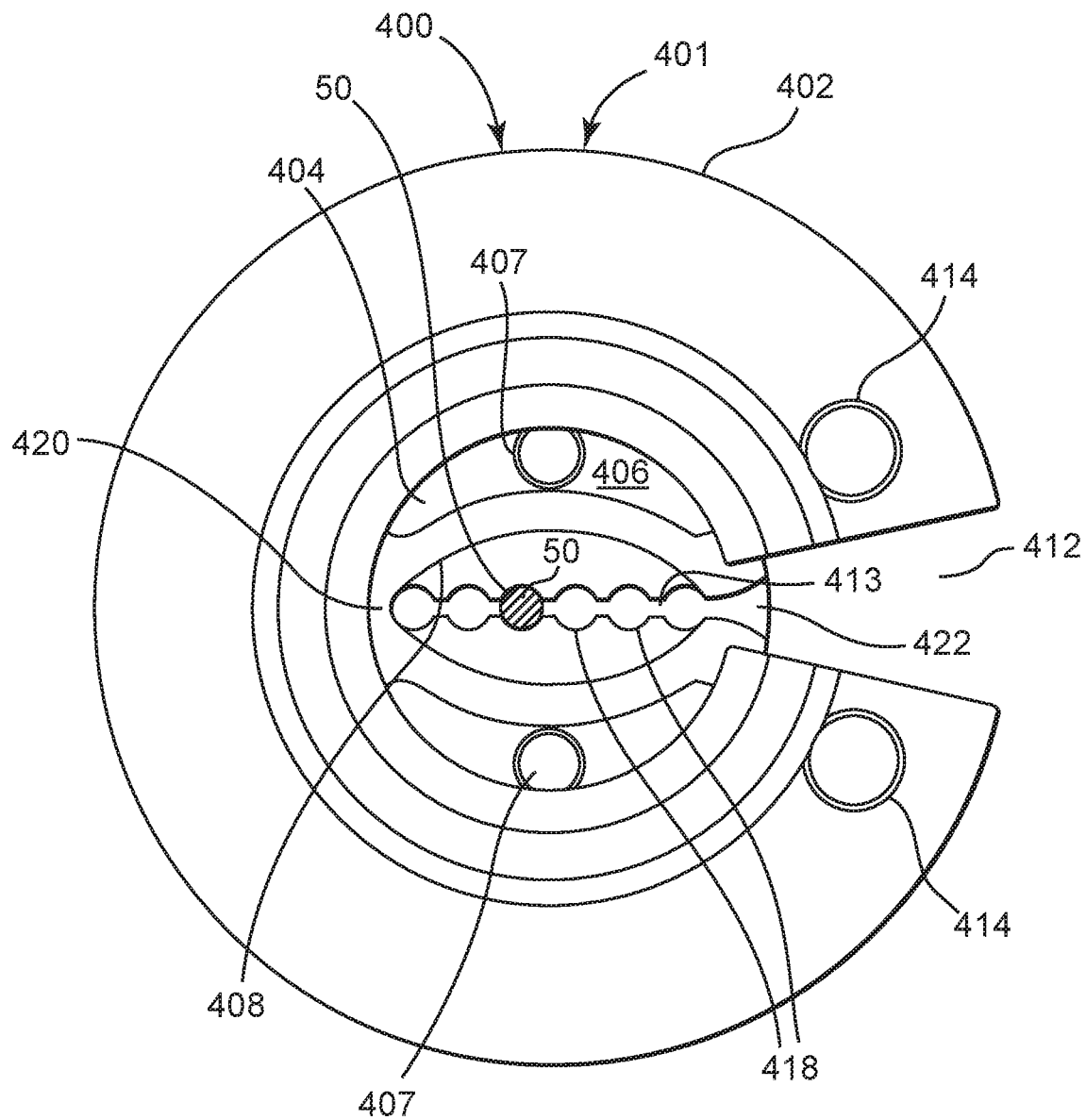
FIG. 15 is a bottom plan view of the apparatus of FIG. 13 as assembled.

The stabilizer 408 may be of most any shape that permits it to secure relative to the base 402. In the illustrated embodiment, the stabilizer 408 is somewhat in the shape of an elongated oval with an end proximate the passageway 412 being open and slightly flared. This provides the stabilizer 408 with an elongate C- or fish-shape as shown in FIG. 15.

The stabilizer 408 may further include a sidewall having a series of open-sided notches or apertures 418 formed therein. In the illustrated embodiment, the stabilizer 408 may include two opposing sidewalls defining a passageway or slot 413 where each sidewall has a series of open-sided notches 418. The slot 413 may extend through an outer edge of the stabilizer 408 when the latter is secured in the base 402.

The notches 418 may each be configured to receive the catheter 50 and anchor it at specific, discrete locations along a length of the sidewall. The interference fit may be similar to the interference fits already described herein, see, e.g., notches 118 of apparatus 100. Like the embodiments described above, the stabilizer 408 may provides numerous notches 418 to allow more flexibility in catheter location within the burr hole. Similarly, as with other embodiments described below, the notches in the slot 413 could be eliminated to provide a generally straight-edged slot.

The stabilizer 408 is preferably made from a flexible material (e.g., plastic) that permits sufficient compression for snap-fit insertion of the stabilizer into the groove 410 of the base 402. One configuration that provides the desired flexibility and resiliency is shown in the Figures, see, e.g., FIG. 15. In this embodiment, the two halves of the stabilizer 408 are joined at a first end 420 while the second end 422 is open to permit side-entry of the catheter 50 into the slot 413. The stabilizer 408 may include ears 411 at the first and second ends 420, 422 (see FIG. 13) operable to engage the groove 410 and hold the stabilizer in place. The base 402 and stabilizer 408 may be assembled prior to, or during, implantation.

While not illustrated, other embodiments may utilize a two-piece stabilizer 408, e.g., one that is not joined at the first end 420. In the case of the latter, the stabilizer halves may be biased towards one another with a spring or other resilient member. The lateral biasing of the two separate halves may be advantageous in some circumstances, e.g., when the catheter 50 is inserted via a large diameter cannula (not shown).

Figure 16:
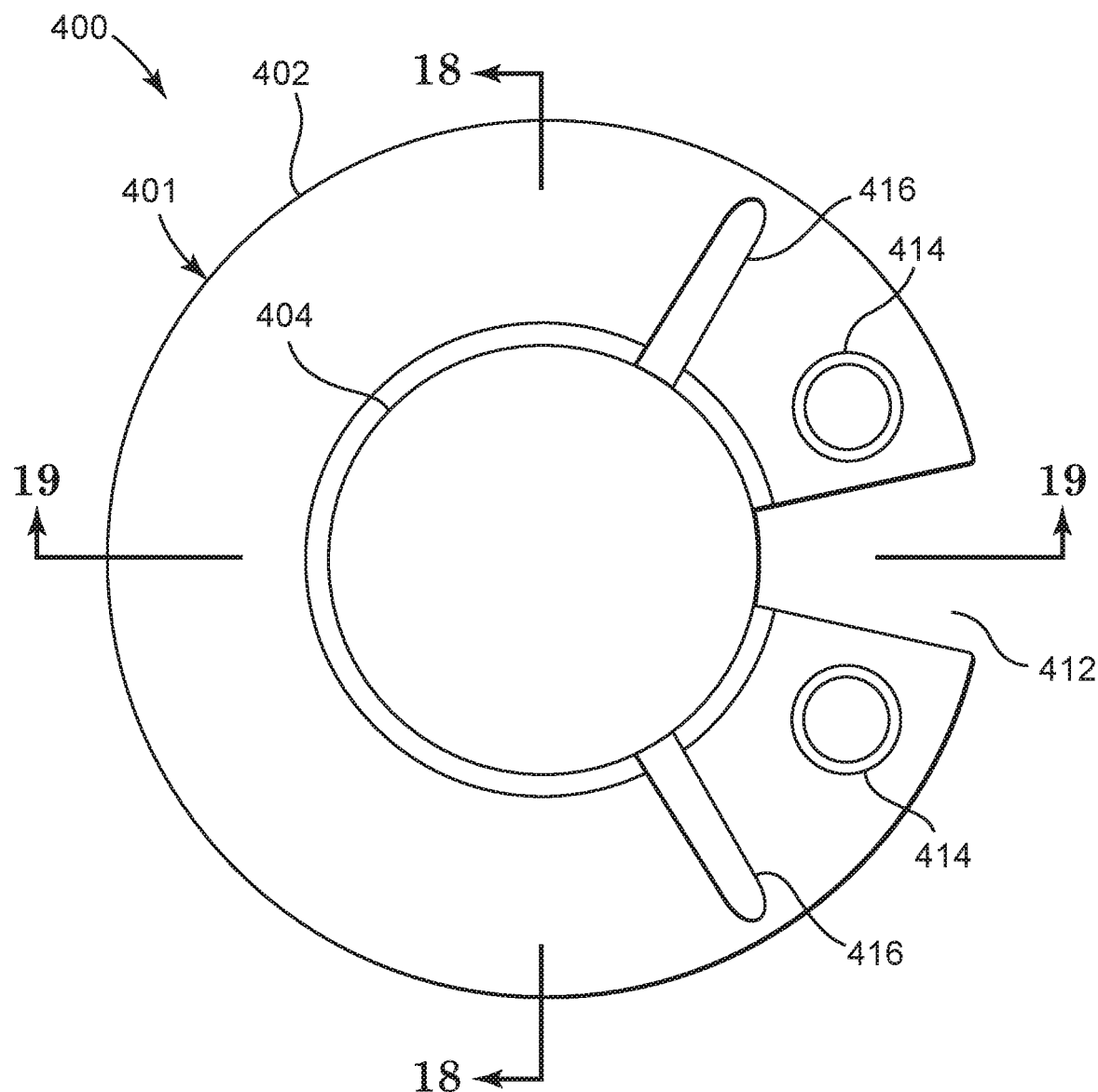
FIG. 16 is a top plan view of the apparatus of FIG. 13 as assembled.

FIG. 16 is a top view of the retention apparatus 400 in its assembled configuration. The slots 416, openings 414, and passageway 412 are clearly visible in this view.

FIG. 17 is a side elevation view of the assembled retention apparatus 400. As clearly illustrated herein, the base 402 may include a lower engagement portion 403 similar in many respects to the lower engagement portion 106 of the retention apparatus 100. The lower engagement portion 403 may include a discontinuous outer surface, e.g., protrusions 424, operable to improve engagement with the inner surface of the burr hole. The protrusions 424 may have cutouts 426 formed therein to ensure clearance for the forceps when the latter are inserted through the openings 414.

Figure 18:
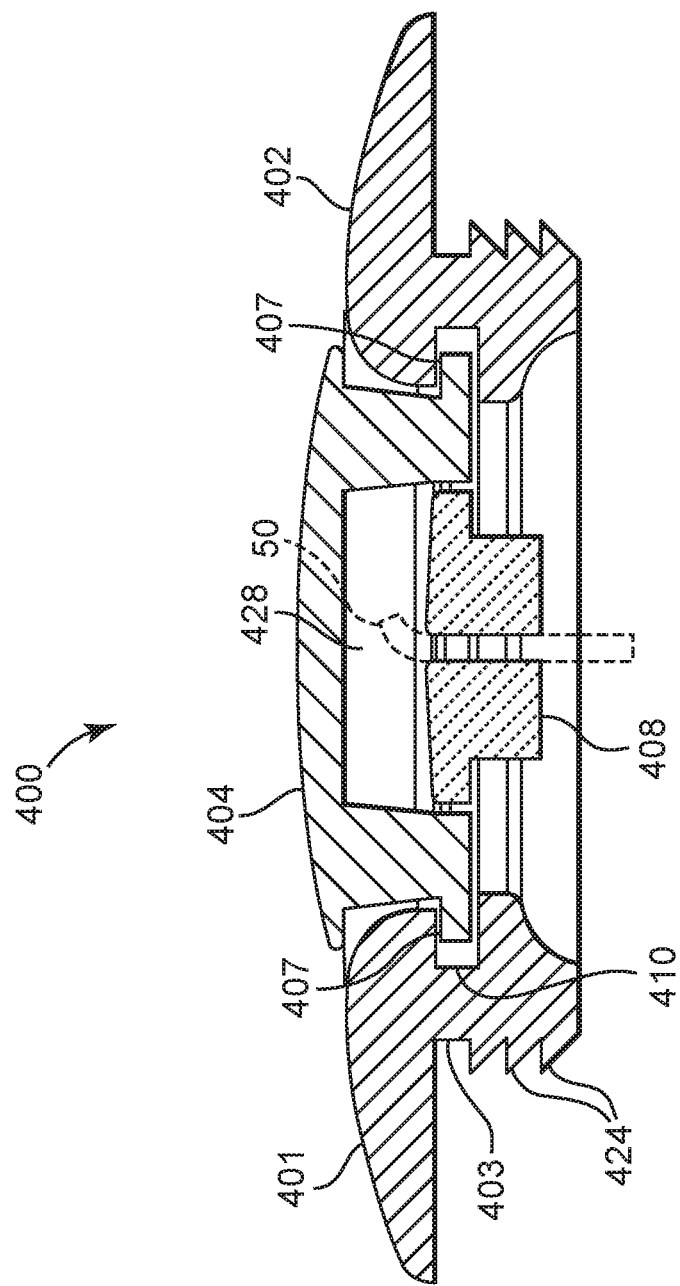
FIG. 18 is a section view taken along line 18-18 of FIG. 16.

FIG. 18 is a cross section of the apparatus 400 taken along line 18-18 of FIG. 16. This view clearly illustrates the interrelation of the tab portion 407 of the cap member 404 with the groove 410. It also shows a void 428 formed between the cap member 404 and the stabilizer 408. The void 428 allows sufficient room for the catheter 50 to transition from the notches 418 to the channels 416 as shown. The channels 416, as illustrated in FIG. 13, may intersect the inner surface of the base 402 at an elevation below the cap member 404 such that the cap member does not pinch the catheter when installed.

Figure 19:
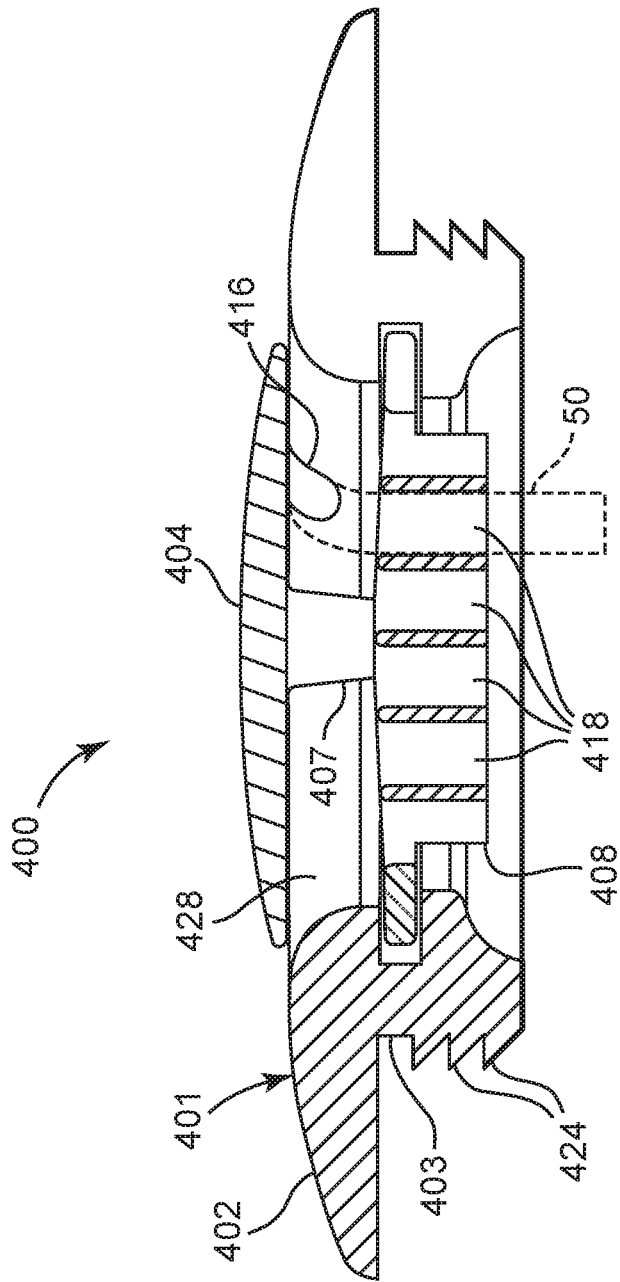
FIG. 19 is a section view taken along line 19-19 of FIG. 16.

FIG. 19 is a cross section of the apparatus 400 taken along line 19-19 of FIG. 16. This view further illustrates the relative positions of the cap member 404, the stabilizer 408, and the channels 416. An exemplary orientation of the catheter 50 is further illustrated in this view.

During implantation of a medical device (e.g., catheter 50), the apparatus 400 functions in much the same way as the previous embodiments. For example, the catheter 50, while implanted through the burr hole and still attached to stereotactic apparatus, may be side-loaded through the passageway 412 of the base assembly 401 and located within the desired notches 418 of the slot 413. Thereafter, the base assembly 401 may be slid longitudinally along the catheter 50 until it reaches the burr hole. Forceps may be used to squeeze or compress the base assembly 401 to insert the same into the burr hole. Once inserted, the catheter 50 may be disconnected from the stereotactic apparatus and the stylet (if used) removed. The catheter 50 may then be routed through one of the channels 416 where it is received with an interference fit. The optional cap member 404 may then be snap fit to the base assembly 401. As a result, the catheter 50 may be secured, via friction, in a first direction (by the notches 418 of the stabilizer 408), and a second direction (by the channel 416).

Figure 20:
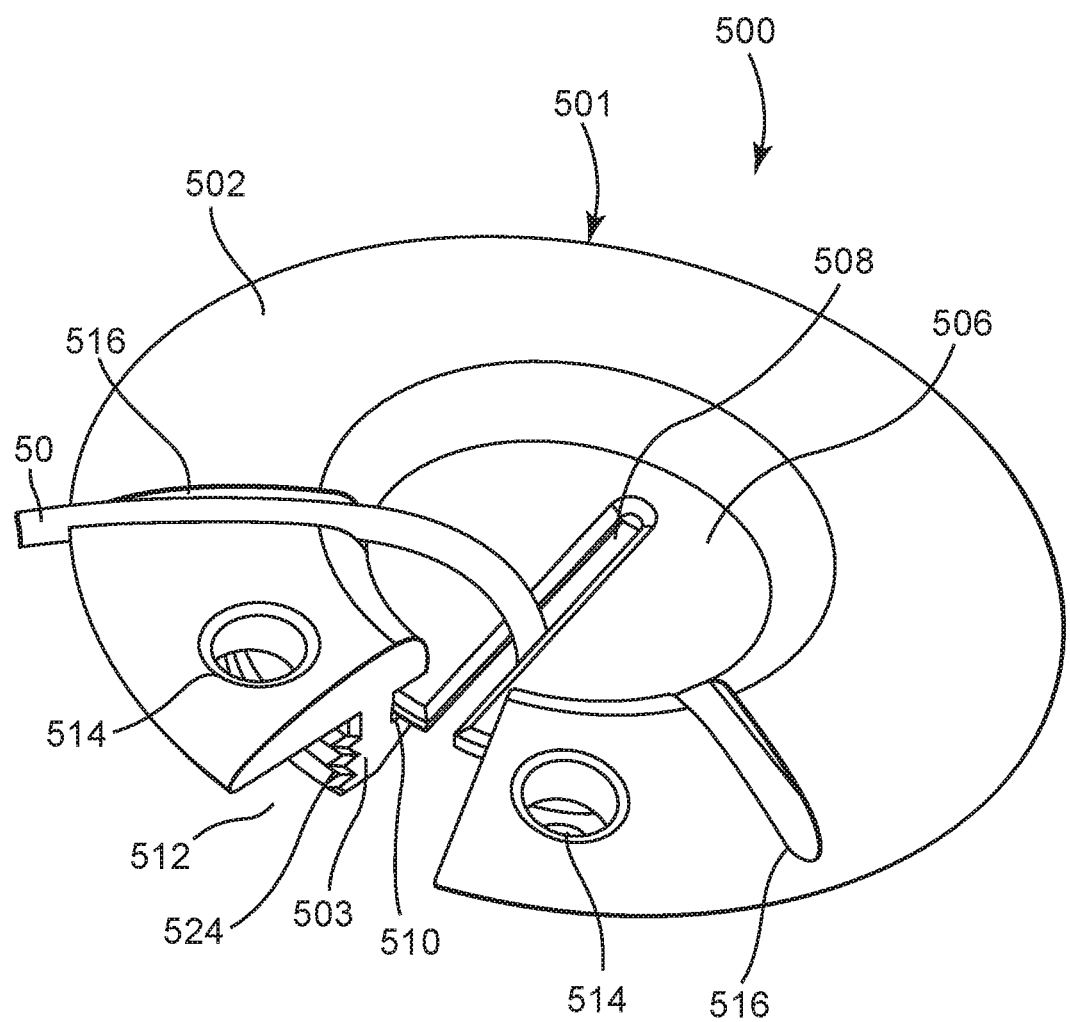
FIG. 20 is a perspective view of a burr hole retention apparatus in accordance with yet another embodiment of the invention.
Figure 21:
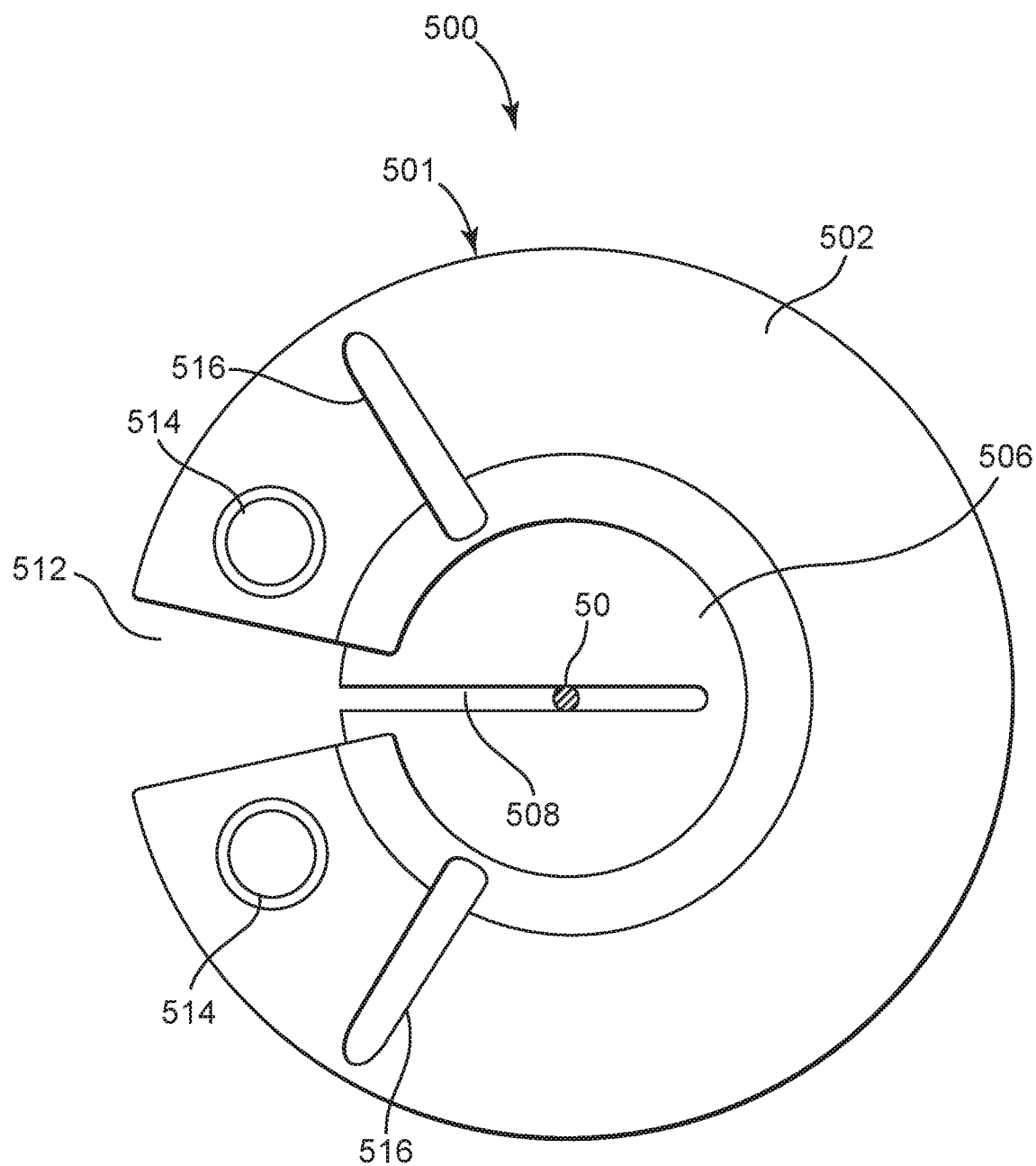
FIG. 21 is a top plan view of the apparatus of FIG. 20.

FIGS. 20-21 illustrate a retention apparatus 500 in accordance with still yet another embodiment of the invention. FIG. 20 illustrates the apparatus in perspective view while FIG. 21 shows a top plan view. The apparatus 500 may include a base assembly 501 incorporating a base 502 and a stabilizer 506. The stabilizer 506 could be pre-assembled with the base 502 prior to implantation, or the stabilizer could be attached to the base during the implantation process. The apparatus 500 could also include a cap member (not shown) similar in many respects to the cap member 404 discussed above.

The base 502 may be identical, or substantially similar, to the base 402 described above with reference to the retention apparatus 400. For example, it may include a lower engagement portion 503 having protrusions 524 located thereon to engage the inner surface of the burr hole, and a peripheral portion, e.g., a flange portion, operable to seat against the cranial surface. The peripheral portion may at least partially surround a central opening in which the stabilizer 506 may secure.

A passageway 512, openings 514, and one or more channels or slots 516, generally identical to the passageway 412, openings 414, and channels 416, respectively, discussed above may also be provided. Like the channels 416, the channel(s) 516 may be formed on the upper surface of the flange portion and may extend from the central opening outwardly to a point at or near the outer edge or of the flange portion. Moreover, each channel 516 may extend partially through a depth of the flange portion, as shown in the figures or, alternatively, form a slot extending entirely through a lower surface of the flange portion. The channels could also be non-linear in shape as described elsewhere herein (see, e.g., channel 616 further described below).

Like the channels described above (see, e.g., channel 416), the channel 516 is preferably configured to have a width equal to or less than an undeflected outer dimension of the catheter. Preferably the width of the channel 516 is less than the outer dimension of the catheter so that the channel may receive the catheter with an interference fit, e.g., an interference fit similar to those fits already described herein.

The retention apparatus 500 may utilize a stabilizer 506 that, in one embodiment, is formed by a flexible disk-shaped member spanning across the central opening of the base 502. The stabilizer 506 may be held in place relative to the base 502 by engagement with an internal circumferential groove 510 formed in the base. While not wishing to be bound to any particular material, the stabilizer 506 may, in one embodiment, be formed of silicone rubber having a durometer of about 50 Shore A to 65 Shore D. Other materials (e.g., polyurethane) may also be used.

The stabilizer 506 may include a series of inner sidewalls wherein two of the inner sidewalls define a radially extending slot 508 (a radial slot passing generally through the center of the stabilizer). While the slot 508 may be of most any shape or configuration, it preferably extends outwardly through an outer edge of the stabilizer 506 when the stabilizer is secured within the central opening of the base. As a result, side entry of the catheter 50 through the passageway 512 and into the slot 508 is permitted as clearly shown in FIGS. 20 and 21. The shape of the slot 508 may also permit it to frictionally receive the catheter 50 at most any location along a length of the slot. Preferably, the slot 508 receives the catheter 50 with an interference fit similar to the interference fits already described herein (see, e.g., notches 118).

In use, the implanted catheter 50, while still coupled to the stereotactic apparatus (see FIG. 1), may be received through the passageway 512 of the base 502 such that the catheter is positioned within the central opening. The base 502 may then be slid longitudinally along the catheter 50 until it reaches the burr hole where it may then be compressed (e.g., using forceps or the like in the openings 514) and placed into the burr hole. The stabilizer 506 may then be positioned proximate the central opening such that the catheter 50 is located in the slot 508. The stabilizer may then be secured in the groove 510 of the base 502 (alternatively, the stabilizer 506 could be secured in the groove 510 prior to implantation of the base 502). The catheter may then be effectively clamped by the sidewalls of the slot 508 at most any location along the length of the slot. The catheter 50 is then disconnected from the stereotactic apparatus and the stylet (if used) removed.

The catheter 50 may then be routed and positioned in one of the channels 516 formed on the upper flange portion of the base 502. As with the other embodiments described herein, the dual interference fits (the catheter 50 with both the slot 508 and the channel 516) provide frictional restraint of the catheter in two separate directions, thereby generally fixing the catheter relative to the base 502. An optional cap member (see, e.g., cap member 404) may be placed over the stabilizer 506 and coupled to the base 502.

Figure 22:
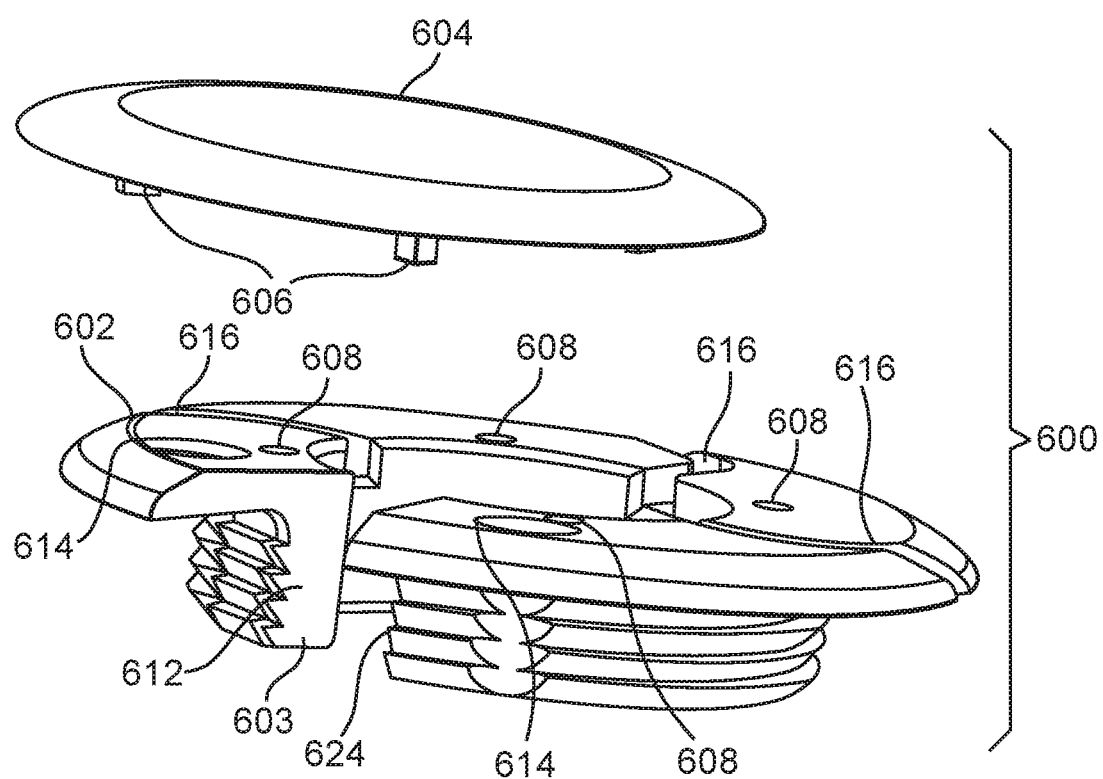
FIG. 22 is an exploded perspective view of a burr hole retention apparatus in accordance with still yet another embodiment of the invention.
Figure 23:
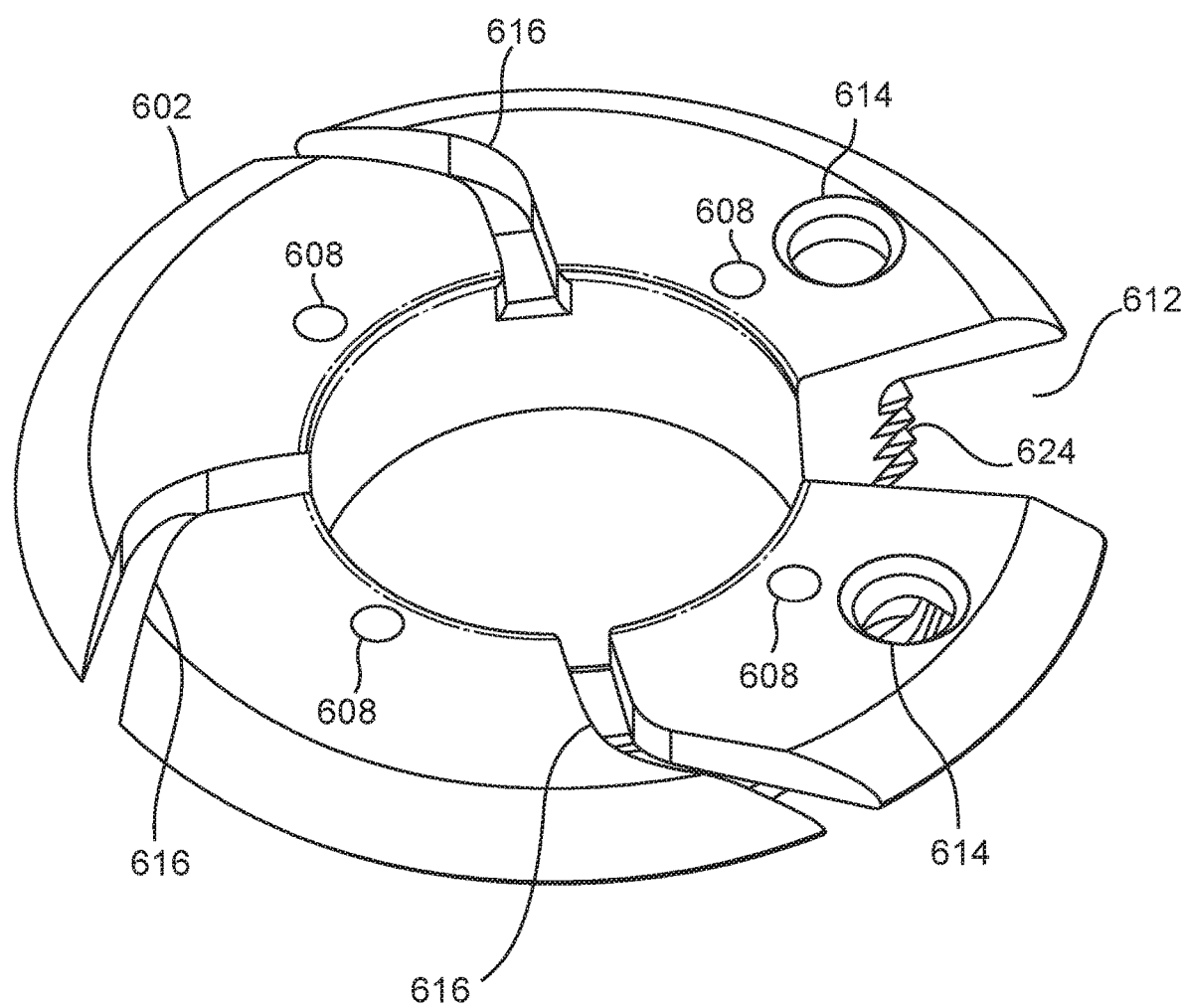
FIG. 23 is a perspective view of a base member of the apparatus of FIG. 22.
Figure 24:
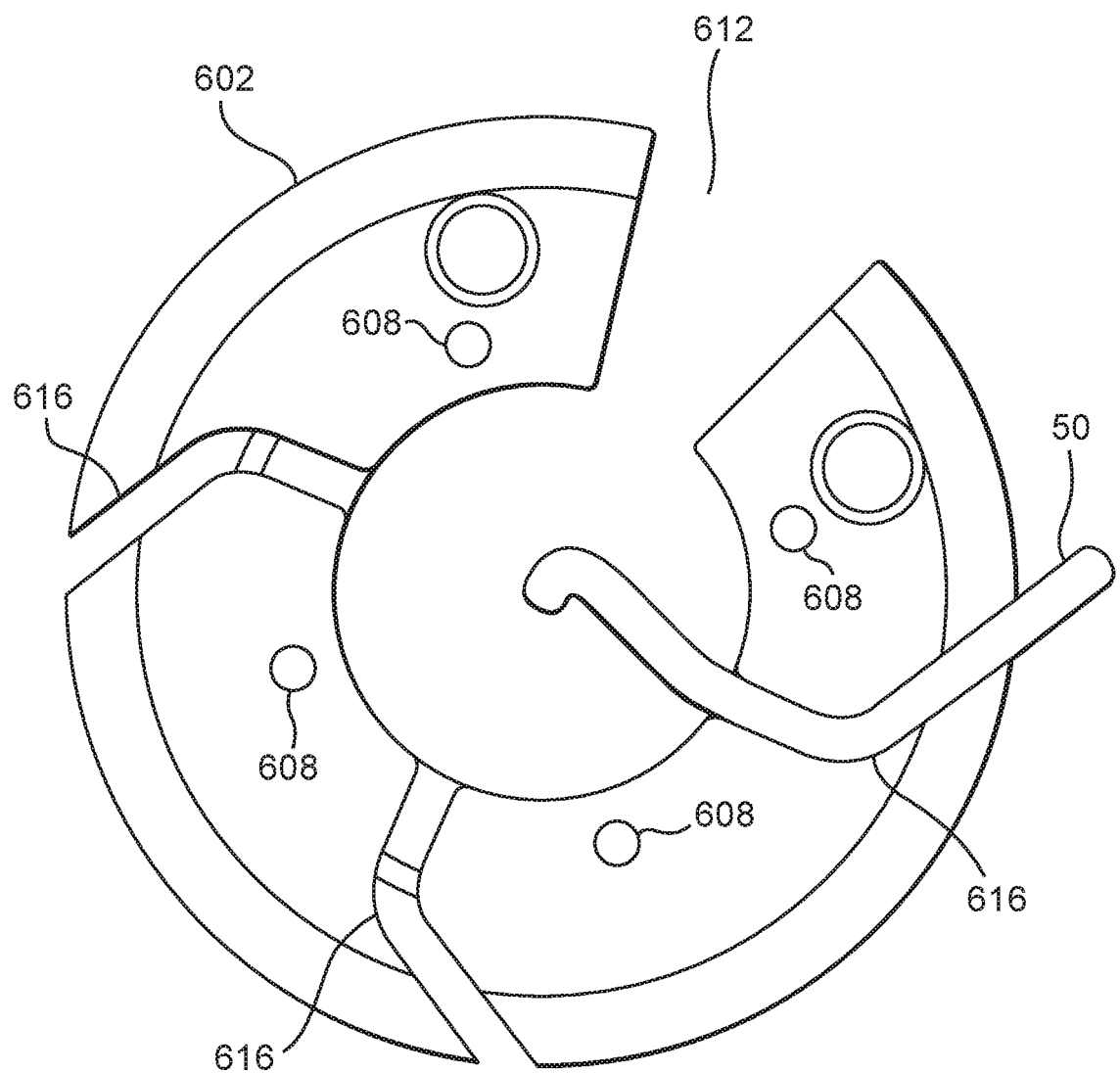
FIG. 24 is a top plan view of the base member of FIG. 23.

FIGS. 22-24 illustrate a retention apparatus 600 in accordance with yet another embodiment of the present invention. As with the other embodiments described herein, the apparatus 600 may include a generally annular C-shaped base 602 having a passageway 612 extending from a central opening outwardly through an outer edge of the base. The base 602 may further include a lower engagement portion 603 with optional protrusions 624 incorporated thereon to assist with securing the base within a burr hole. The base 602 may also include forceps-receiving openings 614 defining tool interface surfaces to assist in compressing the base for insertion into the burr hole.

FIGS. 23 and 24 illustrate an upper surface of a flange portion of the base 602. As illustrated in these views, the upper surface may be traversed by at least one channel 616 operable to receive the catheter 50 with an interference fit as already described herein. The channel 616 may extend from the central opening outwardly through an outermost edge of the flange portion.

Preferably, each channel 616 is circuitous, e.g., non-linear, so that the catheter 50 may be frictionally engaged, within the channel, in at least two non-parallel directions. For example, in the illustrated embodiment, each channel 616 has at least one curved or arc-shaped segment therein to produce the multi-directional frictional forces. However, the illustrated configuration of the channel 616 is not considered limiting as other shapes, e.g., intersecting line segments, are certainly possible without departing from the scope of the invention. Moreover, while some portions of the slots 616 are shown extending entirely through a depth of the flange portion, other embodiments may utilize a more shallow channel configuration.

The apparatus 600 may further include an optional cap member 604 (see FIG. 22). The cap member 604 may include protrusions, e.g., tab portions 606, operable to couple and interlock with openings 608 formed in the surface of the base 602.

Unlike many of the previous embodiments, the apparatus 600 may anchor the catheter 50 without the use of a stabilizer. That is, the apparatus 600 may secure the catheter only via capture within one of the channels 616.

To implant the apparatus 600, the catheter 50, while inserted through the burr hole and still coupled to stereotactic apparatus, may be received through the passageway 612 of the base 602 and positioned within the central opening. The apparatus 600 may then be slid longitudinally along the catheter 50 until it reaches the burr hole. At this point, the base 602 may be compressed, e.g., via forceps in the openings 614, sufficiently to permit insertion in the burr hole. The catheter 50 may then be disconnected from the stereotactic apparatus and the stylet removed. The physician may then route the catheter through the channel 616, wherein it may be received with an interference fit in at least two separate directions, thereby generally fixing the catheter relative to the base 602.

Figures 25A, 25B:
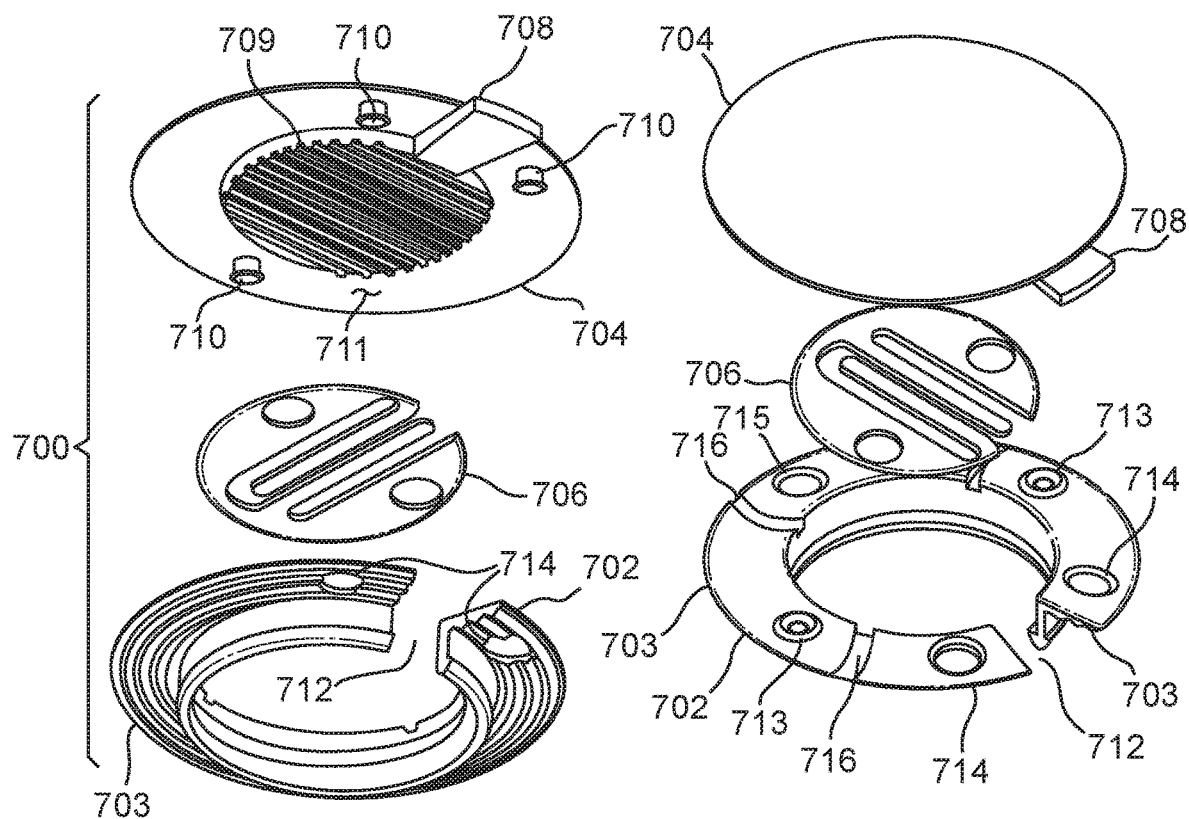

FIGS. 25A and 25B illustrate yet another burr hole retention apparatus 700 in accordance with one embodiment of the invention. In particular, FIGS. 25A and 25B illustrate exploded perspective bottom and top views of the assembly 700, respectively. The apparatus 700, like many of the apparatus described above, may include a base 702, a device stabilizer 706, and an optional cap member 704. As with other components already described herein, the base, stabilizer, and cap may be made of most any biocompatible material including, for example, nylon, polyurethane, polycarbonate, polyamide, and polyetheretherketone (PEEK), or combinations thereof.

Figures 26A, 26B:
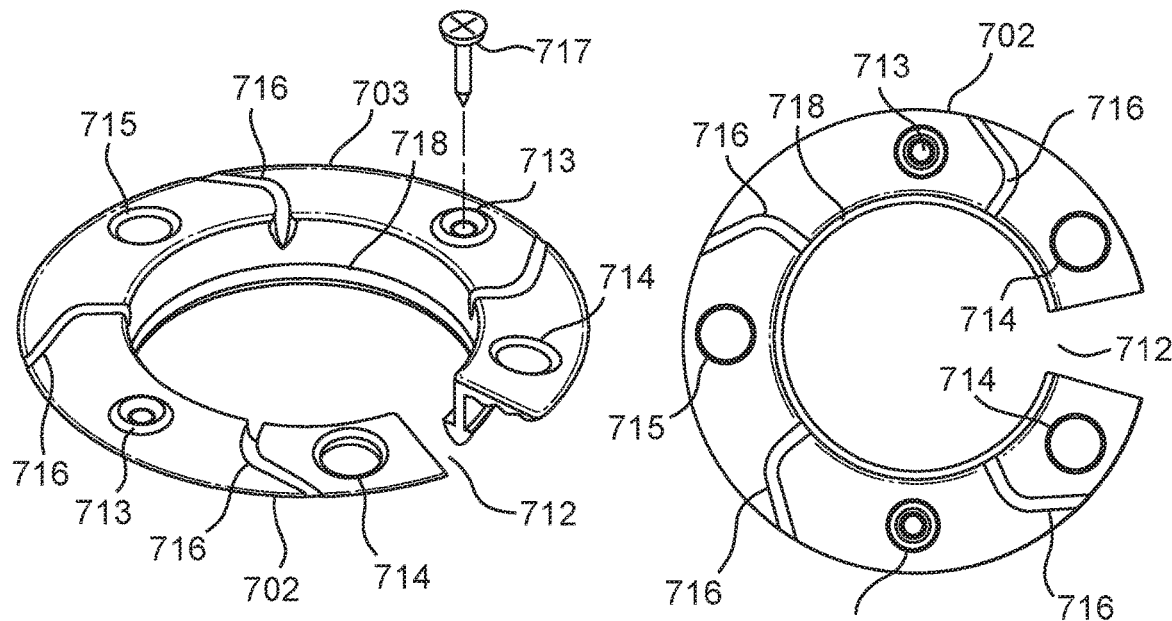

The base 702, shown in more detail in FIGS. 26A and 26B, may sit within the burr hole of the skull. Like the base members described elsewhere herein (see, e.g., bases 402 and 502), the base 702 may form a generally C-shaped ring, e.g., a ring having an opening or passageway 712 extending from a central opening outwardly through its sidewall to an outermost edge. The base 702 may also include an engagement portion for seating against the inner surface or edge of the burr hole, and a peripheral portion defining a flange portion 703. The flange portion 703 and engagement portion may at least partially surround the central opening. The flange portion 703 may further be operable to rest on the surface of the skull when the base 702 is implanted.

As with previous embodiments, the passageway 712 may allow compression of the base 702 to permit insertion of the same into the burr hole. Openings 714 in the flange portion 703 may provide tool interface surfaces for receiving forceps or similar tools to compress the base during insertion into the burr hole. Holes 713 may also be provided to permit attachment of the base 702 to the skull with fasteners 717 (only one shown) as an alternative, or in addition, to the frictional engagement provided by the lower engagement portion.

To permit a catheter (see, e.g., catheter 50 of FIGS. 1 and 3) to exit the retention apparatus 700, the base 702 may further include one or more channels 716 formed on an upper surface of the peripheral portion (e.g., of the flange portion 703). As with other embodiments described herein, the channels 716 may each extend outwardly from the central opening to a point at (e.g., through) or near an outermost edge of the flange portion. The channels 716 may each be operable to receive the catheter with an interference fit. The interference fit may be similar to those already described herein, see, e.g., catheter 50/channel 132 of apparatus 100.

Each channel 716 may be circuitous, e.g., non-linear, so that the catheter 50 may be frictionally engaged in at least two non-parallel directions. For example, in the embodiment illustrated in FIGS. 26A and 26B, each channel 716 has at least two intersecting linear segments to produce the multi-directional frictional forces. Alternatively, in the embodiment illustrated in FIG. 25B, each channel 716 may form a generally continuous curved segment. However, the illustrated shape of the channel 716 is not considered limiting as other shapes are certainly possible without departing from the scope of the invention. As with the previous base members described herein, the channels 716 may extend only partially into the upper surface of the flange portion 703, or may form a slot extending entirely through a lower surface of the flange portion.

The cap member 704 (see FIGS. 25A and 25B), may form a disk-shaped cover having an optional tab portion 708. The cap member 704 is operable to engage or otherwise couple to the base 702 when installed to substantially cover the central opening.

In some embodiments, the cap member 704 may be made from a relatively soft material, e.g., silicone rubber having a durometer of about 55 Shore D to about 65 Shore D. As a result, a lower surface 711 of the cap member 704 may press against the catheter (not shown), providing additional frictional resistance to relative catheter motion. For this reason, the lower surface 711 may include one or more deformable protrusions 709. In other embodiments, the cap member 704 could be made from other materials, e.g., polycarbonate, nylon, or most any biocompatible material.

To accommodate attachment of the cap member 704 to the base 702, the cap member may further include protrusions or standoffs 710 (see FIG. 25A). The standoffs 710 may be received within openings, e.g., openings 714 and 715, formed in the base 702 when the cap member is installed. The standoffs 710 may include an enlarged and deformable distal tip, e.g., may form a mushroom shape at the tip. The mushroom-shaped tip may provide positive engagement, e.g., a snap-fit, of the cap member 704 with the base 702.

The stabilizer 706 may fit within the base 702, e.g., on a lip seat 718 as illustrated in FIGS. 26A and 26B. As with the other embodiments of stabilizers already described herein, the stabilizer 706 may assist in immobilizing the catheter 50 relative to the base 706.

Figure 27:
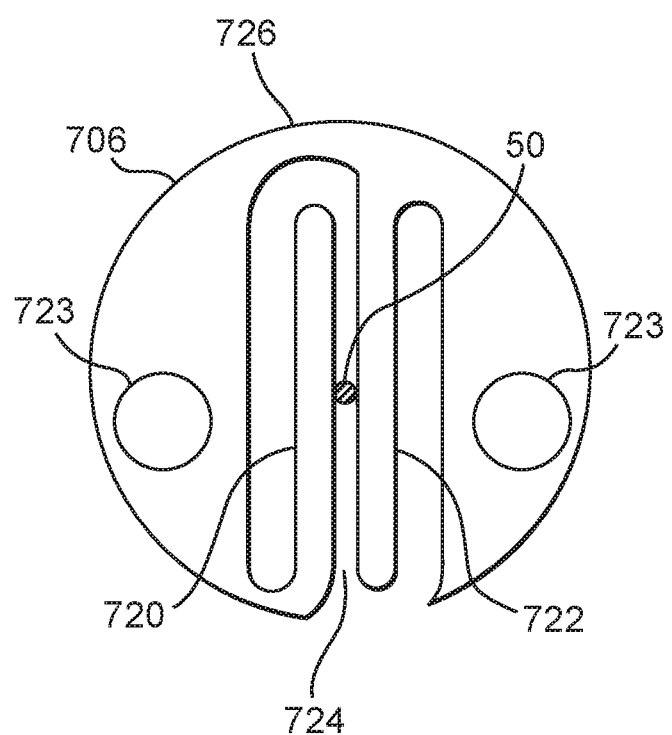
FIG. 27 illustrates a top plan view of a stabilizer or stabilizer member, e.g., catheter stabilizer, in accordance with one embodiment of the invention, the stabilizer operable for use in, for example, the apparatus of FIGS. 25A-25B.

An enlarged plan view of an exemplary stabilizer 706 is shown in FIG. 27. As illustrated in this view, the stabilizer 706 may be a disk-shaped member having an outer edge, and inner sidewalls or surfaces. The inner sidewalls may define a first cantilevered arm 720; and, optionally, a second cantilevered arm 722. Two opposing inner sidewalls or surfaces, e.g., the sidewalls defined by the first and second cantilevered arms, may further define a radially-extending slot 724 extending through the outer edge of the stabilizer when the stabilizer is secured within the central opening. The slot 724 may be operable to frictionally receive and engage the catheter 50 (engage it with an interference fit) at most any location along a length of the slot. Thus, the catheter may be at least partially immobilized at most any location along a length of the slot by a clamping force applied by the first and second cantilevered arms 720, 722.

The arms 720 and 722 may be configured to provide the desired stiffness, and thus the desired clamping force, to the catheter 50. By providing oppositely approaching cantilevered arms 720 and 722, the stiffness of one arm may decrease along the slot length (in a first direction) while the stiffness of the opposing arm increases. Accordingly, acceptable clamping force may be provided over substantially all the length of the slot 724.

Two or more openings 723 may also be formed in the stabilizer 706. The openings may provide tool interface surfaces for manipulating and squeezing the stabilizer 706 during implantation.

While not bound to any specific configuration, the stabilizer 706, in one embodiment, may have an undeflected slot width of about 0.5 mm. With a catheter 50 having an external diameter of about 1 mm, the stabilizer 706 (as with the other stabilizer embodiments described herein) would preferably be configured to apply a clamp load of about 0.1 pounds (lbs) to about 1 lb or more. As with previous embodiments, each channel 716 may also have a width equal to or less than an undeflected outer dimension of the therapy delivery device (e.g., catheter 50) to ensure an interference fit with the base 702 as well.

In some embodiments, one or both of the stabilizer 706 and base 702 may be coated with an adhesive or other friction-enhancing material as further described below.

FIGS. 28A-28D illustrates an exemplary procedure that may be utilized with the retention apparatus described herein, e.g., apparatus 700, to permit implantation of a therapy delivery device (e.g., catheter 50) within a burr hole. After locating the desired cranial entry location, a burr hole 68 may be created in the skull 70 of the patient. Stereotactic apparatus, diagrammatically illustrated at reference numeral 66, may then be utilized to insert the catheter 50 through the burr hole and position it at the desired location within the brain (see FIG. 28A). The stylet 64 may be placed in the catheter 50 prior to insertion to give the catheter 50 rigidity during the implantation process.

Figure 28A:
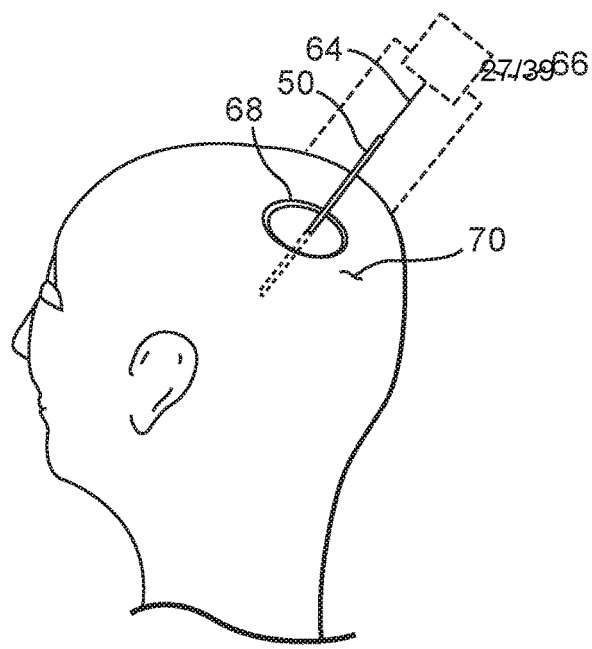
Figure 28B:
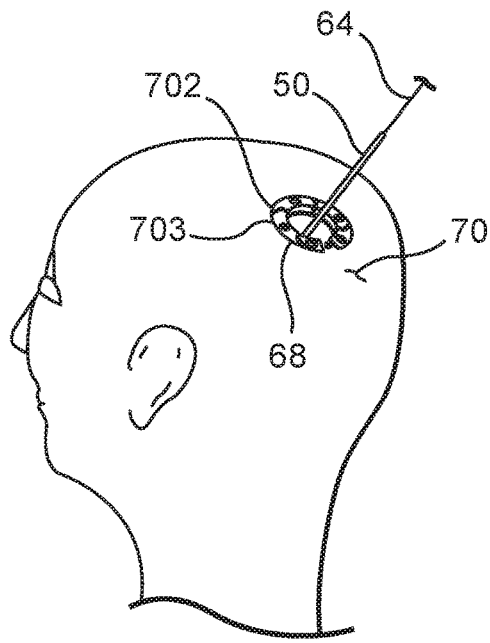

Once the catheter 50 is positioned, the base 702 may be positioned proximate the burr hole and side-loaded over the catheter (the catheter may pass through the passageway 712 of the base 702) until the catheter is located within the central opening of the base. The base 702 may then be moved longitudinally along the catheter 50 towards the burr hole (along the catheter 50). Upon reaching the burr hole 68, the base 702 may be inserted therein as shown in FIG. 28B by, for example, compressing the base with forceps inserted into the openings 714. The base 702 may be inserted until a lower surface of the flange portion 703 contacts a cranial surface, e.g., the skull 70. The base 702 may include protrusions on its lower engagement portion to better secure against the inner surface of the burr hole.

Figure 28C:
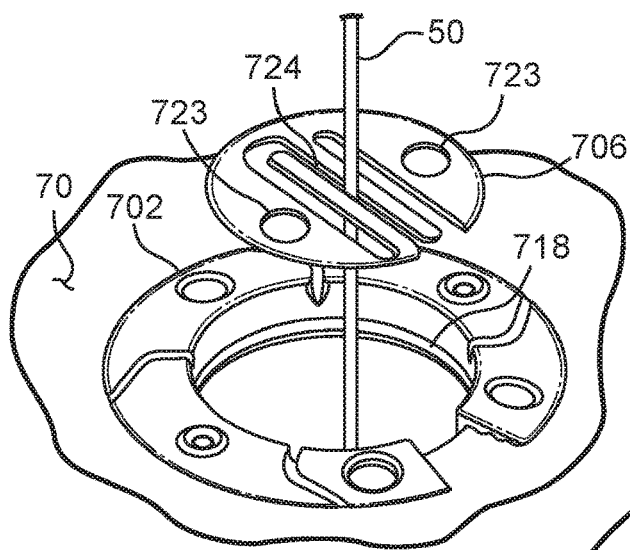

With the base correctly positioned, the catheter 50 may be side-loaded into the slot 724 of the stabilizer 706, preferably while the latter is proximate the base 702 as shown in FIG. 28C. An instrument, e.g., forceps, may be placed into the openings 723 of the stabilizer 706 to squeeze or deform the stabilizer sufficiently to allow it to fit within the central opening of the base 702.

The stabilizer 706 may include one or more thin sections 726 (see FIG. 27) that permit sufficient deflection of the stabilizer with the forceps-applied force. Once the stabilizer 706 is adequately deformed, it may slide into the central opening of the base 702 and seat flush against the lip seat 718 (see FIG. 28C). Upon release of the deflecting force applied to the stabilizer 706, it may expand such that it is securely coupled with interference to the base 702. When the stabilizer 706 is so coupled, the catheter position within the slot 724 may be adjusted as desired. The slot 724 may clamp the catheter 50 in place at most any location along the slot length. Upon verification that the catheter 50 is correctly located, the catheter may be separated from the stereotactic apparatus 66 and stylet 64.

Figure 28D:
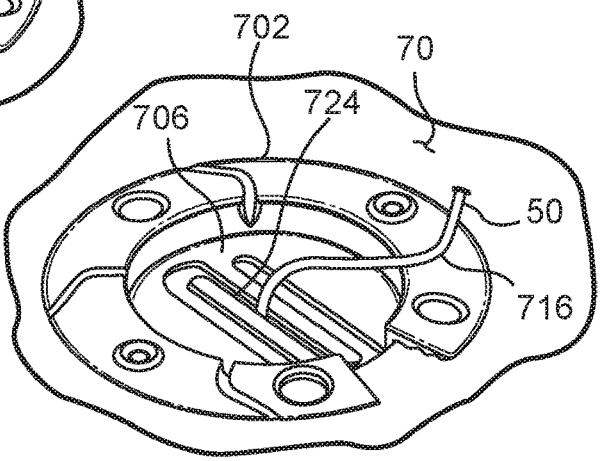

With the stylet removed, the catheter 50 may be routed and placed into one of the channels 716 of the base 702 as shown in FIG. 28D, where it may seat with an interference fit similar to the interference fits already described herein. The cap member 704 may then be coupled to the base 702 by insertion of the standoffs 710 into the openings 714 and 715 (see FIG. 25A).

The interference fits between the catheter 50 and both the channel 716 and the slot 724 of the stabilizer 706 serve to substantially fix the catheter in the desired position relative to the base 702. Moreover, the protrusions 709 of the lower surface 711 of the cap member 704 (see FIG. 25A) may also assist in immobilizing the catheter 50. The tab portion 708 of the cap member 704 may cover the passageway 712 of the base 702, presenting a smooth surface to surrounding tissue. The tab 708 may also be used to pry the cap member 704 from the base to adjust or remove the apparatus.

Figure 29:
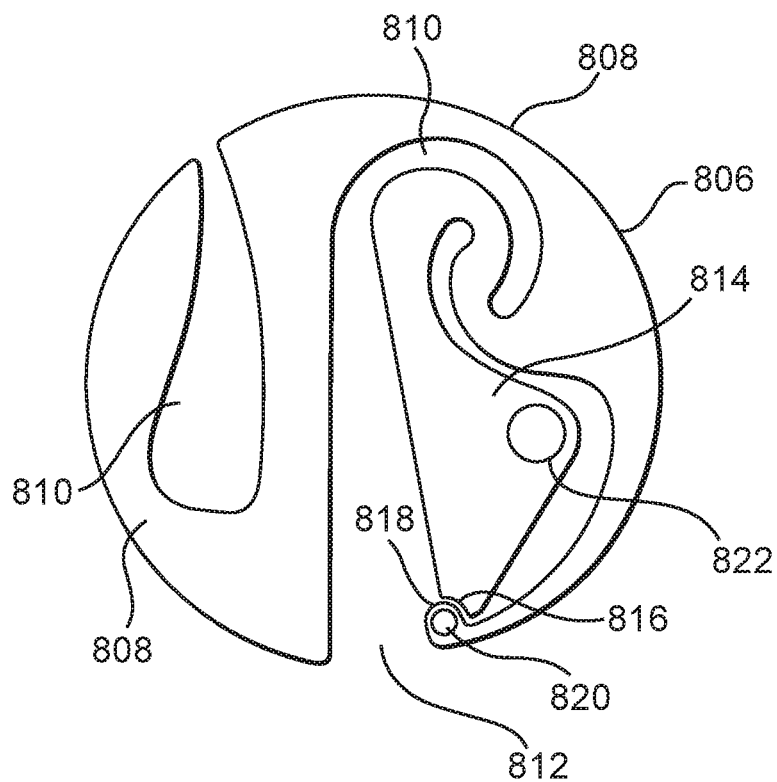
FIG. 29 illustrates a top plan view of a catheter stabilizer in accordance with another embodiment of the invention, wherein an arm of the stabilizer is in a second position.
Figure 30:
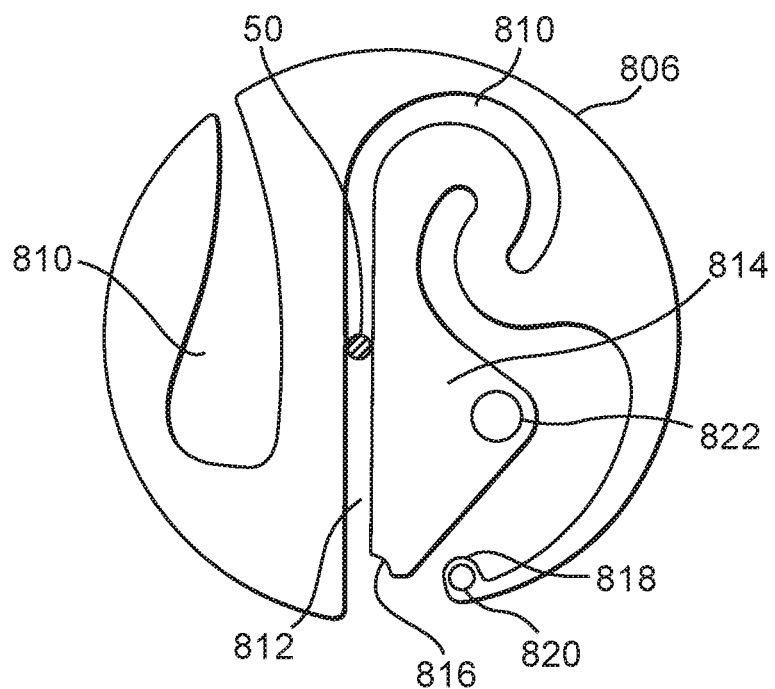
FIG. 30 illustrates the stabilizer of FIG. 29, wherein the arm is in a first position.

FIGS. 29 and 30 illustrate a stabilizer 806 in accordance with another embodiment of the present invention. The stabilizer 806 may replace the stabilizer 706 in the retention apparatus 700 described above and illustrated in FIGS. 25A-25B. That is, the stabilizer 806 may be used with the base 702 and cap member 704 described above.

As with the stabilizer 706, the stabilizer 806 may form a resilient disk-shaped member having a peripheral or outer edge and inner surfaces or sidewalls. The stabilizer 806 may be configured such that it may couple to the base 702, e.g., snap-fit within the central opening, and rest against the lip seat 718 (see FIG. 26A).

To provide the stabilizer 806 with sufficient flexibility, the inner surfaces may define cutouts 810 that define one or more thin sections 808. The cutouts 810 may further define tool interface surfaces for manipulation (e.g., compression) of the stabilizer 806. Some of the inner surfaces may further define a slot 812 extending through the peripheral edge of the stabilizer 706.

A first inner surface forming the slot 812 may be defined by a movable arm 814. However, unlike the dual cantilevered arms of the stabilizer 706 of FIG. 27, the stabilizer 806 may include a single cantilevered arm 814 that may be moved from a first position (shown in FIG. 30), to a second position (shown in FIG. 29). In the first position of FIG. 30, the movable arm may press the catheter 50 against a second inner surface at most any location along a length of the slot. In the second position of FIG. 29, the distance between the first and second inner surfaces may be greater than when the movable arm 814 is in the first position to better allow entry and positioning of the catheter 50. In the illustrated embodiment, the second inner surface may be formed by a generally fixed surface of the stabilizer 806.

The stabilizer 806 may also include a lock portion that permits locking the movable arm 814 in the second position. For example, a cantilevered end of the arm 814 may include a recess 816 (see FIG. 30) operable to engage a tab 818 of the stabilizer 806 when the arm is deflected.

The tab 818 may further include an opening or depression 820 for receiving a tool to assist in releasing the arm 814 from the second position at the appropriate time. The stabilizer 806 may also include one or more openings 822 defining other tool interface surfaces operable to receive forceps or the like. The openings 822 may be used to manipulate the stabilizer during implantation.

To utilize the stabilizer 806, a procedure similar to that described above with respect to the apparatus 700 may be used. The implantation procedure is substantially similar to that described above with reference to FIGS. 28A-28D and, as such, reference to those figures is made.

Once the base 702 is correctly positioned in the burr hole (see FIG. 28B), the catheter 50 (which may also be located in the burr hole) may be side-loaded into the slot 812 of the stabilizer 806 while the latter is located in or near the central opening. The stabilizer 806 may preferably be configured in its second position as illustrated in FIG. 29 during catheter insertion. An instrument, e.g., forceps, may be placed into the opening 822 and the opposing cutout 810 of the stabilizer 806 to squeeze or deform the stabilizer sufficiently to fit within the central opening of the base 702. The thin sections 808 may permit sufficient deflection of the stabilizer 806 to accomplish placement with the forceps-applied force.

With the stabilizer 806 adequately deformed, it may be placed into the base 702 where it may secure, e.g., with interference, relative to the base and seat against the lip seat 718 (see FIGS. 26A and 26B) when the forceps-applied force is released. An instrument, e.g., forceps, may then be placed into the depression 820 and at another location on the stabilizer and a separating force applied. When the separating force applied is sufficient to displace the tab 818 relative to the recess 816, the arm 814 may be unlocked from its second position, whereupon it may be biased towards its first position as shown in FIG. 30.

In the undeflected position, the arm 814 applies a slight clamping force (interference fit) to the catheter 50 to clamp or immobilize the latter between the first inner surface of the movable arm 814 and the second inner surface at most any location along a length of the slot 812. Upon verification that the catheter 50 is in place, the catheter may be removed from the stereotactic apparatus and the stylet may be withdrawn from the catheter. The catheter may then be placed into one of the channels 716 of the base 702, and the cap member 704 coupled to the base as described above.

FIGS. 31, 32A-32B, and 33 illustrate a stabilizer 906 in accordance with yet another embodiment of the present invention. Once again, the stabilizer 906 may replace the stabilizer 706 (see, e.g., FIGS. 25A and 25B) within the retention apparatus 700, e.g., may couple to the base 702.

Figure 33:
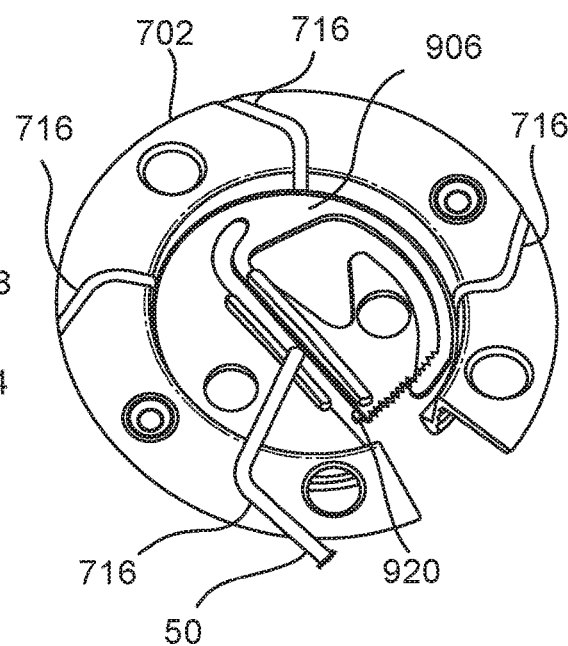
FIG. 33 is a perspective view of the stabilizer of FIGS. 32A-32B as it may be positioned in the base member of FIGS. 26A-26B.

The stabilizer 906, like the stabilizers 706 and 806 discussed above, may form a resilient disk-shaped component that may be deflected or compressed sufficiently to fit within the central opening of the base 702 and rest against the lips seat 718 (see FIGS. 26A and 26B) as shown in FIG. 33.

The stabilizer 906 may be defined by a peripheral edge and inner surfaces. A first inner surface 913 may be located on an arm 914 that is movable relative to an opposing second inner surface 915. The first and second inner surfaces may define a slot 912 operable to receive the catheter 50 with an interference fit at substantially any location along a length of the slot as shown in FIGS. 32A and 33. To provide the stabilizer 906 with sufficient flexibility, it may also include one or more thin sections 908. In one embodiment, the thin section 908 is formed by various cutouts 910.

Figure 31:
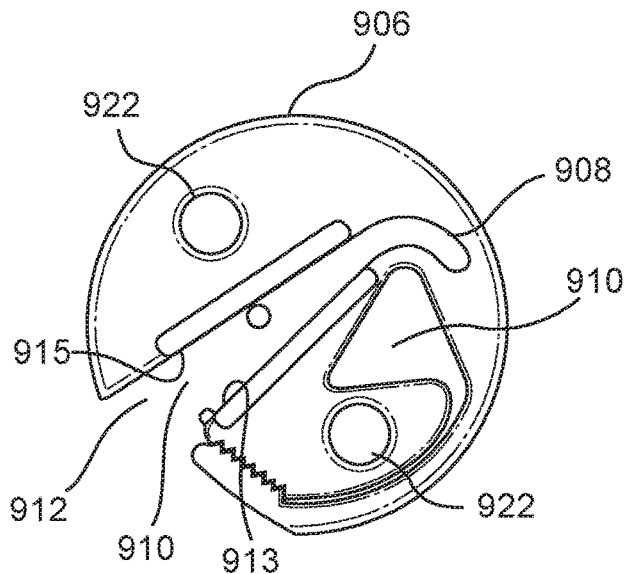
FIG. 31 illustrates a plan view of a catheter stabilizer in accordance with yet another embodiment of the invention, wherein an arm of the stabilizer is in a second position.

Unlike the dual cantilevered arms of the stabilizer 706 of FIG. 27, the stabilizer 906 may include the single arm 914 that may be moved between a first position (shown in FIGS. 32A, 32B, and 33) and a second position (shown in FIG. 31). The stabilizer 906 may also include features that permit locking the arm 914 in the first position. For example, the arm 914 may include a series of first teeth or serrations 916 operable to engage a one or more second teeth or serrations 918 located on a mating portion of the stabilizer 906 as shown in FIG. 32A. As a result, the arm 914 may be locked in the first position of FIGS. 32A-32B and 33. Additionally, the arm 914 may be locked in the second position of FIG. 31, or at most any position between the first position and the second position.

Figure 32B:
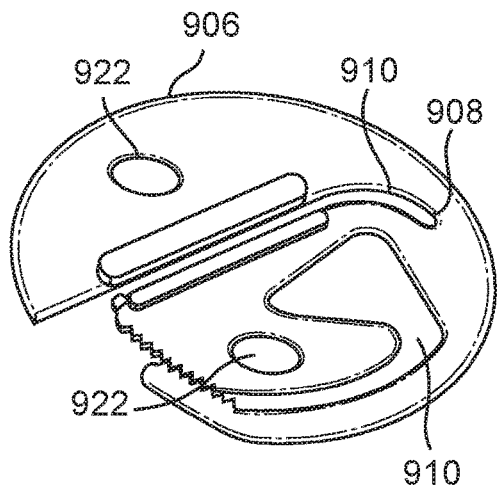
Figure 32A:
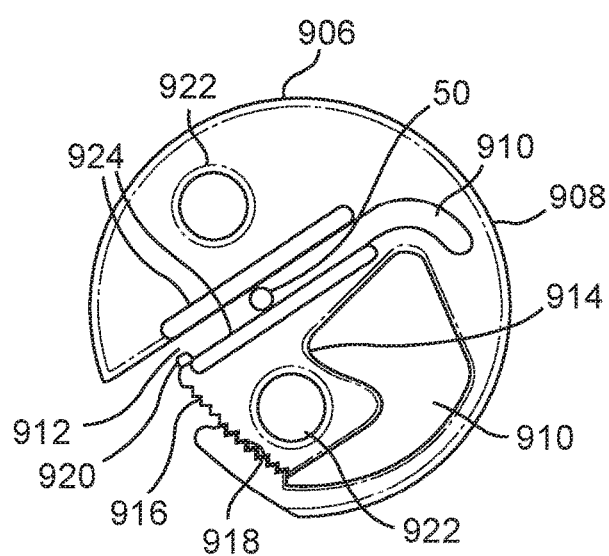

When locked in the first position of FIGS. 32A-32B and 33, the arm 914 may position the inner surface 913 such that it is substantially parallel to the opposing inner surface 915. The stabilizer 906 may also include a stop member 920 to assist in limiting the location of the arm 914 (the first inner surface 913) when the arm is in the first position, e.g., to prevent clamping too tightly against the catheter 50. When the movable arm 914 is in the second position, a distance between the surfaces 913 and 915 may be greater than when the arm is in the first position to assist in locating and securing the catheter 50. As with the other stabilizers described above, the stabilizer 906 may also include one or more openings 922 defining tool interface surfaces operable to receive forceps for manipulation of the stabilizer during implantation.

To utilize the stabilizer 906, a procedure similar to that described above with respect to the apparatus 700 of FIGS. 28A-28D may be used, e.g., the base 702 may be installed as described above in FIG. 28A. Once the base 702 is correctly positioned, the catheter 50 may be side-loaded into the slot 912 of the stabilizer 906 while the latter is proximate the central opening of the base. To facilitate catheter loading, the stabilizer 906 may preferably be configured in the second position illustrated in FIG. 31. The stabilizer 906 may then be pushed into the central opening of the base 702 until it securely seats (e.g., with interference) in the base against the lip seat 718 (see FIGS. 26A-26B). An instrument, e.g., forceps, may be placed into the openings 922 to then draw the first inner surface 913 of the arm 914 towards the second inner surface 915 to close the slot 912 and engage the catheter 50. Continued squeezing may result in the application of a slight squeezing or clamping load applied to the catheter 50. The teeth 916 and 918 permit locking of the movable arm 914 in the desired position.

The stop member 920 may be configured to permit the physician to squeeze the forceps until the stop member 920 contacts the second inner surface 915 of the slot 912, resulting in a known slot width and thus a known interference fit. Alternatively, the physician may utilize other feedback to determine catheter clamp load. In some embodiments, the edges of the slot 912 may include raised portions 924 that provide various benefits including, for example, assisting the physician in maintaining the desired bend radius on the catheter 50, and providing opposing tool interface surfaces (e.g., for forceps) that permit moving the arm 914 between the first position and the second position.

Upon verification that the catheter 50 is in its desired location, the catheter 50 may be removed from the stereotactic apparatus 66 and the stylet may be withdrawn from the catheter. The catheter 50 may then be placed into one of the slots 716 of the base 702 as shown in FIG. 33. The cap member 704 (see FIGS. 25A and 25B) may then be optionally coupled to the base 702 as already described above.

Figure 34:
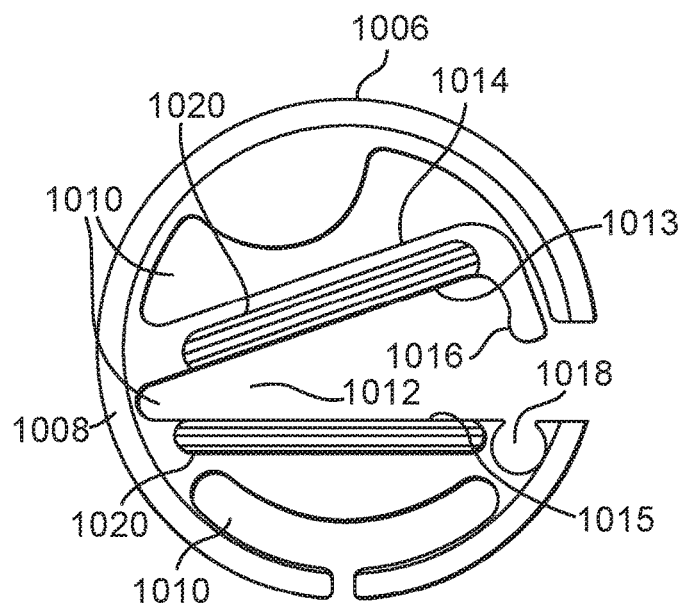
FIG. 34 illustrates a top plan view of a stabilizer in accordance with still another embodiment of the invention, wherein an arm of the stabilizer is shown in a second position.
Figure 35:
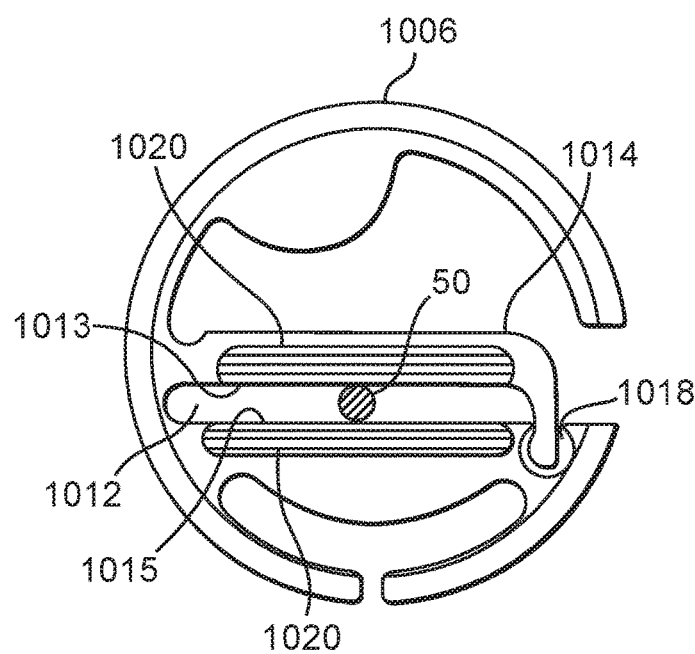
FIG. 35 is a top plan view of the stabilizer of FIG. 34, wherein the arm is in a first position.
Figure 36:
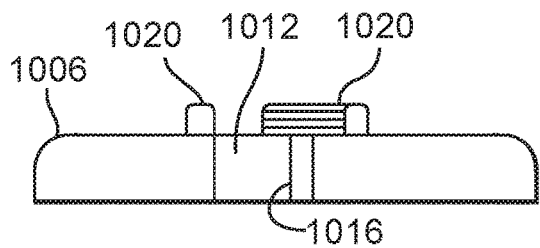
FIG. 36 is a side elevation view of the stabilizer of FIGS. 34-35, wherein the arm is in the second position.

FIGS. 34-36 illustrate a stabilizer 1006 in accordance with still yet another embodiment of the present invention. As with other stabilizers discussed above (see, e.g., stabilizers 806 and 906), the stabilizer 1006 may replace the stabilizer 706 (of FIGS. 25A and 25B) within the retention apparatus 700. That is, the stabilizer 1006 may be used with the base 702 and cap member 704 already described herein.

The stabilizer 1006 may form a resilient disk-shaped member that deforms or compresses sufficiently to fit, e.g., with interference, into the central opening of the base 702, where it may eventually rest against the lip seat 718 (see FIG. 26A).

The stabilizer 1006 may be defined by a peripheral edge and inner surfaces. A first inner surface 1013 may be located on an arm 1014 that is movable relative to an opposing second inner surface 1015. The inner surfaces may define a slot 1012 operable to receive the catheter 50 with an interference fit at substantially any location along a length of the slot as shown in FIG. 35. To provide the stabilizer 1006 with sufficient flexibility, it may also include one or more thin sections 1008. In one embodiment, the thin section 1008 is formed by various cutouts 1010.

Similar to the stabilizer 906 described above, the arm 1014 may be moved between a first position (shown in FIG. 35) and a second position (shown in FIGS. 34). The stabilizer 1006 may also include features that permit locking the arm 1014 in the first position. For example, the arm 1014 may include a male member, e.g., a ball portion 1016, operable to engage a female receptacle, e.g., socket portion 1018, located on a mating portion of the stabilizer 1006. As a result, the arm 1014 may be locked in the first position (see FIG. 35) after the catheter is located in the slot 1012, whereby the inner surfaces 1013, 1015 may engage the catheter 50 with interference at substantially any location along a length of the slot.

When locked in the first position of FIG. 35, the arm 1014 may position the first inner surface 1013 such that it is substantially parallel to the opposing second inner surface 1015. When the arm 1014 is placed in the second position, a distance between the first and second inner surfaces 1013 and 1015 is greater than when the movable arm is in the first position. As a result, the arm 1014 may be configured in the second position to assist in inserting the catheter in the slot 1012. The ball portion 1016 and socket portion 1018 may act as a stop member that assists in limiting the travel of the arm 1014 (i.e., prevents clamping too tightly against the catheter 50).

FIG. 36 illustrates a side elevation view of the stabilizer member 1006. In this view, raised portions 1020 proximate the inner surfaces 1013 and 1015 are visible. The raised portions 1020 may provide various benefits, e.g., tool interface surfaces that improve the physician's ability to grasp the arm 1014 and squeeze it towards the inner surface 1015 during implantation.

To utilize the stabilizer 1006, a procedure similar to that described above with respect to the apparatus 700 of FIGS. 28A-28D may be used, e.g., the base 702 may be installed in a burr hole as described above with reference to FIGS. 28A-28B. Once the base 702 is correctly positioned, the catheter 50 may be side-loaded into the slot 1012 of the stabilizer 1006 while the stabilizer 1006 is positioned proximate the central opening. To facilitate catheter loading, the stabilizer 1006 may preferably be configured in the second position illustrated in FIG. 34.

The stabilizer 1006 may then be pushed into the central opening of the base 702 until it securely seats against the lip seat 718 (see FIG. 26A). An instrument, e.g., forceps, may be used to draw the arm 1014, and thus the first inner surface 1013, towards the second inner surface 1015 (e.g., via the raised portions 1020) until the protrusion 1016 engages the socket 1018, preferably with a snap-fit as shown in FIG. 35. Once the protrusion 1016 engages the socket 1018, the arm 1014 may be locked in the first position. As a result, the catheter 50 may be clamped and immobilized (by the resulting interference fit) between the first and second inner surfaces 1013 and 1015, respectively, at most any location along the slot length.

Upon verification that the catheter 50 is in place, the catheter may be removed from the stereotactic apparatus, and the stylet (if used) may be withdrawn from the catheter. The catheter 50 may then be placed into one of the channels 716 of the base 702, after which the optional cap member 704 (see FIGS. 25A and 25B) may be coupled to the base as described above.

Figure 37:
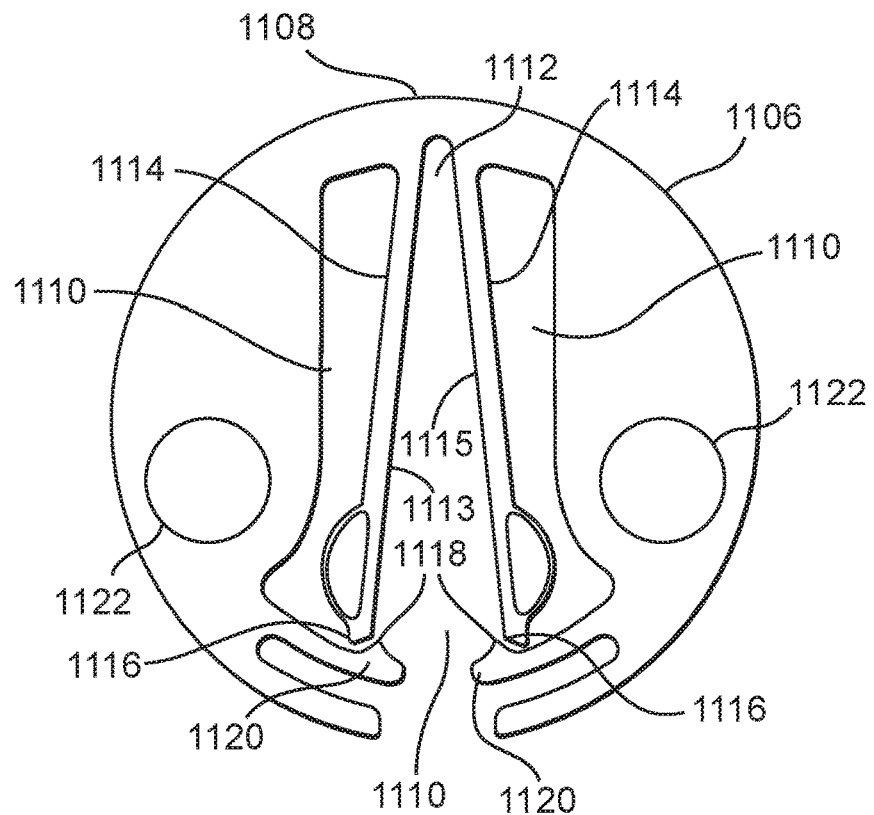
FIG. 37 illustrates a top plan view of a stabilizer in accordance with still yet another embodiment of the invention, wherein arms of the stabilizer are in a second position.
Figure 38:
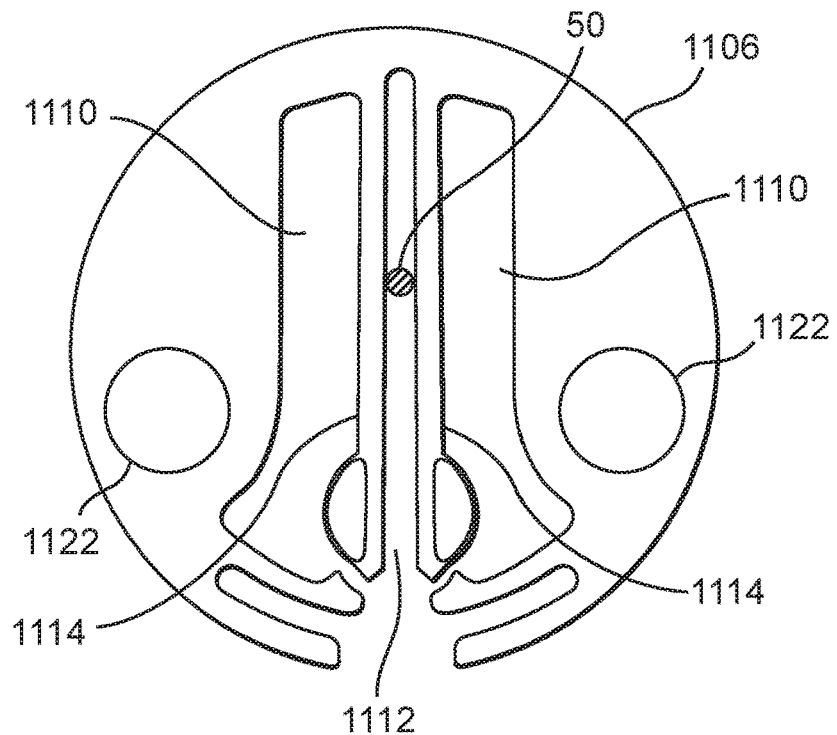
FIG. 38 illustrates the stabilizer of FIG. 37, wherein the arms are in a first position.

FIGS. 37 and 38 illustrate a stabilizer 1106 in accordance with yet another embodiment of the present invention. Once again, the stabilizer 1106 may be substituted for the stabilizer 706 within the retention apparatus 700 (e.g., may be used with the base 702 and cap member 704 shown in FIGS. 25A and 25B) already described above.

As with other stabilizer members described above (see, e.g., stabilizers 706 and 806), the stabilizer 1106 may form a resilient disk-shaped member that may be compressed sufficiently to fit (e.g., with interference) into the central opening of the base 702 and rest against the lip seat 718 (see FIG. 26A).

The stabilizer 1106 may be defined by a peripheral edge and various inner surfaces, e.g., a first inner surface 1113 and a second inner surface 1115. The first and second inner surfaces 1113 and 1115 may define a slot 1112 extending through the peripheral edge of the stabilizer 1106. Both of the surfaces 1113 and 1115 may be defined by opposing movable arms 1114 operable to press the therapy delivery device (e.g., catheter 50) against the opposing surface at most any location along a slot length. To provide the stabilizer 1106 with sufficient flexibility, it may further include one or more thin sections 1108 formed by one or more cutouts 1110.

The two opposing arms 1114 may be moved from a first position (shown in FIG. 38), to a second position (shown in FIG. 37). The arms 1114, when in the second position, provide a greater distance between the surfaces 1113 and 1115 (as compared to the first position) to assist with loading and positioning the catheter 50.

The stabilizer 1106 may also include a lock portion for locking each arm 1114 in at least the second position. For example, a cantilevered end of each arm 1114 may include a tooth 1116 operable to engage a corresponding tab 1118 when the arm is deflected to the second position (see FIG. 37). As a result, the arm 1114 may be locked in the second position of FIG. 37 during a portion of the implantation process. The tab 1118 may be attached to a flexible protrusion 1120 that can be deflected to release the arm 1114 from the second position at the appropriate time. The stabilizer 1106 may also include one or more openings 1122 defining tool interface surfaces operable to receive forceps or the like.

To utilize the stabilizer 1106, a procedure similar to that described above with respect to the apparatus 700 of FIGS. 28A-28D may be used, e.g., the base 702 may be installed as described above (see FIGS. 28A-28B). Once the base 702 is correctly positioned in the burr hole, the catheter 50 (which may already be located through the burr hole) may be side-loaded into the slot 1112 of the stabilizer 1106 while the latter is positioned proximate the burr hole and configured in the second, deflected position illustrated in FIG. 37. An instrument, e.g., forceps, may be placed into the openings 1122 of the stabilizer 1106 to squeeze or deform the stabilizer sufficiently to then fit within the central opening of the base 702. Release of the squeezing force may permit the stabilizer 1106 to expand and secure relative to the base 702.

Once the stabilizer 1106 is adequately deformed, it may be placed into the base 702 and seated against the lip seat 718 (see FIG. 26A). An instrument, e.g., forceps, may then be used to displace the flexible protrusions 1120 to which the tabs 1118 are attached (or may simply pull the arms 1114 towards one another). When the flexible tabs 1120 are sufficiently displaced, the arms 1114 may be unlocked, whereby they may return, under biasing forces, to their first position as shown in FIG. 38, thus clamping the catheter 50 in place (with the resulting interference fit) between the first and second inner surfaces at substantially any location along a length of the slot.

Upon verification that the catheter 50 is in place, the catheter 50 may be removed from the stereotactic apparatus and the stylet (if used) withdrawn from the catheter. The catheter 50 may then be placed into one of the channels 716 of the base 702, and the optional cap member 704 coupled to the base as described above.

Figure 39:
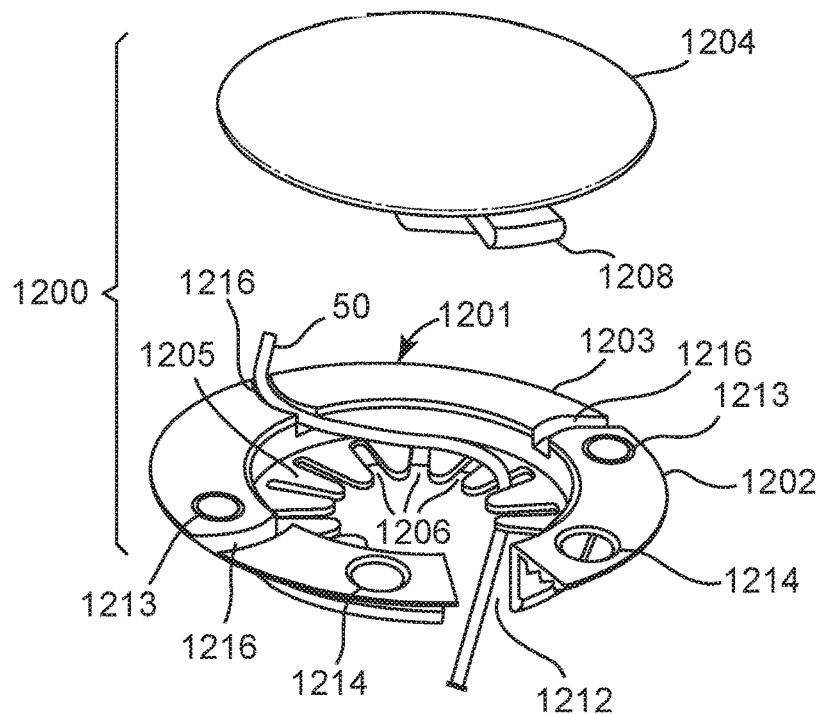
FIG. 39 illustrates an exploded upper perspective view of a burr hole retention apparatus in accordance with still yet another embodiment of the invention.
Figure 40:
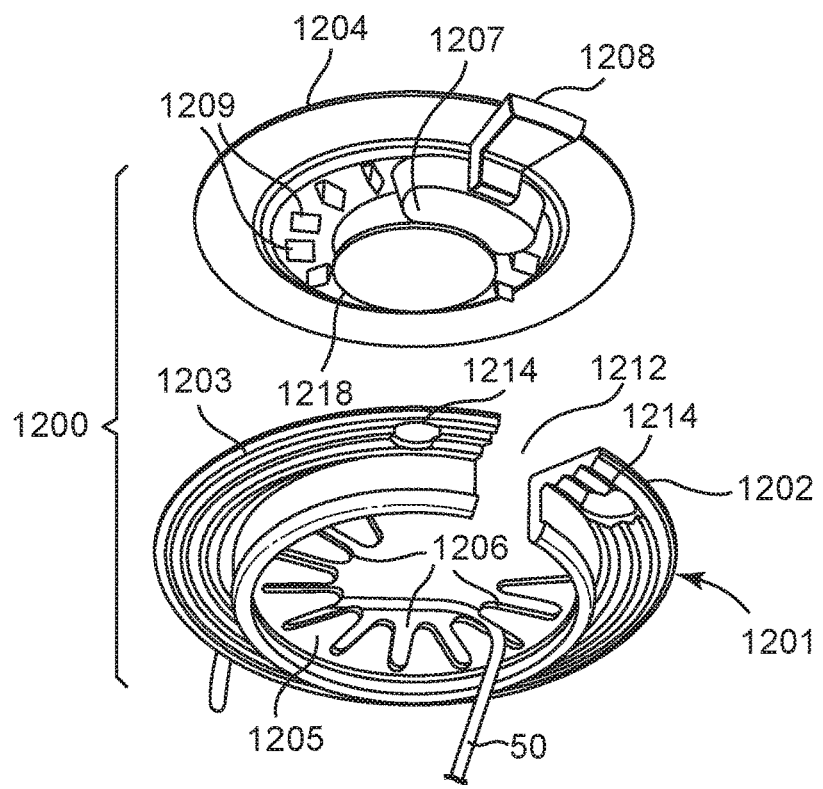
FIG. 40 is an exploded lower perspective view of the apparatus of FIG. 39.
Figure 41:
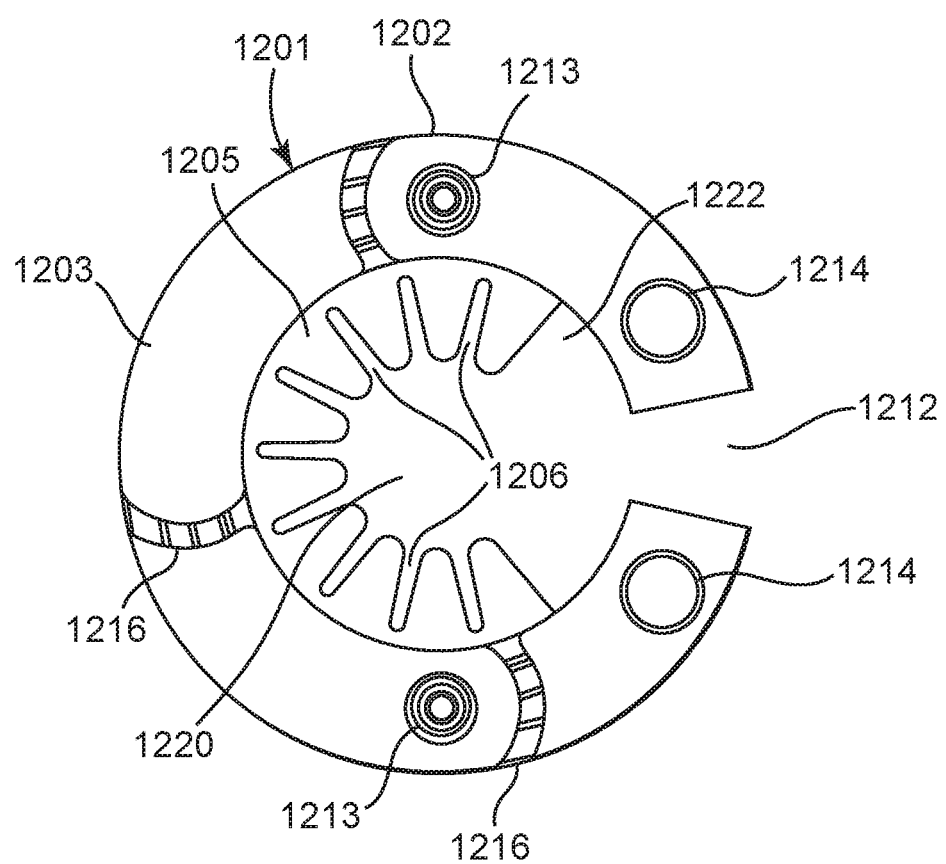
FIG. 41 is a top plan view of a base and stabilizer of the apparatus of FIGS. 39-40.

FIGS. 39-41 illustrate a burr hole retention apparatus 1200 in accordance with yet another embodiment of the invention. The apparatus 1200 may replace the three-piece apparatus 700 of FIGS. 25A and 25B with the configuration shown in FIGS. 39 (exploded upper perspective view) and 40 (exploded lower perspective view).

The apparatus 1200 may include a base assembly 1201 for seating in or near the burr hole, and a cap or cap member 1204. In the illustrated embodiment, the base assembly 1201 may include both a base 1202 and a disk-shaped stabilizer 1205. The cap member 1204 may similarly be a multi-piece construction. While illustrated and described herein as an assembly, the cap assembly could, alternatively, be constructed as a single component without departing from the scope of the invention.

The base 1202 may include an engagement portion operable to engage the inner surface of the burr hole when the base is coupled thereto. In one embodiment the base 1202 may be a generally C-shaped member having a passageway 1212 formed therein, similar in most respects to the base 702 described above. As with the previously described embodiments of base members, the passageway 1212 may allow compression (deflection) of the base 1202 to permit insertion of the same into the burr hole.

The base may further include a peripheral portion defining a flange portion 1203 that is operable to seat or rest against the cranial surface when the base 1202 is in place. The peripheral portion, e.g., flange portion 1203, may at least partially surround a central opening that is designed to receive the stabilizer 1205 therein (or in close proximity). The flange portion 1203 may further include openings 1214 defining tool interface surfaces for receiving forceps or similar tools to compress the base 1202 during insertion of the same into the burr hole. Screw holes 1213 may optionally be provided to permit mechanical attachment of the base 1202 to the skull with fasteners (see, e.g., fastener 717 in FIG. 26A).

In the illustrated embodiment, the stabilizer 1205 is a separate component that is attached or otherwise fixed to the flange portion 1203, e.g., securely seated with interference against a lip seat similar to the lip seat 718 shown in FIGS. 26A-26B. However, this is not limiting as other embodiments may form the stabilizer as an integral component with the base 1202.

The stabilizer 1205 may form a partial ring of material having an outer edge and inner sidewalls. The inner sidewalls may define a window 1220 or opening passing through the stabilizer, and a passageway 1222 extending outwardly from the window through the outer edge as shown in FIG. 41. Two or more slots, e.g., radially extending slots 1206, in communication with the window 1220 may be provided to each frictionally engage the catheter 50 (e.g., engage it with an interference fit as generally illustrated in FIGS. 39 and 40) at most any location along a slot length. The slots 1206 may result in the formation of a plurality of wedge- or pie-shaped elements as shown in the figures. The passageway 1222 may permit an implantable device, e.g., catheter 50, to be side-loaded through the assembly 1201 and, ultimately, located in one of the slots 1206.

In one embodiment, the stabilizer 1205 is formed from a resilient and flexible material such as polycarbonate or polysulfone. However, other materials (e.g., silicone) of greater or lesser rigidity are certainly possible without departing from the scope of the invention.

The base 1202 may also include one or more channels 1216 formed in an upper surface of the peripheral portion, e.g., the flange portion 1203. The channels 1216 may each have a width equal to or less than the undeflected outer dimension of the catheter 50 so that each channel may receive the catheter with an interference fit. The interference fit may be similar to those already described herein above, see, e.g., channel 132 of apparatus 100. The channel 1216 may extend outwardly from the central opening to a point at (e.g., through) or near an outermost edge of the peripheral portion as shown in FIGS. 39 and 41. The channel 1216 may optionally form a slot extending downwardly through a lower surface of the peripheral portion (flange portion 1203).

Preferably, each channel 1216 is non-linear, i.e., circuitous, so that the catheter is frictionally engaged within the channel in at least two non-parallel directions. For example, in the embodiment illustrated in FIGS. 39-41, each channel 1216 may form a generally continuous curved segment, e.g., a radius. However, the illustrated shape of the channel 1216 is not considered limiting as other shapes are certainly possible without departing from the scope of the invention, see, e.g., the intersecting linear segments of channel 716 of the base 702.

The optional cap member 1204, shown in FIGS. 39 and 40, may form a disk-shaped cover with an optional tab portion 1208 protruding from a peripheral edge. The cap assembly 1204 is operable to sit over an upper surface of the base assembly 1201 when installed, such that a protrusion, e.g., the tab portion 1208, may fit within an opening in the base 1202 or stabilizer 1205, e.g., the passageway 1212. The tab portion 1208 may assist in aligning the cap member 1204 relative to the base 1202, and further provide a tab to assist with cap member removal. The cap member 1204 may also include a plug portion 1207 operable to fit within the passageway 1222 (see FIG. 41).

The cap 1204, in one embodiment, may be made from a relatively soft material, e.g., silicone having a durometer of about 55 Shore D to about 65 Shore D, polyurethane having a durometer of about 80 Shore A, or polycarbonate (e.g., polycarbonate sold under the trademark Makrolon 2458).

A lower surface of the cap 204 may further include an interlocking element operable to engage and secure the cap 1204 to the base 1202. In one embodiment, the interlocking element is formed by a protrusion 1218 operable to extend through the window 1220 and beneath the innermost edges of the stabilizer 1205. For example, an effective outer diameter of the protrusion 1218 may be slightly larger than an effective inner diameter formed by the inner edges of the stabilizer 1205. As a result, the components may positively couple, e.g., couple with a snap-fit.

The lower surface of the cap 1204 may also include a series of protrusions 1209. The protrusions 1209 are preferably configured to be flexible so that they may assist in frictionally engaging the catheter 50 without applying excessive pinching forces that would tend to collapse the catheter.

The base 1202 may be implanted in much the same way as the base members described above (e.g., base member 702 of FIGS. 28A-28D). With the base 1202 and catheter 50 positioned within the burr hole, the stabilizer 1205 may be positioned proximate the base 1202, where the catheter 50 may be positioned such that it extends through the window 1220. The stabilizer 1205 may then be secured relative to the central opening of the base 1202 (e.g., coupled to the base). The catheter 50 can then be moved into one of the slots 1206 of the stabilizer, where it is frictionally engaged by the two opposing sidewalls that define the slot. Upon verification that the catheter 50 is in place, the catheter 50 may be removed from the stereotactic apparatus and the stylet (if used) may be withdrawn from the catheter.

The catheter 50 may then be routed and secured in one of the channels 1216, where it may seat with an interference fit. The cap assembly 1204 may then be coupled to the base member 1202 by insertion of the disk portion 1218 past the stabilizer 1205. The interference fits between the catheter 50 and both the slot 1206 and channel 1216 serve to substantially fix the catheter in the desired position. Moreover, the protrusions 1209 on the lower surface of the cap assembly 1204 (see FIG. 40) may also assist in immobilizing the catheter 50.

Figure 42:
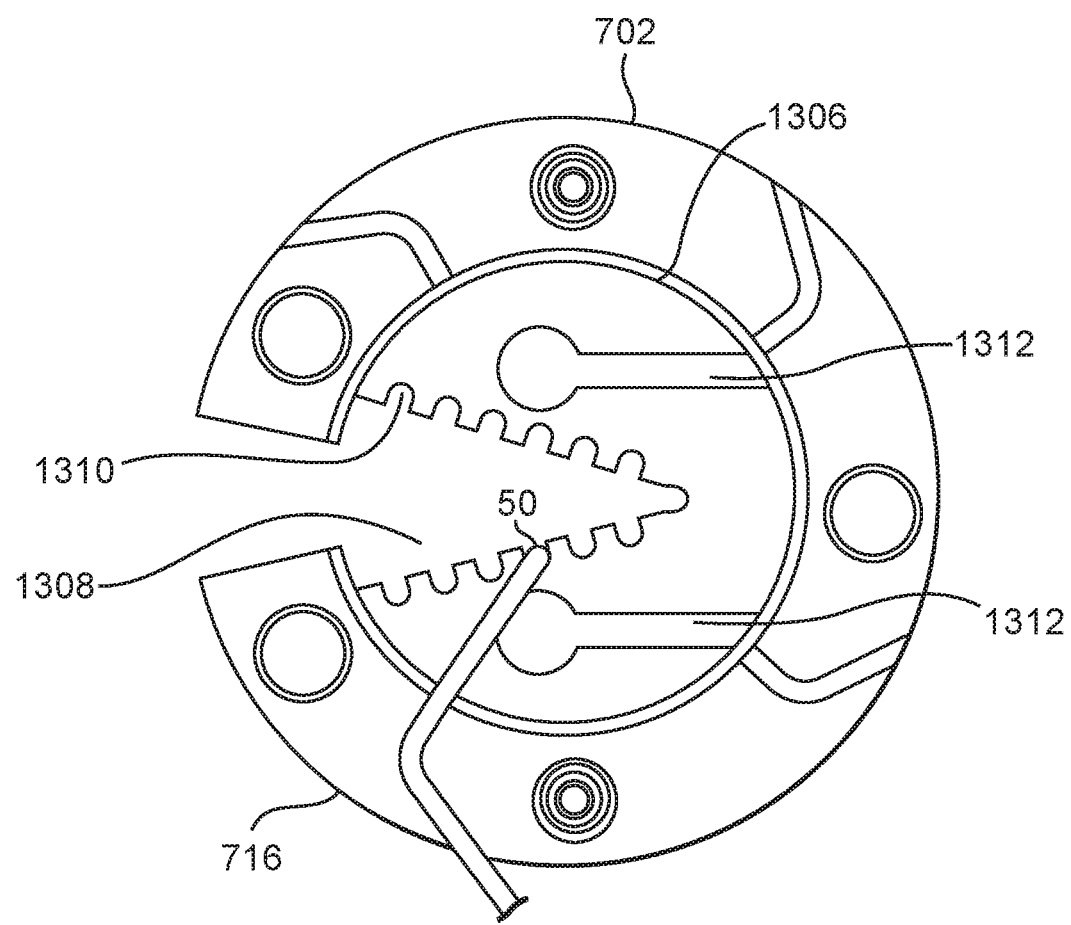
FIG. 42 illustrates a top plan view of a stabilizer in accordance with still yet another embodiment of the invention, the stabilizer shown assembled with a base, e.g., the base member of FIGS. 26A-26B.

FIG. 42 illustrates a stabilizer 1306 in accordance with still yet another embodiment of the present invention, the stabilizer shown assembled with a base member (e.g., the base 702 of FIGS. 25A and 25B). In this embodiment, the stabilizer 1306 has an inner sidewall defined by a cutout or slot extending through an outer edge of the stabilizer. The cutout, in the illustrated embodiment, is in the form of V-shaped opening or passageway 1308. Along the inner sidewalls of the V-shaped opening are a series of open-sided notches 1310. The notches 1310 are each operable to frictionally secure a catheter, e.g., catheter 50, at a discrete location along a length of the sidewalls.

The stabilizer 1306 may also include one or more cutouts 1312 defining tool interface surfaces that allow compression of the stabilizer for insertion into the base 702 as described above (see, e.g., stabilizer 706). Alternatively, the stabilizer 1306 could compress or deform due to the thin section formed at the apex of the V-shaped opening 1308. In such a case, the cutouts 1312 may not be required. In other embodiments, holes or raised lips (not shown) may be provided on each side of the V-shaped opening 1308.

In use, the stabilizer 1306 may engage the base 702 much like the stabilizer members described above (stabilizer 706 with base member 702). As with other stabilize embodiments described herein, the stabilizer 1306 may be oriented or clocked as desired to position the notches in the desired area.

In some embodiments, the stabilizer 1306 may rotate, with appropriate friction, after it has been seated in the base member 702. As a result, the stabilizer 1306 may be implanted in much the same way as the stabilizers already described herein (see, e.g., stabilizer 706 of FIGS. 28A-28D). However, once the base 702 and stabilizer 1306 are assembled, the stabilizer may be rotated until the catheter 50 engages one of the notches 1310 with an interference fit. The stylet may then be removed and the optional cap member (e.g., cap 704) may be installed as already described herein.

FIGS. 43-46 illustrate a stabilizer 1406 in accordance with yet another embodiment of the present invention. The stabilizer 1406 may replace the stabilizer 706 in the retention apparatus 700 described above and illustrated in FIGS. 25A-25B (i.e., it may be used with the base 702 and cap member 704).

As with the stabilizer 706, the stabilizer 1406 may form a resilient disk-shaped component that may be diametrically compressed sufficiently to fit into the central opening of the base 702 (e.g., with interference), where it may rest against the lip seat 718 (see FIG. 26A) and be secured relative to the base.

Figure 46:
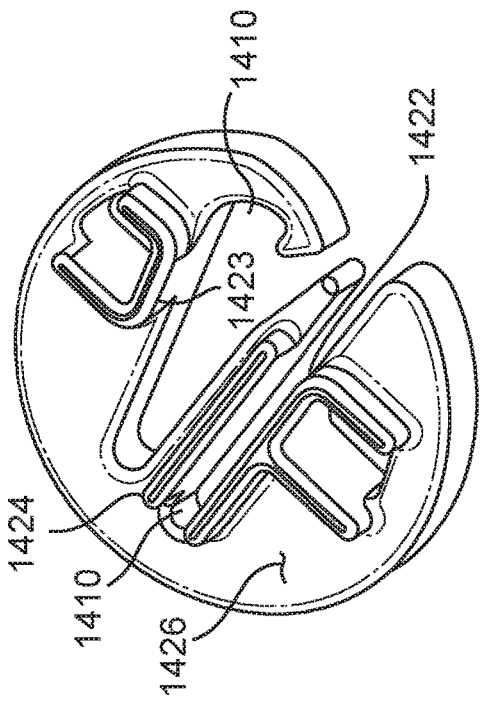
FIG. 46 is an upper perspective view of the stabilizer of FIG. 43.
Figure 43:
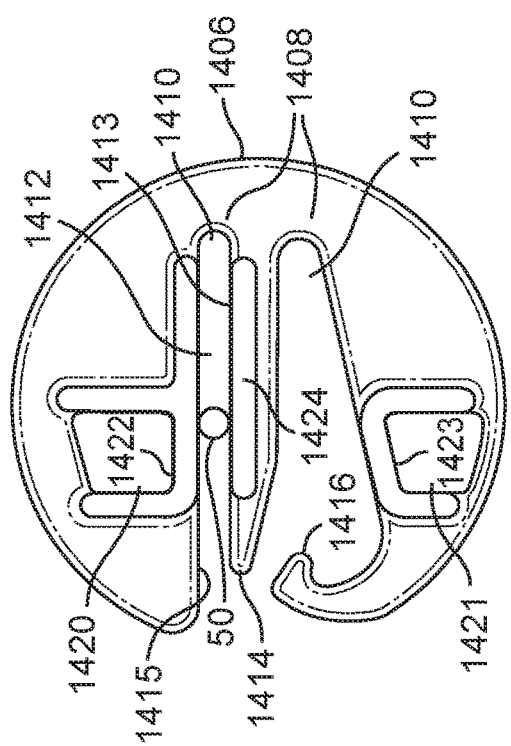
FIG. 43 illustrates a top plan view of a stabilizer in accordance with another embodiment of the invention, wherein an arm of the stabilizer is in a first position.

The stabilizer 1406 may be defined by a peripheral edge and opposing first and second inner surfaces 1413, 1415. The first and second inner surfaces 1413, 1415 may define a slot 1412 extending through the peripheral edge. The slot 1412 may receive the catheter 50 at most any location along the slot length. To provide the stabilizer 1406 with sufficient flexibility, it may include one or more thin sections 1408 formed by various cutouts 1410 as shown in FIGS. 43, 45, and 46.

Figure 45:
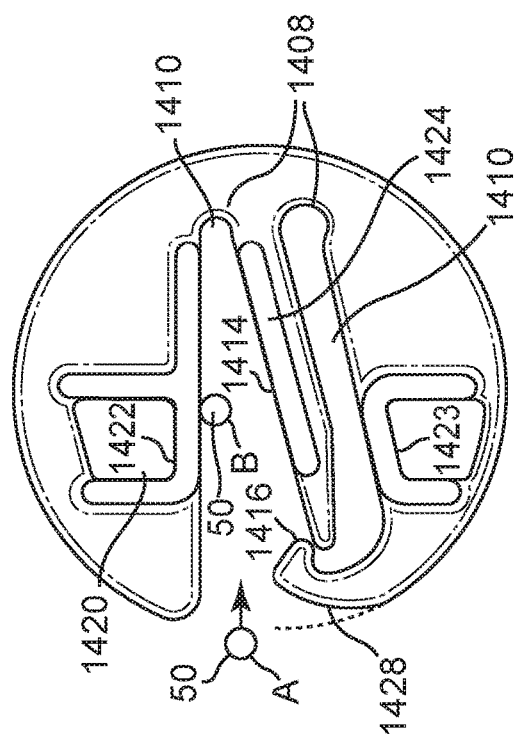
FIG. 45 is a top plan view of the stabilizer of FIG. 43, wherein the arm is in a second position.

The first inner surface 1413 of the stabilizer 1406 may be defined by an arm 1414 that may move between a first position (shown in FIG. 43), and a second position (shown in FIG. 45). In the first position, the first inner surface 1413 of the movable arm 1414 may be substantially parallel to the second inner surface 1415. As a result, the first inner surface 1413 may press the catheter 50 against the second inner surface 1415 at most any location along a length of the slot. When the movable arm 1414 is in the second position of FIG. 45, a distance between the first and second inner surfaces (1413, 1415) is greater than when the arm is in the first position of FIGS. 43 and 46 to assist with catheter insertion and location.

The stabilizer 1406 may also include a lock portion that permits locking the arm 1414 in the second position. For example, the stabilizer 1406 may include a tab 1416 operable to engage a cantilevered end of the arm 1414 when the latter is deflected to its second position. The tab 1416 may be sufficiently flexible to permit releasing of the arm 1414 from the second position at the appropriate time as further described below. In the illustrated embodiment, the second inner surface 1415 is substantially fixed relative to the stabilizer 1406.

Figure 44:
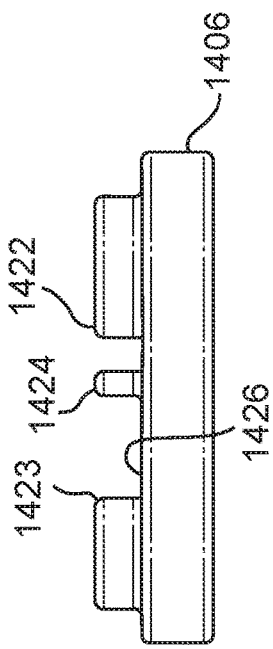
FIG. 44 is a side elevation view of the stabilizer of FIG. 43.

The stabilizer 1406 may also include openings 1420 and 1421 operable to assist with implantation as further described below. In the embodiments illustrated in FIGS. 43-46, a portion of a perimeter of each opening 1420, 1421 may include an optional raised lip 1422, 1423, respectively. The raised lips 1422, 1423, which may extend above an upper surface 1426 of the stabilizer member 1406 as shown in FIGS. 44 and 46, may provide more convenient and larger tool interface surfaces for grasping the stabilizer member with a tool, e.g., forceps. In other embodiments, the openings 1420, 1421 (or the raised lips 1422, 1423) may be optional, e.g., the raised lips 1422, 1423 or the openings 1420, 1423 may be provided independent of one another.

The arm 1414 may also include an optional raised lip 1424. As with the lips 1422 and 1423, the raised lip 1424 may provide a more convenient and larger tool interface surface for manipulating the arm 1414 as further described below. In some embodiments, the raised lips 1422 and 1424 may extend along a substantial portion of the length of the slot 1412. Such a configuration may provide, among other benefits, increased contact surface between the stabilizer member 1406 and the catheter 50.

To utilize the stabilizer 1406, a procedure similar to that described above with respect to the apparatus 700 of FIGS. 28A-28D may be used. For example, the base 702 and catheter 50 may be located in a burr hole (see FIG. 28B) as described above. Once the base 702 and catheter 50 are correctly positioned, the stabilizer member 1406 may be positioned in or near the central opening and side loaded over the catheter 50 such that the catheter is routed through the slot 1412 as shown by position A of the catheter in FIG. 45. During this process, the arm 1414 of the stabilizer 1406 may preferably be configured in its second position as illustrated in FIG. 45.

An instrument, e.g., forceps, may be placed into the openings 1420 and 1421 (and/or over the surfaces 1422 and 1423) of the stabilizer member 1406 to apply a first force. The first force may deform the diameter of the stabilizer sufficiently such that it may fit within the central opening of the base 702. The thin sections 1408 may permit sufficient deflection of the stabilizer 1406 to accomplish deformation and placement with the forceps-applied force.

With the stabilizer 1406 adequately deformed, it may be placed into the base 702 and seat against the lip seat 718 (see FIGS. 26A and 26B), after which the forceps-applied force may be released. The stabilizer 1406 may then expand to securely seat within the base 702, e.g., with interference. As with other embodiments described herein, the stabilizer 1406 may be clocked, relative to the base 702, to align the slot 1412 in most any direction.

With the catheter 50 in the desired location within the slot (see, e.g., position B of FIG. 45), a second force may then be applied, e.g., with forceps, between the lips 1422 and 1424. The second force may displace the tab 1416 outwardly. The outer edge 1428 of the tab 1416 may be such that it can expand outwardly (see FIG. 45) without restriction or interference from the base 702. When a sufficient second force is applied, the arm 1414 may be unlocked from the tab 1416, whereupon it may be moved, e.g., biased, towards the catheter 50 to the arm's first position as shown in FIG. 43.

In the first position, the arm 1414 may apply a slight clamping force (interference fit) to the catheter 50 to immobilize the latter relative to the stabilizer 1406 at most any location along the slot length. Upon verification that the catheter 50 is in place, the catheter 50 may be removed from the stereotactic apparatus and the stylet (if used) may be withdrawn from the catheter. The catheter may then be placed into one of the channels 716 of the base 702 (see FIGS. 26A and 26B), and the optional cap member 704 coupled to the base as described above.

FIGS. 47-49 illustrate a stabilizer 1506 in accordance with yet another embodiment of the present invention. The stabilizer 1506 may again replace the stabilizer 706 in the retention apparatus 700 described above and illustrated in FIGS. 25A-25B.

As with the stabilizer 706, the stabilizer 1506 may form a resilient disk-shaped member that may be diametrically compressed sufficiently to fit into the central opening of the base 702 and rest against the lip seat 718 (see FIG. 26A).

The stabilizer 1506 may be defined by a peripheral or outer edge and inner sidewalls. The inner sidewalls may define a window 1515 passing through the stabilizer, and a passageway 1517 extending outwardly from the window through the outer edge of the stabilizer. The inner sidewalls may further define two or more slots 1512 in communication with the window 1515. Each of the two or more slots are operable to frictionally engage the delivery device at most any location along a slot length as diagrammatically represented by the various broken line catheters 50 illustrated in FIG. 47.

To provide the stabilizer 1506 with sufficient flexibility, it may include one or more thin sections 1508 formed by various cutouts 1510, e.g., formed by the window 1515, as shown in FIGS. 47 and 49. As with other embodiments described herein, the stabilizer 1506 may be clocked, relative to the base 702, to align the slot 1512 in most any direction.

Each slot 1512 may be defined by at least one arm 1514 (see FIG. 49). Unlike the embodiment of FIGS. 43-46, however, the arms 1514 are not designed to be substantially deflected. Rather, each arm may remain generally fixed, or deflect only slightly, during use to ensure that the corresponding slots 1512 receive the catheter 50 with the desired interference fit.

The stabilizer 1506 may also include openings 1520 and 1521 that form tool interface surfaces operable to assist with implantation as further described below. Like the embodiment illustrated in FIGS. 43-46, a portion of a perimeter of each opening 1520, 1521 may include an optional raised protrusion or lip 1522, 1523, respectively. The raised lips 1522, 1523, which extend from an upper surface 1526 of the stabilizer member 1506 as shown in FIGS. 48 and 49, may provide a more convenient and larger tool interface surface for grasping the stabilizer with a tool, e.g., forceps. In other embodiments, either the openings 1520, 1521, the raised lips 1522, 1523, or both, may be optional.

A portion of the window 1515 and/or slots 1512 may also include optional raised lips 1524. While not illustrated, the raised lips 1524 could extend along a substantial portion of the length of one or more of the slots 1512. Such a configuration could provide, among other benefits, increased contact surface between the stabilizer 1506 and the catheter 50, and greater structural integrity.

To utilize the stabilizer 1506, a procedure similar to that described above with respect to the apparatus 700 of FIGS. 28A-28D may be used. For example, the base 702 and catheter 50 (see FIGS. 28A and 28B) may be installed in a burr hole. Once the base and catheter are correctly positioned, the stabilizer 1506 may be positioned proximate the base 702. The catheter 50 may then be passed or side-loaded through the passageway 1517 such that the catheter is positioned through the window 1515 as shown by position A of the catheter in FIG. 47.

An instrument, e.g., forceps, may be placed into the openings 1520 and 1521 (and/or over the surfaces 1522 and 1523) of the stabilizer 1506 to apply a first force. The first force may reduce the diameter of the stabilizer sufficiently such that it may fit within the central opening of the base 702. The thin section 1508 may permit sufficient deflection of the stabilizer 1506 to accomplish this deformation and placement with the forceps-applied force.

With the stabilizer 1506 adequately deformed, it may be placed into the base 702 and seat against the lip seat 718 (see FIGS. 26A and 26B), after which the forceps-applied force may be released. The stabilizer 1506 may then expand to securely couple to the base 702 (e.g., with interference) within the central opening. The catheter 50 may then be moved from the window 1515 into one of the slots 1512 where it is then frictionally engaged at most any location along a length of the slot.

With the catheter 50 in the desired location within one of the slots 1512 (see, e.g., position B of FIG. 47), the corresponding sidewalls may apply a slight clamping force (frictional interference fit) to the catheter 50 to immobilize the latter relative to the stabilizer 1506. Upon verification that the catheter 50 is in place, the catheter 50 may be removed from the positioning equipment, e.g., stereotactic apparatus, and the stylet (if used) may be withdrawn from the catheter. The catheter may then be placed into one of the channels 716 of the base 702 (see FIGS. 26A and 26B), and the optional cap member 704 coupled to the base as described above.

The stabilizer 1506, as well as the other stabilizer members described herein (e.g., 706, 806, 906, 1006, 1106, 1205, 1306, and 1406) may be configured to reduce relative movement between the catheter and the stabilizer. For example, the material and/or surface finish of the stabilizers may include granular, adhesive, or other friction-enhancing coatings selected to increase frictional resistance. Alternatively, the surface of the stabilizer may be roughened, e.g., mechanically abraded or produced in a roughened mold, to provide a higher degree of frictional resistance.

In some embodiments, the stabilizers could be impregnated or coated with a material that may increase frictional resistance. For example, polymeric coating materials such as silicone, polyurethane, polyethylene, and polyacrylate (e.g., modified polyacrylates) may be used. Vitreous or paralytic carbon materials may also be used to create the desired surface. In some embodiments, the coating material may be applied to the stabilizer via a dipping process (although other processes (e.g., spraying) are certainly possible without departing from the scope of the invention).

Such coatings may provide a tacky frictional interface between the stabilizer and the catheter. It was discovered that by utilizing such coatings, a substantial increase in pull force (the force required to cause movement of the catheter relative to the stabilizer) could be realized. For example, a stabilizer substantially similar to the stabilizer 1506 illustrated in FIGS. 47-49 was made from nylon (i.e., Grilamid Nylon 12 produced by EMS-Chemie AG Corp. of Switzerland) and was designed to provide an undeflected slot 1512 width (see FIG. 47) of about 0.5 mm. A catheter (e.g., catheter 50) made of polyurethane (of durometer 80 Shore A), having an undeflected outer diameter of about 1 mm and a wall thickness of about 0.2 mm, was then inserted into one of the slots 1512 as described above. This configuration resulted in a pull force of about 0.2 pounds (lbs). When the same stabilizer member was then coated with polyurethane to a thickness of about 0.01 mm, the pull force increased to about 0.7 lbs.

Thus, by selecting appropriate materials and/or surface finishes/coatings for the stabilizer, relative movement between the stabilizer and the catheter may be reduced. The friction-enhancing coating preferably provides a coefficient of friction of at least about two times, and preferably at least about three times, that of the underlying material.

While described herein as applied only to the stabilizer, such friction-enhancing coatings could also be applied to other components of the retention apparatus, e.g., to the base 702 and cap 704 of FIGS. 25A and 25B.

Figure 52:
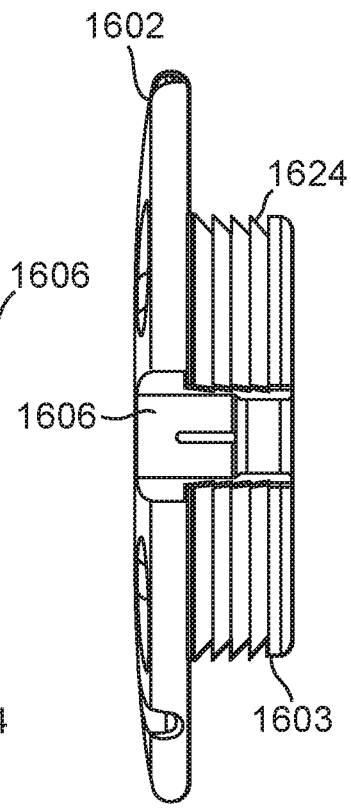
FIG. 52 is a side elevation view of the base of FIG. 50.

While various embodiments of stabilizers are described in detail herein, other bases and cap member configurations are also contemplated. For example, FIGS. 50-52 illustrate a base 1602 in accordance with another embodiment of the invention.

The base 1602 may be similar in many respects to the base 702. For example, it may form a generally annular, C-shaped member having a passageway or gap 1606 extending through its sidewall. It may further include a lower engagement portion 1603 with optional protrusions 1624 incorporated thereon as shown in FIG. 52. The base 1602 may further include forceps-receiving openings 1614 defining tool interface surfaces to assist in compressing the base for insertion into the burr hole. The openings 1614 are illustrated as ovals in FIGS. 50 and 51. The oval shape may allow more latitude when attaching a cap member 1604 (further described below).

Figure 50:
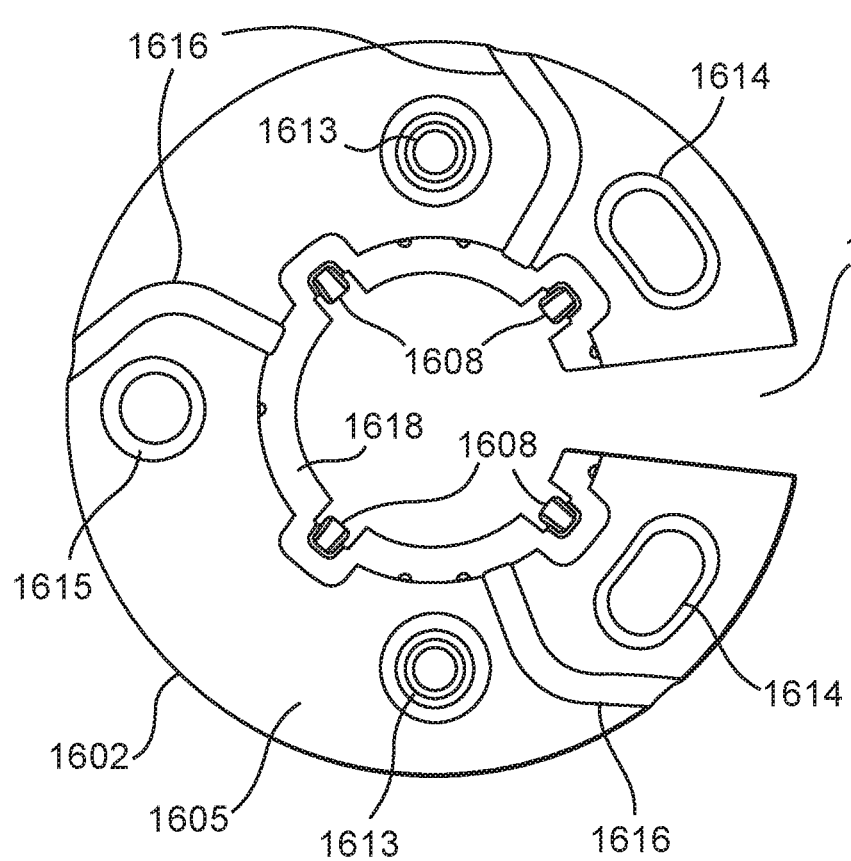
FIG. 50 illustrates a top plan view of a base or base member of a burr hole retention apparatus in accordance with another embodiment of the invention.
Figure 51:
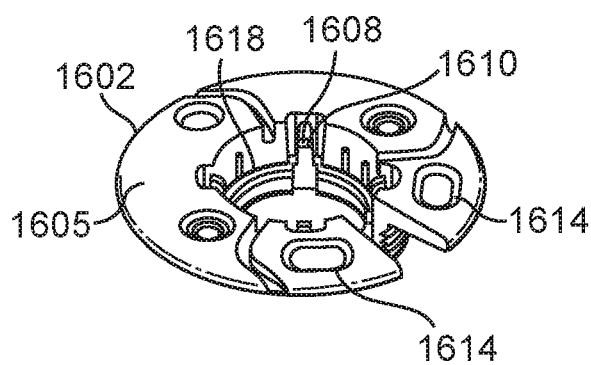
FIG. 51 is an upper perspective view of the base of FIG. 50.

FIG. 50 illustrates an upper flange surface 1605 of the base 1602. As illustrated in this view, the upper flange surface 1605 may include at least one channel 1616 operable to receive the catheter 50 with an interference fit similar to those already described herein. Preferably, each channel 616 is circuitous (e.g., non-linear) so that the catheter 50 is frictionally engaged within the channel in at least two non-parallel directions. For example, in the illustrated embodiment, each channel 1616 has at least one curved segment and two intersecting linear segments formed therein to produce the multi-directional frictional forces. However, the illustrated shape of the channel 1616 is not considered limiting as other shapes are certainly possible without departing from the scope of the invention. Moreover, while the channels 1616 are shown as forming shallow channels in the upper flange surface 1605 of the base, other embodiments may utilize channels that form slots extending entirely through a lower surface of the upper flange portion.

The base 1602 may also include optional screw holes 1613 to secure the base to the skull surface of the patient. Moreover, one or more openings 1615 may, in conjunction with openings 1614, receive and interlock with tab portions of the optional cap member 1604 shown in FIGS. 53-55.

The base 1602 may further include a shelf or lip seat 1618, shown in FIGS. 50-51, that is similar to the seat 718 of the base 702. The lip seat may form a surface upon which the stabilizer (see, e.g., stabilizer member 1506) may rest when properly installed in the base 1602.

The base 1602 may further include two or more clips 1608 each having a tooth 1610 (see FIG. 51). In the illustrated embodiments, the clips are integrally formed with the base 1602. Each clip 1608 may deflect upon insertion of the stabilizer (e.g., stabilizer member 1506) and, once the stabilizer is correctly seated, spring back to an undeflected position. Thus, the teeth 1610 may hold the stabilizer (e.g., stabilizer 1506) against the lip seat 1618 of the base 1602 with a snap fit. In the illustrated embodiment, four clips 1608 are illustrated, but more (or less) are certainly possible without departing from the scope of the invention.

FIGS. 53-55 illustrate an exemplary cap member 1604 that may be used with the base 1602 (or with other base members/assemblies described herein). The cap member 1604 may include tab portions 1620 on its lower side (see side elevation view of FIG. 54 and lower plan view of FIG. 55) that may engage the openings 1614 and 1615 of the base (see FIG. 51) sufficiently to ensure retention of the cap member to the same.

To assist with alignment of the cap member during installation, the lower side of the cap member 1604 may also include an elongate rib 1626 that may fit within the passageway 1606. A lift tab 1628, which may be located at an end of the rib 1626 (see FIG. 53), may provide a pry mechanism for easily removing the cap member when desired.

Figure 56:
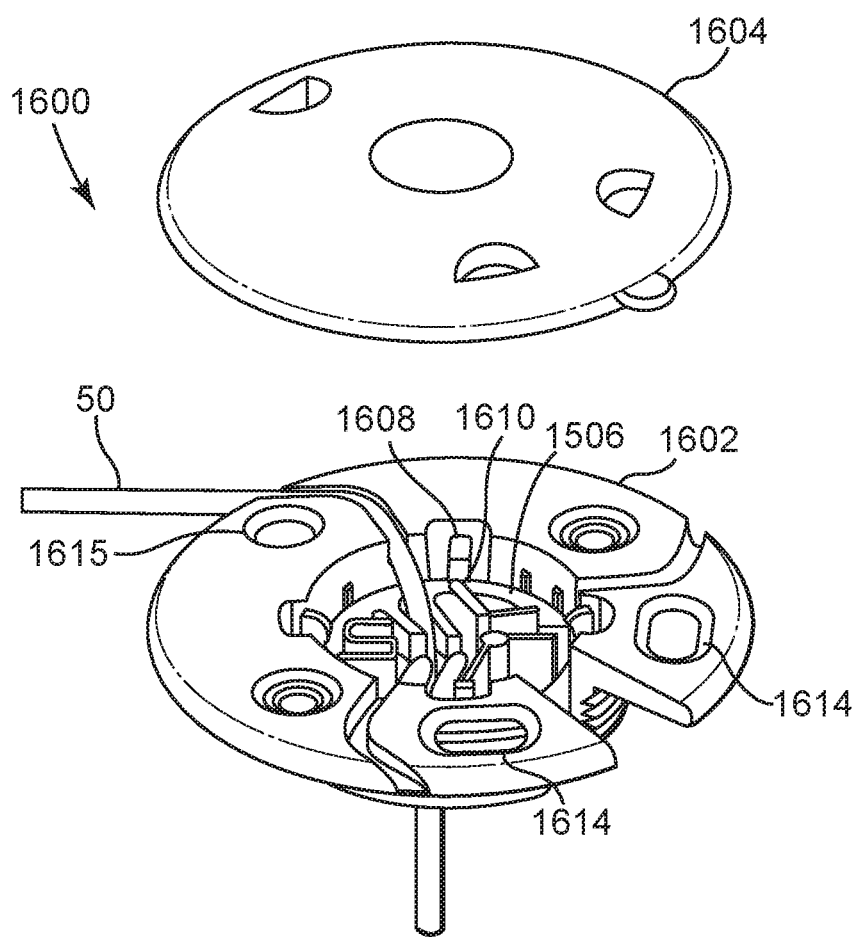
FIG. 56 illustrates a burr hole retention apparatus in accordance with another embodiment of the invention, the apparatus incorporating the stabilizer of FIGS. 47-49, the base of FIGS. 50-52 and the cap member of FIGS. 53-55.

FIG. 56 illustrates an exemplary retention apparatus 1600 incorporating the base 1602, cap member 1604, and exemplary stabilizer 1506 as described above. As illustrated in this view, the stabilizer 1506 may seat within the base 1602, where it may then be held in place by the teeth 1610 of the clips 1608. The cap member 1604 may secure to the base 1602 by engagement of the tab portions 1620 (see FIG. 55) with the openings 1614 and 1615.

The apparatus 1600 may be implanted in much the same way as the apparatus 700 described above and illustrated in FIGS. 28A-28D. Accordingly, no additional description is provided herein. Moreover, the components of the apparatus 1600 (e.g., the base 1602, cap member 1604, and stabilizer 1506) may be made from the biocompatible materials already described herein.

Advantageously, embodiments of the present invention provide burr hole retention apparatus and methods that permit precise locating and secure anchoring of an implanted therapy delivery device. These apparatus and methods further permit insertion of the therapy delivery device prior to insertion of the retention apparatus. As a result, the physician may have unimpeded access to the entire burr hole during device implantation. The present invention further provides retention apparatus having a low-profile. Such low profile devices may provide various advantages, e.g., implants that are less visible and less stressful on local tissue. Other embodiments may utilize additional features, e.g., fastener-less cranial attachment, friction-enhancing coatings, etc., that may further benefit implantation and/or the ability of the retention apparatus to secure the therapy delivery device.

The complete disclosure of the patents, patent documents, and publications cited in the Background, the Detailed Description of Exemplary Embodiments, and elsewhere herein are incorporated by reference in their entirety as if each were individually incorporated.

Illustrative embodiments of this invention are discussed and reference has been made to possible variations within the scope of this invention. These and other variations, combinations, and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

What is claimed is:

1. A system for securing an electrical stimulation lead relative to a burr hole, the system comprising:
    a substantially ring shaped base having an opening surface defining a central opening extending therethrough and configured to be placed relative to the burr hole and an upper portion extending from the opening surface having a thickness that defines a channel formed in the upper portion extending from the opening surface toward an exterior of the upper portion, the upper portion having an outer radially curved surface that protrudes above an outer cranial surface above the burr hole where the channel is formed into the outer radially curved surface;
    a stabilizer separable from the base and shaped and sized to be inserted within the central opening of the base, wherein the stabilizer has a pair of opposed sidewalls defining a slot extending substantially continuous from and through an outer perimeter of the stabilizer and radially inward from the outer perimeter of the stabilizer, wherein the opposed sidewalls are resiliently biased to a closed position configured to engage the electrical stimulation lead, the opposed sidewalls facing each other in the closed position, each opposed sidewall including a plurality of open-ended notches formed therein starting from the outer perimeter and radially inward, the stabilizer having a pair of ears extending outward from the stabilizer and configured to engage a recess in the base to assist in positioning and holding the stabilizer in place relative to the central opening of the base; and
    a cap separate from and configured to be removably coupled to the base to cover the central opening and the burr hole, wherein the cap includes a substantially circular shape having an outer perimeter and at least one tab extending from the outer perimeter of the cap, the tab formed as an elongated protrusion configured to interlock with an opening in the base to secure the cap to the base.

2. The system of claim 1, wherein the base includes a pair of spaced apart apertures and wherein the channel is sized and shaped to receive a portion of the lead therein.

3. The system of claim 2, wherein the channel and the plurality open-ended notches are sized and positioned to secure the lead in a first direction by the plurality of open-ended notches and in a second direction by the channel.

4. The system of claim 2, wherein the stabilizer includes at least a portion received in a recess defined by the base.

5. The system of claim 1, wherein the stabilizer has two movable members, wherein each moveable member of the two moveable members forms one of the opposed sidewalls, the two movable members being resiliently biased towards one another with at least one of a spring or a resilient portion, wherein the opposed sidewalls face each other during movement to the closed position from an open position.

6. The system of claim 1, further comprising the electrical stimulation lead.

7. The system of claim 1, wherein the base defines a pair of apertures used to secure the base relative to the burr hole; and
    wherein the system further comprises a tool configured to be used in association with the apertures to secure the base relative to the burr hole.

* * * * *

UNITED STATES PATENT AND TRADEMARK OFFICE
CERTIFICATE OF CORRECTION

| | | |
|---|---|---|
| PATENT NO. | : 11,938,312 B2 | Page 1 of 1 |
| APPLICATION NO. | : 16/148373 | |
| DATED | : March 26, 2024 | |
| INVENTOR(S) | : Gregory T. Schulte et al. | |

It is certified that error appears in the above-identified patent and that said Letters Patent is hereby corrected as shown below:

In the Specification

Column 25, Line 19, Delete "204" and insert --1204-- therefor

Signed and Sealed this
Eighteenth Day of February, 2025

Coke Morgan Stewart
*Acting Director of the United States Patent and Trademark Office*